(12) United States Patent
Ybert et al.

(10) Patent No.: US 12,173,333 B2
(45) Date of Patent: *Dec. 24, 2024

(54) VARIANTS OF FAMILY A DNA POLYMERASE AND USES THEREOF

(71) Applicant: DNA Script, Le Kremlin-Bicêtre (FR)

(72) Inventors: Thomas Ybert, Paris (FR); Elise Champion, Paris (FR); Omar Vivar, Le Kremlin-Bicêtre (FR); Ahmed Said, Le Kremlin-Bicêtre (FR)

(73) Assignee: DNA Script, Le Kremlin-Bicêtre (FR)

( * ) Notice: Subject to any disclaimer, the term of this patent is extended or adjusted under 35 U.S.C. 154(b) by 0 days.

This patent is subject to a terminal disclaimer.

(21) Appl. No.: 17/858,801

(22) Filed: Jul. 6, 2022

(65) Prior Publication Data

US 2023/0193222 A1 Jun. 22, 2023

Related U.S. Application Data

(63) Continuation of application No. 16/636,875, filed as application No. PCT/EP2018/071217 on Aug. 6, 2018, now Pat. No. 11,390,856.

(30) Foreign Application Priority Data

Aug. 7, 2017 (EP) ..................... 17306052

(51) Int. Cl.
*C12N 9/12* (2006.01)
*C12N 1/21* (2006.01)

(52) U.S. Cl.
CPC .... *C12N 9/1252* (2013.01); *C12Y 207/07007* (2013.01)

(58) Field of Classification Search
None
See application file for complete search history.

(56) References Cited

U.S. PATENT DOCUMENTS

| | | | |
|---|---|---|---|
| 4,448,883 A | 5/1984 | Case |
| 4,772,691 A | 9/1988 | Herman |
| 5,436,143 A | 7/1995 | Hyman |
| 5,516,664 A | 5/1996 | Hyman |
| 5,602,000 A | 2/1997 | Hyman |
| 5,656,745 A | 8/1997 | Bischofberger |
| 5,744,595 A | 4/1998 | Srivastava |
| 5,763,594 A | 6/1998 | Hiatt |
| 5,808,045 A | 9/1998 | Hiatt |
| 5,872,244 A | 2/1999 | Hiatt |
| 5,917,031 A | 6/1999 | Miura |
| 5,935,527 A | 8/1999 | Andrus |
| 5,990,300 A | 11/1999 | Hiatt |
| 6,214,987 B1 | 4/2001 | Hiatt |
| 6,232,465 B1 | 5/2001 | Hiatt |
| 6,623,929 B1 | 9/2003 | Densham |
| 6,777,189 B2 | 8/2004 | Wei |
| 7,057,026 B2 | 6/2006 | Barnes |
| 7,078,499 B2 | 7/2006 | Odedra |
| 7,125,671 B2 | 10/2006 | Sood |
| 7,270,951 B1 | 9/2007 | Stemple |
| 7,407,757 B2 | 8/2008 | Brenner |
| 7,494,797 B2 | 2/2009 | Mueller |
| 7,544,794 B1 | 6/2009 | Benner |
| 7,939,259 B2 | 5/2011 | Kokoris |
| 8,034,923 B1 | 10/2011 | Benner |
| 8,212,020 B2 | 7/2012 | Benner |
| 8,263,335 B2 | 9/2012 | Carr |
| 8,674,086 B2 | 3/2014 | Liu |
| 8,808,988 B2 | 8/2014 | Zhao |
| 8,808,989 B1 | 8/2014 | Efcavitch |
| 9,896,709 B2 | 2/2018 | Makarov |
| 10,059,929 B2 | 8/2018 | Efcavitch |
| 10,435,676 B2 | 10/2019 | Champion et al. |
| 11,059,849 B2 | 7/2021 | Ybert |
| 11,390,856 B2 | 7/2022 | Ybert et al. |
| 2006/0240439 A1 | 10/2006 | Smith et al. |
| 2014/0363851 A1 | 12/2014 | Efcavitch |
| 2014/0363852 A1 | 12/2014 | Efcavitch |
| 2016/0108382 A1 | 4/2016 | Efcavitch et al. |
| 2018/0016609 A1 | 1/2018 | Chen et al. |
| 2018/0023108 A1 | 1/2018 | Chen |
| 2018/0274001 A1* | 9/2018 | Efcavitch ....... C12Y 207/07007 |
| 2018/0312820 A1 | 11/2018 | Pomerantz et al. |
| 2020/0002690 A1 | 1/2020 | Ybert et al. |
| 2020/0224181 A1* | 7/2020 | Delarue .............. C12N 15/102 |

FOREIGN PATENT DOCUMENTS

| | | |
|---|---|---|
| WO | 2016034807 A1 | 3/2016 |
| WO | 2016064880 | 4/2016 |
| WO | 2016128731 | 8/2016 |
| WO | 2017075421 | 5/2017 |
| WO | 2017216472 | 12/2017 |
| WO | 2018215803 | 11/2018 |

OTHER PUBLICATIONS

Zahn et al., Human DNA polymerase ⊖ grasps the primer terminus to mediate DNA repair, Nature Struct. and Mol. Biol. 22, 2015, 305-11. (Year: 2015).*
Uniprot, Accession No. 075417, 2017, www.uniprot.org (Year: 2017).*
QuikChange™ XL Site-Directed Mutagenesis Kit, Instruction Manual, Stratagene, 2000. (Year: 2000).*

(Continued)

*Primary Examiner* — Todd M Epstein
(74) *Attorney, Agent, or Firm* — MORRISON & FOERSTER LLP

(57) ABSTRACT

The present invention relates to variant of Family A polymerases able to synthesize a nucleic acid fragment without template and to incorporate a reversible modified terminator nucleotide during the nucleic acid fragment synthesis. The present invention further relates to uses thereof for enzymatic synthesis of nucleic acid molecules.

14 Claims, 16 Drawing Sheets

Specification includes a Sequence Listing.

(56) References Cited

OTHER PUBLICATIONS

Hogg et al., Lesion Bypass Activity of DNA Polymerase ⊖ (POLQ) Is an Intrinsic Property of the Pol Domain and Depends on Unique Sequence Inserts, J. Mol. Biol. 405, 2011, 642-52 (Year: 2011).*
Yousefzadeh et al., Mechanism of Suppression of Chromosomal Instability by DNA Polymerase POLQ, PLOS Genetics 10, 2014, e1004654. (Year: 2014).*
Uniprot, Accession No. L5L363, 2016, www.uniprot.org. (Year: 2016).*
Provision U.S. Appl. No. 62/560,693, filed Sep. 20, 2017. (Year: 2017).*
Uniprot, Accession No. G1QZF4, 2017, www.uniprot.org. (Year: 2017).*
U.S. Appl. No. 62/474,426, filed Mar. 21, 2017. (Year: 2017).*
Uniprot, Accession No. A0A0D9R4C0, 2017, www.uniprot.org. (Year: 2017).*
Schultz et al., Taq DNA Polymerase Mutants and 2'-Modified Sugar Recognition, Biochemistry 54, 2015, 5999-6008. (Year: 2015).*
ACCESSION No. A4PCE2, (2007).
Aoufouchi et al. (2000) "Two novel human and mouse DNA polymerases of the polX family," Nucleic Acids Research, 28(18): 3684-3693.
Arana et al. (2008) "Low-fidelity DNA synthesis by human DNA polymerase theta" Nucleic Acids Research 36(11): 3847-3856.
Beabealashvilli et al. (1986) "Nucleoside 5'-triphosphates modified at sugar residues as substrates for calf thymus terminal deoxynucleotidyl transferase and for AMV reverse transcriptase," Biochim. Biophys. Acta., 868(2-3): 136-144.
Bentoila et al. (1995) "The two isoforms of mouse terminal deoxynucleotidyl transferase differ in both the ability to add N regions and subcellular localization," The EMBO Journal, 14(17): 4221-4229.
Boule et al. (1998) "High-level expression of murine terminal deoxynucleotidyl transferase in Escherichia coli grown at low temperature and overexpressing argU IRNA," Molecular Biotechnology, 10: 199-208.
Database EPO Proteins, (2016) "Sequence 8 from Patent WO2016128731", XP002779827.
DATABASE UniProt, (2017) SubName: Full=DNA nucleotidylexotransferase isoform X1{EC0:0000313:RefSeq: XP_008057295.1}, XP002779838.
Delarue et al. (2002) "Crystal structures of a template-independent DNA polymerase: murine terminal deoxynucleotidyltransferase," The EMBO Journal, 21(3): 427-439.
Dominguez et al. (2000) "DNA polymerase mu (Pol □), homologous to TdT, could act as a DNA mutator in eukaryotic cells," The EMBO Journal, 19(17): 1731-1742.
Flickinger et al. (1992) "Differential incorporation of biotinylated nucleotides by terminal deoxynucleotidyl transferase," Nucleic Acids Research, 20(9): 2382.
Gouge et al. (2013) "Structures of intermediates along the catalytic cycle of terminal deoxynucleotidyltransferase: dynamical aspects of the two-metal ion mechanism," J. Mol. Biol., 425: 4334-4352.
Hogg et al. (2012) "Promiscuous DNA synthesis by human DNA polymerase Θ" Nucleic Acids Research 40(6): 2611-2622.
International Search Report from PCT International Application No. PCT/EP2018/071217 dated Feb. 14, 2019.
International Search Report from PCT International Application No. PCT/EP2019/050334 dated Feb. 22, 2019.
International Search Report from PCT International Application No. PCT/FR2017/051519 dated Jan. 18, 2018.
Koiwai et al. (1986) "Isolation and characterization of bovine and mouse terminal deoxynucleotidyltransferase cDNAS expressible in mammalian cells," Nucleic Acids Research, 14(14): 5777-5792.
Li et al. (1998) "Crystal structures of open and closed forms of binary and ternary complexes of the large fragment of Thermus aquaticus DNA polymerase I: structural basis for nucleotide incorporation" EMBO J. 17(24): 7514-7525.
Michelson et al. (1982) "Characterization of the homopolymer tailing reaction catalyzed by terminal deoxynucleotidyl transferase," J. Biol. Chem., 257(24): 14773-14782.
Motea et al. (2010) "Terminal deoxynucleotidyl transferase: The story of a misguided DNA polymerase," Biochim Biophys Acta, 1804(5): 1151-1166.
Patel et al. (2000) "DNA polymerase active site is highly mutable: Evolutionary consequences" Proc. Natl. Acad. Sci. USA 97(10): 5095-5100.
PIR Accession No. WXHU, published Dec. 4, 1986 (Year: 1986).
PIR Accession No. A23595, published Sep. 10, 1999 (Year: 1999).
PIR Accession No. S55786, published Oct. 27, 1995 (Year: 1995).
PIR Accession No. 151658, published Sep. 13, 1996 (Year: 1996).
Romain et al. (2009) "Conferring a template-dependent polymerase activity to terminal deoxynucleotidyltransferase by mutations in the Loop1 region," Nucleic Acids Research, 37(14): 4642-4656.
Schmitz et al. (1999) "Solid-phase enzymatic synthesis of oligonucleotides," Organic Lett., 1(11): 1729-1731.
Schott et al. (1984) "Single-step elongation of oligodeoxynucleotides using terminal deoxynucleotidyl transferase," Eur. J. Biochem., 143: 613-620.
Schultz et al. (2015) "Taq DNA Polymerase Mutants and 2'-Modified Sugar Recognition" Biochemistry 54: 5999-6008.
Shima et al. (2003) "Phenotype-Based Identification of Mouse Chromosome Instability Mutants" Genetics 163: 1031-1040.
Singapore Patent Office, Written Opinion in Singapore Patent Application No. 11201809961T (dated Apr. 24, 2020).
Song et al. (2021) "Large-Scale de novo Oligonucleotide Synthesis for Whole-Genome Synthesis and data Storage", Frontiers Bioeng. Biotechnol. 9, 2021, 689797.
Troshchynsky et al. (2015) "Functional analyses of polymorphic variants of human terminal deoxynucleotidyl transferase," Genes and Immunity, 16: 388-398.
UD-Dean, (2008) "A theoretical model for template-free synthesis of long DNA sequence," Syst. Synth. Biol., 2: 67-73.
Uniprot, Accession No. 075417 (2016) www.uniprot.org. 8 pages.
Written Opinion from PCT International Application No. PCT/EP2018/071217 dated Feb. 14, 2019.
Written Opinion from PCT International Application No. PCT/FR2017/051519 dated Jan. 18, 2018.
Yamtich et al. (2010) "DNA polymerase family X: function, structure, and cellular roles," Biochim. Biophys. Acta., 1804(5): 1136-1150.
Yang et al. (1994) "Mutational analysis of residues in the nucleotide binding domain of human terminal deoxynucleotidyl transferase," Journal of Biological Chemistry, 269(16): 11859-11868.
Yang et al. (1995) "T-cell specific avian TdT: characterization of the cDNA and recombinant ezyme," Nucleic Acids Research, 23(11): 2041-2048.
Yousefzadeh et al. (2014) "Mechanism of Suppression of Chromosomal Instability by DNA Polymerase POLQ" PLOS Genetics 10(10): e1004654, 15 pages.
Zahn et al. (2015) "Human DNA polymerase Θ grasps the primer terminus to mediate DNA repair" Nat Struc Mol Biol 22(4): 304-3011.
Database Refseq (2016) Predicted: DNA polymerase theta isoform X1 [Rhinolophus sinicus], XP-002776331, 2 pages.
Altschul, S.F et al. (2005). "Protein Database Searches Using Compositionally Adjusted Substitution Matrices," The FEBS Journal 272:5101-5109.
Altschul, S.F.et al. (Sep. 1, 1997). "Gapped BLAST and PSI-BLAST: A New Generation of Protein Database Search Programs," Nucleic Acids Res. 25(17):3389-3402.
Corpet, F. (Nov. 25, 1988). "Multiple Sequence Alignment with Hierarchical Clustering," Nucleic Acids Res. 16(22):10881-10890.
Needleman, S.B. et al. (Mar. 1970). "A General Method Applicable to the Search for Similarities in the Amino Acid Sequence of Two Proteins," J. Mol. Biol. 48:443-453.
Smith, T.F. et al. (1981). "Comparison of Biosequences," Advances in Appl. Math. 2:482-489.

(56) References Cited

OTHER PUBLICATIONS

Written Opinion mailed on Feb. 25, 2019, for PCT International Application No. PCT/EP2019/050334, filed on Jan. 8, 2019, 7 pages.

* cited by examiner

SEQUENCE LISTING

```
Sequence total quantity: 19
SEQ ID NO: 1              moltype = AA  length = 2590
FEATURE                   Location/Qualifiers
REGION                    1..2590
                          note = Human Pol theta
source                    1..2590
                          mol_type = protein
                          organism = synthetic construct
SEQUENCE: 1
MNLLRRSGKR RRSESGSDSF SGSGGDSSAS PQFLSGSVLS PPPGLGRCLK AAAAGECKPT   60
VPDYERDKLL LANWGLPKAV LEKYHSFGVK KMFEWQAECL LLGQVLEGKN LVYSAPTSAG  120
KTLVAELLIL KRVLEMRKKA LFILPFVSVA KEKKYYLQSL FQEVGIKVDG YMGSTSPSRH  180
FSSLDIAVCT IERANGLINR LIEENKMDLL GMVVVDELHM LGDSHRGYLL ELLLTKICYI  240
TRKSASCQAD LASSLSNAVQ IVGMSATLPN LELVASWLNA ELYHTDFRPV PLLESVKVGN  300
SIYDSSMKLV REFEPMLQVK GDEDHVVSLC YETICDNHSV LLFCPSKKWC EKLADIIARE  360
FYNLHHQAEG LVKPSECPPV ILEQKELLEV MDQLRRLPSG LDSVLQKTVP WGGVAFHHAGL  420
TFEERDIIEG AFRQGLIRVL AATSTLSSGV NLPARRVIIR TPIFGGRPLD ILTYKQMVGR  480
AGRKGVDTVG ESILICKNSE KSKGIALLQG SLKPVRSCLQ RREGEEVTGS MIRAILEIIV  540
GGVASTSQDM HTYAACTFLA ASMKEGKQGI QRNQESVQLG AIEACVMWLL ENEFIQSTEA  600
SDGTEGKVYH PTHLGSATLS SSLSPADTLD IFADLQRAMK GFVLENDLHI LYLVTPMFED  660
WTTIDWYRFF CLWEKLPTSM KRVAELVGVE EGFLARCVKG KVVARTERQH RQMAIHKRFF  720
TSLVLLDLIS EVPLREINQK YGCNRGQIQS LQQSAAVYAG MITVFSNRLG WHNMELLLSQ  780
FQKRLTFGIQ RELCDLVRVS LLNAQRARVL YASGFHTVAD LARANIVEVE VILKNAVPFK  840
SARKAVDEEE EAVEERRNMR TIWVTGRKGL TEREAAALIV EEARMILQQD LVEMGVQWNP  900
CALLHSSTCS LTHSESEVKE HTFISQTKSS YKKLTSKNKS NTIFSDSYIK HSPNIVQDLN  960
KSREHTSSFN CNFQNGNQEH QTCSIFRARK RASLDINKEK PGASQNEGKT SDKKVVQTFS 1020
QKTKKAPLNF NSEKMSRSFR SWKRRKHLKR SRDSSPLKDS GACRIHLQGQ TLSNPSLCED 1080
PFTLDEKKTE FRNSGPFAKN VSLSGKEKDN KTSFPLQIKQ NCSWNITLTN DNFVEHIVTG 1140
SQSKNVTCQA TSVVSEKGRG VAVEAEKINE VLIQNGSKNQ NVYMKHHDIH PINQYLRKQS 1200
HEQTSTITKQ KNIIERQMPC EAVSSYINRD SNVTINCERI KLNTEENKPS HFQALGDDIS 1260
RTVIPSEVLP SAGAFSKSEG QHENFLNISR LQEKTGTYTT NKTKNNHVSD LGLVLCDFED 1320
SFYLDTQSEK IIQQMATENA KLGAKDTNLA AGIMQKSLVQ QNSMNSFQKE CHIPPPAEQH 1380
PLGATKIDHL DLKTVGTMKQ SSDSHGVDIL TPESPIFHSP ILLEENGLFL KKNEVSVTDS 1440
QLNSFLQGYQ TQETVKPVIL LIPQKRTPTG VEGECLPVPE TSLNMSDSLL FDSFSDDYLV 1500
KEQLPDMQMK EPLPSEVTSN HFSDSLCLQE DLIKKSNVNE NQDTHQQLTC SNDESIIFSE 1560
MDSVQMVEAL DNVDIFPVQE KNHTVVSPRA LELSDPVLDE HHQGDQDGGD QDERAEKSKL 1620
TGTRQNHSFI WSGASFDLSP GLQRILDKVS SPLENEKLKS MTINFSSLNR KNTELNEEQE 1680
VISNLETKQV QGISFSSNNE VKSKIEMLEN NANHDETSSL LPRKESNIVD DNGLIPPTPI 1740
PTSASKLTFP GILETPVNPW KTNNVLQPGE SYLFGSPSDI KNHDLSPGSR NGFKDNSPIS 1800
DTSFSLQLSQ DGLQLTPASS SSESLSIIDV ASDQNLFQTF IKEWRCKKRF SISLACEKIR 1860
SLTSSKTATI GSRFKQASSP QEIPIRDDGF PIKGCDDTLV VGLAVCWGGR DAYYFSLQKE 1920
QKHSEISASL VPPSLDPSLT LKDRMWYLQS CLRKESDKEC SVVIYDFIQS YKILLLSCGI 1980
SLEQSYEDPK VACWLLDPDS QEPTLHSIVT SFLPHELPLL EGMETSQGIQ SLGLNAGSEH 2040
SGRYRASVES ILIFNSMNQL NSLLQKENLQ DVFRKVEMPS QYCLALLELN GIGFSTAECE 2100
SQKHIMQAKL DAIETQAYQL AGHSFSFTSS DDIAEVLFLE LKLPPNREMK NQGSKKTLGS 2160
TRRGIDNGRK LRLGRQFSTS KDVLNKLKAL HPLPGLILEW RRITNAITKV VFPLQREKCL 2220
NPFLGMERIY PVSQSHTATG RITFTEPNIQ NVPRDFEIKM PTLVGESPPS QAVGKGLLPM 2280
GRGKYKKGFS VNPRCQAQME ERAADRGMPF SISMRHAFVP FPGGSILAAD YSQLELRILA 2340
HLSHDRRLIQ VLNTGADVFR SIAAEWKMIE PESVGDDLRQ QAKQICYGII YGMGAKSLGE 2400
QMGIKENDAA CYIDSFKSRY TGINQFMTET VKNCKRDGFV QTILGRRRYL PGIKDNNPYR 2460
KAHAERQAIN TIVQGSAADI VKIATVNIQK QLETFHSTFK SHGHREGMLQ SDQTGLSRKR 2520
KLQGMFCPIR GGFFILQLHD ELLYEVAEED VVQVAQIVKN EMESAVKLSV KLKVKVKIGA 2580
SWGELKDFDV                                                       2590
```

```
SEQ ID NO: 2              moltype = AA   length = 799
FEATURE                   Location/Qualifiers
REGION                    1..799
                          note = pol Theta polymerase domain
source                    1..799
                          mol_type = protein
                          organism = synthetic construct
SEQUENCE: 2
GFKDNSPISD TSFSLQLSQD GLQLTPASSS SESLSIIDVA SDQNLFQTFI KEWRCKKRFS    60
ISLACEKIRS LTSSKTATIG SRFKQASSPQ EIPIRDDGFP IKGCDDTLVV GLAVCWGGRD   120
AYYFSLQKEQ KHSEISASLV PPSLDPSLTL KDRMWYLQSC LRKESDKECS VVIYDFIQSY   180
KILLLSCGIS LEQSYEDPKV ACWLLDPDSQ EPTLHSIVTS FLPHELPLLE GMETSQGIQS   240
LGLNAGSEHS GRYRASVESI LIFNSMNQLN SLLQKENLQD VFRKVEMPSQ YCLALLELNG   300
IGFSTAECES QKHIMQAKLD AIETQAYQLA GHSFSFTSSD DIAEVLFLEL KLPPNREMKN   360
QGSKKTLGST RRGIDNGRKL RLGRQFSTSK DVLNKLKALH PLPGLILEWR RITNAITKVV   420
FPLQREKCLN PFLGMERIYP VSQSHTATGR ITFTEPNIQN VPRDFEIKMP TLVGESPPSQ   480
AVGKGLLPMG RGKYKKGFSV NPRCQAQMEE RAADRGMPFS ISMRHAFVPF PGGSILAADY   540
SQLELRILAH LSHDRRLIQV LNTGADVFRS IAAEWKMIEP ESVGDDLRQQ AKQICYGIIY   600
GMGAKSLGEQ MGIKENDAAC YIDSFKSRYT GINQFMTETV KNCKRDGFVQ TILGRRRYLP   660
GIKDNNPYRK AHAERQAINT IVQGSAADIV KIATVNIQKQ LETFHSTFKS HGHREGMLQS   720
DQTGLSRKRK LQGMFCPIRG GFFILQLHDE LLYEVAEEDV VQVAQIVKNE MESAVKLSVK   780
LKVKVKIGAS WGELKDFDV                                                799

SEQ ID NO: 3              moltype = AA   length = 10
FEATURE                   Location/Qualifiers
REGION                    1..10
                          note = fragment of Pol theta
source                    1..10
                          mol_type = protein
                          organism = synthetic construct
SEQUENCE: 3
DYSQLELRIL                                                           10

SEQ ID NO: 4              moltype = AA   length = 8
FEATURE                   Location/Qualifiers
REGION                    1..8
                          note = fragment of Pol Theta
source                    1..8
                          mol_type = protein
                          organism = synthetic construct
SEQUENCE: 4
PGGSILAA                                                              8

SEQ ID NO: 5              moltype = AA   length = 16
FEATURE                   Location/Qualifiers
REGION                    1..16
                          note = fragment of Pol Theta
source                    1..16
                          mol_type = protein
                          organism = synthetic construct
SEQUENCE: 5
DDLRQQAKQI CYGIIY                                                    16

SEQ ID NO: 6              moltype = AA   length = 6
FEATURE                   Location/Qualifiers
REGION                    1..6
                          note = fragment of Pol Theta
source                    1..6
                          mol_type = protein
                          organism = synthetic construct
SEQUENCE: 6
EWRRIT                                                                6

SEQ ID NO: 7              moltype = DNA   length = 20
FEATURE                   Location/Qualifiers
source                    1..20
                          mol_type = other DNA
                          organism = synthetic construct
SEQUENCE: 7
taatacgact cactataggg                                                20

SEQ ID NO: 8              moltype = DNA   length = 19
FEATURE                   Location/Qualifiers
source                    1..19
                          mol_type = other DNA
                          organism = synthetic construct
SEQUENCE: 8
gctagttatt gctcagcgg                                                 19
```

```
SEQ ID NO: 9            moltype = DNA  length = 18
FEATURE                 Location/Qualifiers
source                  1..18
                        mol_type = other DNA
                        organism = synthetic construct
SEQUENCE: 9
aaaaaaaaaa aaaagggg                                                        18

SEQ ID NO: 10           moltype = AA  length = 2590
FEATURE                 Location/Qualifiers
source                  1..2590
                        mol_type = protein
                        organism = Homo sapiens
SEQUENCE: 10
MNLLRRSGKR RRSESGSDSF SGSGGDSSAS PQFLSGSVLS PPPGLGRCLK AAAAGECKPT    60
VPDYERDKLL LANWGLPKAV LEKYHSFGVK KMFEWQAECL LLGQVLEGKN LVYSAPTSAG   120
KTLVAELLIL KRVLEMRKKA LFILPFVSVA KEKKYYLQSL FQEVGIKVDG YMGSTSPSRH   180
FSSLDIAVCT IERANGLINR LIEENKMDLL GMVVVDELHM LGDSHRGYLL ELLLTKICYI   240
TRKSASCQAD LASSLSNAVQ IVGMSATLPN LELVASWLNA ELYHTDFRPV PLLESVKVGN   300
SIYDSSMKLV REFEPMLQVK GDEDHVVSLC YETICDNHSV LLFCPSKKWC EKLADIIARE   360
FYNLHHQAEG LVKPSECPPV ILEQKELLEV MDQLRRLPSG LDSVLQKTVP WGVAFHHAGL   420
TFEERDIIEG AFRQGLIRVL AATSTLSSGV NLPARRVIIR TPIFGGRPLD ILTYKQMVGR   480
AGRKGVDTVG ESILICKNSE KSKGIALLQG SLKPVRSCLQ RREGEEVTGS MIRAILEIIV   540
GGVASTSQDM HTYAACTFLA ASMKEGKQGI QRNQESVQLG AIEACVMWLL ENEFIQSTEA   600
SDGTEGKVYH PTHLGSATLS SSLSPADTLD IFADLQRAMK LYLVTPMFED              660
WTTIDWYRFF CLWEKLPTSM KRVAELVGVE EGFLARCVKG KVVARTERQH RQMAIHKRFF   720
TSLVLLDLIS EVPLREINQK YGCNRGQIQS LQQSAAVYAG MITVFSNRLG WHNMELLLSQ   780
FQKRLTFGIQ RELCDLVRVS LLNAQRARVL YASGFHTVAD LARANIVEVE VILKNAVPFK   840
SARKAVDEEE EAVEERRNMR TIWVTGRKGL TEREAAALIV EEARMILQQD LVEMGVQWNP   900
CALLHSSTCS LTHSESEVKE HTFISQTKSS YKKLTSKNKS NTIFSDSYIK HSPNIVQDLN   960
KSREHTSSFN CNFQNGNQEH QTCSIFRARK RASLDINKEK PGASQNEGKT SDKKVVQTFS  1020
QKTKKAPLNF NSEKMSRSFR SWKRRKHLKR SRDSSPLKDS GACRIHLQGQ TLSNPSLCED  1080
PFTLDEKKTE FRNSGPFAKN VSLSGKEKDN KTSFPLQIKQ NCSWNITLTN DNFVEHIVTG  1140
SQSKNVTCQA TSVVSEKGRG VAVEAEAKINE VLIQNGSKNQ NVYMKHHDIH PINQYLRKQS  1200
HEQTSTITKQ KNIIERQMPC EAVSSYINRD SNVTINCERI KLNTEENKPS HFQALGDDIS  1260
RTVIPSEVLP SAGAFSKSEG QHENFLNISR LQEKTGTYTT NKTKNNHVSD LGLVLCDFED  1320
SFYLDTQSEK IIQQMATENA KLGAKDTNLA AGIMQKSLVQ QNSMNSFQKE CHIPFPAEQH  1380
PLGATKIDHL DLKTVGTMKQ SSDSHGVDIL TPESPIFHSP ILLEENGLFL KKNEVSVTDS  1440
QLNSFLQGYQ TQETVKPVIL LIPQKRTPTG VEGECLPVPE TSLNMSDSLL FDSFSDDYLV  1500
KEQLPDMQMK EPLPSEVTSN HFSDSLCLQE DLIKKSNVNE NQDTHQQLTC SNDESIIFSE  1560
MDSVQMVEAL DNVDIFPVQE KNHTVVSPRA LELSDPVLDE HHQGDQDGGD QDERAEKSKL  1620
TGTRQNHSFI WSGASFDLSP GLQRILDKVS SPLENEKLKS MTINFSSLNR KNTELNEEQE  1680
VISNLETKQV QGISFSSNNE VKSKIEMLEN NANHDETSSL LPRKESNIVD DNGLIPPTPI  1740
PTSASKLTFP GILETPVNPW KTNNVLQPGE SYLFGSPSDI KNHDLSPGSR NGFKDNSPIS  1800
DTSFSLQLSQ DGLQLTPASS SSESLSIIDV ASDQNLFQTF IKEWRCKKRF SISLACEKIR  1860
SLTSSKTATI GSRFKQASSP QEIPIRDDGF PIKGCDDTLV VGLAVCWGGR DAYYFSLQKE  1920
QKHSEISASL VPPSLDPSLT LKDRMWYLQS CLRKESDKEC SVVIYDFIQS YKILLLSCGI  1980
SLEQSYEDPK VACWLLDPDS QEPTLHSIVT SFLPHELPLL EGMETSQGIQ SLGLNAGSEH  2040
SGRYRASVES ILIFNSMNQL NSLLQKENLQ DVFRKVEMPS QYCLALLELN GIGFSTAECE  2100
SQKHIMQAKL DAIETQAYQL AGHSFSFTSS DDIAEVLFLE LKLPPNREMK NQGSKKTLGS  2160
TRRGIDNGRK LRLGRQFSTS KDVLNKLKAL HPLPGLILEW RRITNAITKV VFPLQREKCL  2220
NPFLGMERIY PVSQSHTATG RITFTEPNIQ NVPRDFEIKM PTLVGESPPS QAVGKGLLPM  2280
GRGKYKKGFS VNPRCQAQME ERAADRGMPF SISMRHAFVP FPGGSILAAD YSQLELRILA  2340
HLSHDRRLIQ VLNTGADVFR SIAAEWKMIE PESVGDDLRQ QAKQICYGII YGMGAKSLGE  2400
QMGIKENDAA CYIDSFKSRY TGINQFMTET VKNCKRDGFV QTILGRRRYL PGIKDNNPYR  2460
KAHAERQAIN TIVQGSAADI VKIATVNIQK QLETFHSTFK SHGHREGMLQ SDQTGLSRKR  2520
KLQGMFCPIR GGFFILQLHD ELLYEVAEED VVQVAQIVKN EMESAVKLSV KLKVKVKIGA  2580
SWGELKDFDV                                                        2590

SEQ ID NO: 11           moltype = AA  length = 2536
FEATURE                 Location/Qualifiers
source                  1..2536
                        mol_type = protein
                        organism = Tupaia chinensis
SEQUENCE: 11
MNLLRRSGKR RRTDSGSDSF SGSGGDSCAS TVLLSKQLGC GQIPLPGEGR APTRVQYSLQ    60
ILNPGECKQT DPDDPIDKLL LANWGLPKAV LEKYHSFGVK KMFEWQAECL LLGQVLEGKN   120
LVYSAPTSAG KTLVAELLIL KRVLEMRKKA LFILPFVSVA KEKKYYLQSL FQEVGIKVDG   180
YVGSTSPTGH FSSLDIAVCT IERANGLINR LIEENKMDLL GMVVVDELHM LGDSHRGYLL   240
ELLLTKICYI TQKSASCQAD LVSPLFNGVQ IVGMSATLPN LDLIASWLNA ELYHTDFRPV   300
PLLETVKIGN SIYDSSMKLV REFQPMLQVK GDEDHIVSLC YETICDNHSV LLFCPSKKWC   360
EKLADTIARE FYNLHHQAEG LVKPPEFPPV TLEPKGLQEV MDQLKHLPSG LDSVLQKTVP   420
WGVAFHHAGL TFEERDIIEG AFRQGLIRVL AATSTLSSGV NLPARRVIIR TPIFGGRPLD   480
VLTYKQMVGR AGRKGVDTVG ESILVCKISE KSKGTALLQG SLKPVCSCLR RHEGEEVTAC   540
MIRAILEIIV GGVASTPQDM QNYASCTFLA ASMKEGQQEI ERNQSVQLG AIEACVMWLL    600
ENEFIQVAEV GDGTEGKVYH PTHLGSATLS SSLSPTDTLD IFADLQRAMK GFVLENDLHI   660
VYLITPMFED WTTIDWYRFF CLWEKLPISM KRVAELVGVE EGFLARCVKG KVVARTERQH   720
RQMAIHKRFF TSLVLLDLIS EVPLKEINQK YGCNRGQIQS LQQSAAVYAG MITVFSNRLG   780
```

```
WHNMELLLSQ FQKRLTFGIQ RELCDLVRVS LLNAQRARAL YASGFLTVAD LARANIADVE    840
MVLKNAVPFK SARKAVDEEE DAAEERRNMQ TIWVTGRKGL TEREAAALIV EEAKMILQED    900
LVEMGVQWNP HSPLNSSKLS LTSSDSEVKE LIFIPQTQSS CKRLISKNKS NSIFSDSYVK    960
RSLNTVQDLD KSRERHTSPI YKFQDKNQEY QRHSISKRAC LDISKEKPGT SLNEGRKSTQ   1020
KAVQTFSFEK TKIASNFSSD KMSTSFRSWK HRKHLKQSRS SSSVKDSSIS RTDLQRWRKS   1080
SPILCEDPSA LGERNVEFRS PGPFAKNVSF CVERKYDQTE QSCTRSGAIS NDIFVEHFDT   1140
GSQSKTMACQ TFGVVSENGR GLAIVETEKI NKVLIQNDSK NQNVNLKYCV THPVNQDLGK   1200
QCDQQTDTCT KQKEITERQM PFEAVSSNTN GDSDVTSVKC KSVKFNSEEN KPSHFQAFGN   1260
NISRTQIPSE IQVLTGTFRE SGGQHDSFQN TSKIQEKACA YLTNKTENNN VSDLGLVLCD   1320
FEDSFYLDTQ SEKIIQEIAT ENAKQAAEDP NLAAEKMQTN VQKQNLISSF QNALCVTLPG   1380
EQHSPGVTNT EPLDHKTGDT RHKPSTDSCR VDILTRENSV FHSPILLEEN SPCFKGNELS   1440
VTDSQLNNFL QGYQTQETVK PGIPVVPQKE TPTAMEGECL PVPETSLNMS DSLLFDSFNE   1500
DYLVKEQPAK VQAKETFLTT EITSDHFSDS LNIREGPAKT SSDINGNQDIH QQLTCFNDES   1560
LMFSEMDSAQ VVEVLDKLDI FPIQEKHNTA VSLSTLKLSD PVIVVNNHRQ GEVIGGEQDE   1620
KAQQSKITET GQNNSFMWSG ASFDLSPGLQ RILDKVSSPL ENEMLKSMPI NLSSLKGKNR   1680
ELNEKQEVIS NLDTSQMQRI SCFHTNEVKN NIAPENSVNH GAHLSPLSFK ESCIVDDNGL   1740
IPPTPVPASA SKFSFPGILG TSAVLQNTGS VLQSGGSYLF GSPSDTKNHE LSPDSRNGFK   1800
DESPRKEKSF SLQFSQDGLQ LTPASSNSQS LAIIDVASNQ TLFQTFIKEW QCKKRFSISL   1860
ACEKIGSSAS SKTATIGGRF KQGSSSQETP IRDGGFPVKG HEDILVVGLA VCWGGRDAYY   1920
FSLQQEQKHS EISASLNPPP LDPGLTVKDR LWHLQSCLQK KSGKECSVII YDFIQSYKIL   1980
LLSCGISLEQ DFEDPKVACW LLDPDSKEPT LHSIVTSFLP HELPLLEGME TGEGIQSLGL   2040
NVNTEHSGRY RASVESVLIF SCMTQLNSLL QKENLQDVFC KVEMPSQYCL ALLELNGIGF   2100
STAECESQKQ IMQAKLDAIE TEAYQLAGHS FSFTSSDDIA EVLFLELKLP PNGEMKNQGI   2160
KKTLGSTRRG IDSGRKLRLG RQFSTRRITF TEPNIQNVPR DFEIKMPTLV EESPPSQALG   2220
KGLLPMGRGK IKKGRRLNPE HQAHLEERAS DKGMPFSVSM RHAFVPFPGG LILAADYSQL   2280
ELRILAHLSH DHRLIQVLNT GADVFRSIAA EWKMIEPETV QNELRQQAKQ ICYGIIYGMG   2340
AKSLGEQMGI KENDAACYID SFKSRYTGIN HFMRETVKNC KRDGFVQTIL GRRRYLPGIK   2400
DNNPYHKAHA ERQAINTTVQ GSAADIVKVA TVNIQKQLET LRSTFKSHGH RESMLRRDKT   2460
GLLPKRKLQG MFCPIRGGFF ILQLHDELLY EVAEEDAVQV AQIVKNEMEN AIKLSVKLKV   2520
KVKIGASWAE LRDFDV                                                  2536

SEQ ID NO: 12          moltype = AA  length = 2383
FEATURE                Location/Qualifiers
source                 1..2383
                       mol_type = protein
                       organism = Cricetulus griseus
SEQUENCE: 12
MRKKALFILP FVSVAKEKKY YLQSLFQEVG IKVDGYMGSS SPTGRFSSLD IAVCTIERAN     60
GLINRLIEEN KMDLLGMVVV DELHMLGDSH RGYLLELLLT KICYVTRKST LCQADSARAL    120
CNAVQIVGMS ATLPNLQLVA SWLDAELYHT DFRPVPLLES IKIGNSIYDS SMKLVRELQP    180
VLQVKGDEDH IVSLCYETVC DNHSVLLFCP SKKWCEKVAD IIAREFYNLH HQPERLVKPS    240
EFPPVNLDQK SLLEVMDQLK RSPSGLDSVL KNTVPWGVAF HHAGLTFEER DIIEGAFRQG    300
LIRVLAATST LSSGVNLPAR RVIIRTPVFG GQTLDLITYK QMVGRAGRKG VDTMAAVYDK    360
FQIIVGGVAS TSQDMQTYAS CTFLAAAVKE GKQGIQRNQD DVHFGAIDAC VTWLLENEFI    420
QEAEPSDGSG GKVYHPTHLG SATLSSSLSP TDTLDIFADL QRAMKGFVLE NDLHIVYLVT    480
PVFEDWTGID WYRFFCLWEK LPTSMKRVAE LVGVEEGFLA RCVKGKVVAR TDRQHRQMAI    540
HKRFFTSLVL LDLISEIPLK EINQKYGCNR GQIQSLQQSA AVYAGMITVF SNRLGWHNME    600
LLLSQFQKRL TFGIQRELCD LIRVSLLNAQ RARFLYASGF LTVADLARAN VAEVEVVLKN    660
AVPFKSTRKA VDEEEAAEE RRNMQTIWVS GRKGLSAREA ATLIVEEAKT ILQQDDLEMG    720
VQWDPNSSLS SSTSSLTSSE SEVNERTLQS QTKNSHKRLT SKNRNSMRAS VSNDKPSPDT    780
AQGLGEHSEH TDSLCLLQGN KHQHQPHSVC RARKRTSLGI NKEKLRMSLN GGEPSTKEVL    840
QTFSMEKTRK AALTANSEQT NTSFPSWRDR KHRKKSWGSS PVRDSRANHH RDDFQEHTVS    900
RSTLCEEPLS LDKQNIEFRS SGLLIKNASF CANEKYNKTS FSLQMQQPCL RKKTESTGAV    960
EHSFAESQSK NVTGQSPGVA SNGRELADTE TGKINEVLIE NGAESQNVSV KHHDTHPISQ   1020
CLENQCDKQT NTCTKRKALI ERQVSCEAVS YMARDSNDVS TINSESIKLH SKDDESNHCQ   1080
VLGNNTGRSE APRGLLQSAA EFSQADGQHE HLLNSSGIQE KTDAYATNKT EHNHVSNLAP   1140
CDFGDSFYLD TQSEKIIEQL ATEHAKQRTL AVTAKGSDTR NSGSSFQNKC HSTRGEQHFQ   1200
RAANTDHLDS KSVETTKQNP EKSIGRLTAE SIIFHSPTPQ GENGPCFRVN EQSVTDSQLN   1260
SFLQGFETQE MVKPVLSLAP LAGTPTGLEE ENLPETSLNM SDSILFDSFG EDDLVKGQSP   1320
DVQAKQPLLS VMTPNHLSSS LCPREDPVMK ANVNDHQGIQ QPETCSSGES VIFSEVDSAQ   1380
MIEALDSVAA LHVQQNCNSV TLKTLELSDS AMLDNECPQG KVARGDKSER AQMSKLTETN   1440
QDNSITWSGA SFDLSPELQR ILDKGSSPLE NERPKLTQTN LSCFERNGTE LNERQEMNPN   1500
LEAVQIQRTS LFPNNGVQNK IEGIGNDTRR GEALYPSARK GSDTADDNGL IPPTPILAST   1560
SKLSFPEILG TSVNHLKADS VFLPGESCLF GSPSDSQERR DSFKDDRSVG DTSFSLQFSQ   1620
DELQLTPASC SSESLAIIDV ASDHTLFETF VKEWRCQKRF SISLACEKIR SPTSSKTATI   1680
GGRLKQVSSP QKTSAEDDGF PVHGSDGVIV VGLAVCWGGR DAYYLSLQKE QKHSVFPLRL   1740
LLQLNEFNFY IKTVLFQEIS PSLAPPPLDT TLTVEERMEH LQSCLQKKSD KEQTVVTYDF   1800
IQSYKILLLS CGVSLEPSYE DPKVACWLLD PDSKEPTLHS IVTSFLPEEL PLLEGIETGQ   1860
GIQSLGLNVD TEHSGRYRAS VESILIFNSM NQLNSLLQKE NLHDIFCKVE MPSQYCLALL   1920
ELNGIGFSTA ECESQKHIMQ AKLDAIETQA YQLAGHSFSF TSADDIAQDV LNKLKALHPL   1980
PGLILEWRRI SNAITKVVFP LQREKRLNPF LRMERLYPVS QSHTATGRIT FIEPNIQNVP   2040
RDFEIKMPTV VRESPPSQAP GKRLLPMTRG QNKKFYGLHP GNGTLMEEKA SDRGVPFSVS   2100
MRHAFVPFPV DNLLELRILA HLSRDCRLIQ VLNTGADVPR SIAAEWKMIE PDSVGEDLRQ   2160
QAKQICYGII YGMGAKSLGE QMGIKENDAA CYIDSFKSRY TGINHFLRET VKKCRRDGFV   2220
QTILGRRRYL PGIKDNNPYH KAHAERQAIN TTVQGSAADI VKTATVNIQK QLETFHSAFK   2280
SHGHRESMLQ HGQTGCGDLS PSPGQLVGLL PKKKLKGMFC PMRGGFFILQ LHDELLYEVA   2340
EEDVVQVAQI VKKEMECAVK LSVKLKVKVR MGASWGQLED FDV                    2383

SEQ ID NO: 13          moltype = AA  length = 2530
```

```
FEATURE              Location/Qualifiers
source               1..2530
                     mol_type = protein
                     organism = Rattus norvegicus
SEQUENCE: 13
MSLPRRSGKR RRSSSGSDSF SFSGDGDSCV SPQLLCRPVL SPPPGLGRGR RLAGTGTCKQ    60
RVSDDQIDQL LLANWGLPKA VLEKYHNFGV KKMFEWQAEC LLLGQVLEGK NLVYSAPTSA  120
GKTLVAELLI LKRVLETRKK ALFILPFVSV AKEKKYYLQS LFQEVGIKVD GYMGSTSPTG  180
RFSSLDVAVC TIERANGLIN RLIEENKMDL LGTVVVDELH MLGDSHRGYL LELLLTKVCF  240
VTRKSASCQA DSASALACAV QIVGMSATLP NLQLVASWLN AELYHTDFRP VPLLESIKVG  300
NSIYDSSMKL VREFQPLLQV KGDEDHIVSL CYETVRDNHS VLVFCPSKKW CEKVADIIAR  360
EFYNLHHQPE GLVKSSEFPP VILDQKSLLE VIDQLKRSPS GLDSVLKNTV PWGVAFHHAG  420
LTFEERDIIE GAFRQGLIRV LAATSTLSSG VNLPARRVII RTPVFGGQPL DILTYKQMVG  480
RAGRKGVDTM GESILVCKNS EKSKGIALLQ GSLEPVHSCL QSQGEVTSTM IRAILEIIVS  540
GVASTSQDMQ TYAACTFLAA DVKEGKQGIQ RNRDDVQRGA VDACVTWLLE NEFIQAAEPS  600
DGTGGKVYHP THLGSATLSS SLSPTDTLDI FADLQRAMKG FVLENDLHIV YLVTPVFEDW  660
TSIDWYRFFC LWEKLPTSMK RVAELVGVEE GFLARCVKGK VVARTERQHR QMAIHKRFFT  720
SLVLLDLISE IPLKEINQKY GCNRGQIQSL QQSAAVYAGM ITVFSNRLGW HNMELLLSQF  780
QKRLTFGIQR ELCDLIRVSS LNAQRARFLY ASGFLTVADL ARADTVEVEA ALKDALPFKS  840
ARKAVDEEEE AAEERRSMRT IWVAGKSLSA REAAALIVEE AKVILQQDLI EMGVQWGPHS  900
PLSSSTHSLT SGSEVKEHTF KSQTKSSHKR LASKSRNSMR VSGSNGKQSP EAGQGLDECR  960
ERPDSLCKFQ GNHEIQTPSV YRARKRTSLG VNKEMLRTSL KEGKPSTKEV LQTLSFEKTR 1020
KAALSFSSEQ ANNSFPSGRD RKYRKKSWGS SPMSDSVMHR DDLQGQTMCK STLCEDPQKS 1080
LEEQNTEYRS PGLFAKNVSF CAKEKCNKTS FPLQMQQPCL RRKPESGAAV DHSVAVSQNK 1140
NVVEQPPGAP RDRRGLAAHG RAEVNEVLTE NGTESQLHDT HPVSQCLENH SEKQTNTCTR 1200
QKTLTEGQAG ISHVTRGSND LTPIRCERLK LNSKEHDSNP CPQALGTNAG RTEAPQSSEA 1260
LGQAGGQCEN LLNSPGIQEK TSAHATNKTE HSHVANQAFC DFGDSLYLDT QSEEIIEQMA 1320
TKNATQGAEA AGITEEGSAT QNEPHSTTGG QHIPGAANTD HVDRKNTESV KENPEKNIDR 1380
RTPHSLIFHS PTPQGGNSAC FKENEHSVTD SQLNSFLQGL ETQDKPIIPL APQMRTSTGV 1440
EEESLPETSL NMSDSILFDS FGEDSFGQRQ SLDVKAKQPL LSEMTPNHFH NPPYPQEDPV 1500
MTPHMSEPQG TLERMACLSG ESIIFSEIDS AQVIEALDNM AAFYMQENCN PITLKTEPRD 1560
LAALGNECPQ GEVVRGEQHE GSSKPKFMEI NQDNSFTWSA ASPNLSPELQ RILDKVSTPR 1620
ENEEPELMHA DLSCFEENST ESHERQDMNS DLGTVQRTSF LPSNGVKSRT EGLESKAKHG 1680
GASSALPHKA AADDNGLIPP TPLPASASAS ASKLALPEIL GTSVKHQKAS CLFDSPSDNQ 1740
NQDLSQELRD SLKDSDGSVV DTSFFLQSQD GLLLTQASCS SESLAIIDVA SDQILFQTFV 1800
KEWQCQKRFS ISLACEKMTS STSSKTATIG GRLKQVNSPQ EASVEDDGFP VHGSDCAVVV 1860
GLAVCWGGKD AYYLSLQKEQ KQSEMSPSLA PPPLDATLTV KERMEYLQSC LQKKSDQERS 1920
VVTYDFIQTY KVLLLSCGIS LEPSYEDPKV ACWLLDPDSK EPTLHSIVTS FLPHELALLE 1980
GIETGPGIQS LGLNVNTDHS GRYRASVESV LIFNSMNQLN SMLQKENLHD IFCKVEMPSQ 2040
YCLALLELNG IGFSTAECET QKHIMQAKLD AIETQAYQLA GHSFSFTSAD DIAQVLFLEL 2100
KLPPNGEMKT QGGRKTLGST RRGTESDRKL RLGRRFSTSK DILNKLKDLH PLPGLILEWR 2160
RISNAITKVV FPLQREKHLN PFLRMERIYP VSQSHTATGR ITFTEPNIQN VPRDFEIKMP 2220
TLVRESPPSQ ASGKGQLAMA RQNQKVYGLH PGQRTVLEKT SDRGVPFSVS MRHAFVPFPG 2280
GLILAADYSQ LELRILAHLS RDCRLIQVLN SGADVFRSIA AEWKMIEPDA VGDNLRQQAK 2340
QICYGIIYGM GAKSLGEQMG IKENDAACYI DSFKSRYKGI NHFMRDTVKN CRRDGFVETI 2400
LGRRRYLPGI KDNNPYHKAH AERQAINTTV QGSAADIVKV ATVNIQKQLE TFHPTFKSHG 2460
HRESMLQSDR AGLLPKRKVK GMFCPMRGGF FILQLHDELL YEVAEEDVVQ VAQIVKNEME 2520
CAIKLSVKLK                                                       2530

SEQ ID NO: 14        moltype = AA   length = 2577
FEATURE              Location/Qualifiers
source               1..2577
                     mol_type = protein
                     organism = Alligator sinensis
SEQUENCE: 14
MAFFSKGQCQ RMNIPEDQAD KLLLASWGLP KAVLEKYHSL GVVHMFKWQA ECLMLGQVLE    60
GKNLVYSAPT SAGKTLVAEL LILKRVLETH KKALFILPFV SVAKEKKYYL QALFQEVGVR  120
VEGYMGSTSP AGRFSTLDVA VCTIERANGL INRLIEENQM DLLGMVVVDE LHMLGDSHRG  180
YLLELLLTKV RFITEKVTKR QAKASSPAFG GIQIVGMSAT LPNLHLLASW LNAELYHTDF  240
RPVPLMEWVK IGSNIYDSSM NLVREFQPML QLKGDEDHVV SLCYETVRDG HSVLLFCPSK  300
NWCEKLANII AREFCNLQLS DRKTSNLPPI PLYKEAIEEV MDQLRRSLSG LDSVLQRTLP  360
WGVAFHHAGL TFDERDVIEG AFRQGLIRVL AATSTLSSGV NLPARRVIIR TPVFGGKLLD  420
ILAYKQMAGR AGRKGADTVG ESILVCKPSE RSKGIALLQG SLKPVRSCLL RREGEGITSS  480
MIRAILEIIV GGVASTPDDV RTYASCTLLV ASLKDNEQGS EKNEDGVQNG AIEACVAWLL  540
QNEFIQVSGP SDGVKAEVYC PTHLGSATLS SSLSPMEALE IFADLQRAMK GFVLENDLHI  600
VYLVTPVYEE WTTIDWYQFF CLWEKLPASM KRVAELVGIE EGFLARSVKG KIIAKTEKQH  660
RQMAIHKRFF TSLALLDLIS EVPLKDITKR YGCSRGQLQS LQQSAATYAG MVTVFSNRLG  720
WHNMEQLLSQ FQSRLTFGVH RELCDLVRVS LLNAQRARAL CIWMAGMKHV TENEAASLVV  780
EEARMLLQQD LAVMGVQWNP DSYLDSESSS SMISSESELE DRKYRLSREG SFETLKAFNK  840
ERYGLHPNSQ SGTSAKIEKG NKRLLGASTP KGRLQSEAQI DQIQTEEGNI DVIVQSARKR  900
PHLSKDKENM EFTSKRKSKA GFRETSQESP TEEGKRPTLS FVPTKTSAVC RPRRIMGGSL  960
NQSRNCSRAL KQHRSLLEES RRQITGIKGP PLSRHSSSES KSFPDGSNKE LTEKGSLVHK 1020
DKISGSFHEH YPLIGSKEKM EGLLMEPSVT NECKPKEKTI CQASRDVIMR DAATVRMETS 1080
DTVGGLMIPS RELKNENIGA KDSKVHAGKK YAKRISGKQQ MILDTDLCNE IVSSSAKTHV 1140
SDGAYKQKTV CYEPKSCLFP IQSKSKHSSE SPNGVLFKSG GVGKAADNQP EDFLRDSIIK 1200
SRAVCIAKSS KNGYAHDLSL GYGYFEDSFQ LDTQTDRIIQ QQVASEIAGH QGAKGTELAA 1260
IAVQKTFTKL PCDNAFQTES VADKNLVAAF REMDSSGLVT TLGMKQPTDL CCSDKTLGSV 1320
SSCLQSAVKF PDAALCLRGN DFSVTDSQLH SFLQGYLTQP SVKESVCLGL QNGAPVSNGQ 1380
NPHIIHVQVE 1440
```

```
CHPIPETSLN TSNSLLFEDS FSDLNDPSGI RAGEAEGVET REQEILPFPP NTISSSLVGC  1500
LHQQSWGPIQ DVWSINQVEE QQPPQCNDAS LTFSEIDSFQ LAEAFDNVSS PPFQGDLPSA  1560
ALVEPELRKS VAQEDSGPMD IKGDKSVRPQ KAQQNVKKNP NSIVWSEHSF ELSPGLQEIL  1620
DKWPSPSGNK PASSSPSIPG SKEKLVLSNC SQEQGAVFEF GCGQKKPLPL CQGLENYFTG  1680
RESNRGALEQ KPNCSPKFLK GSSRKRDPQP DISNGLIPPT PPMEPAPKSF GMSSLKSGKK  1740
KDVILMNEGP LCQVLQNGIP VSDQQIETLQ FNPENGDPLE IDPVKEDSVI DQDFSLQLSQ  1800
DILPLISCSA ESFTIIDVAS DMALFQTFIQ EWRNKNRFAI SVACERTKRL LSSRSTIGGR  1860
FKQVRSPQQI QVKDDGFPIK GCEDTLIVGL AVCWGGKDAY YVSLQQKADD QAEVSASLAP  1920
PALDQNLSVT ERLCHLQSCL QKEPEGKHCL VMYDFIQHYK TLLMACGISL EGSFEDPKVA  1980
CWLLDPGSKE RTLHNMVTSF LPHELPLLEG IGTGQGVQSL GLSASADHSG RYRAAVESVL  2040
IFGIMNQLNT LLQKENLTDA FCKVEMPTQY CLALLELNGI GFSTVACETQ KHIMQAKLNE  2100
IETQAYQLAG HSFSLTSPDD IAEVLFLELK LPNGDVKAQG NKKTLGYTRR CTTKGHRIRL  2160
GKQFSTTKDA LEKLKTLHPL PGLILEWRRI TNAVTKVVFP LQREKRLNSL LGMERIYPIS  2220
QTHTATGRIS FAEPNIQNVP KDFEIEMPTL VEESPPSQAR RNVSALPGAR SRKHHSILPQ  2280
GSNSVAEEGP KGRGMPFSVS MRHAFVPFPG GLILAADYSQ IELRILAHLS GDRRLIQALN  2340
SGADVFKSIA AEWKMIDPEA VRDDTRQQAK QICYGIIYGI GAKSLGEQMG VEENDAASYI  2400
DSFKSRYKGI QKFLRETVNN CSRDGFVKTI LGRRRYLPAI RDPNPYSKAH AERQAVNTTV  2460
QGSAADLVKT ATVNIQRRLE AFPSTIKSHG HLESSFQMDR AGRLERRRNR RMLHPITGGF  2520
FILQLHDELL YEVAEDDVIQ VAQIVKHEME NAMKLSVKLN VKVRIGPSWG DLQDLEL     2577

SEQ ID NO: 15        moltype = AA  length = 2596
FEATURE              Location/Qualifiers
source               1..2596
                     mol_type = protein
                     organism = Pan troglodytes
SEQUENCE: 15
MNLLRRSGKR RRSESGSDSF SGSGGDSSDS PQLLSGSVLS PPPGLGRCLK DRGRQSAAAA  60
GECKPTVPDY EIDKLLLANW GLPKAVLEKY HSFGVKKMFE WQAECLLLGQ VLEGKNLVYS  120
APTSAGKTLV AELLILKRVL EMRRKALFIL PFVSVAKEKK YYLQSLFQEV GIKVDGYMGS  180
TSPSRHFSSL DIAVCTIERA NGLINRLIEE NKMDLLGMVV VDELHMLGDS HRGYLLELLL  240
TKICYITRKS ASCQADLASS LSNAVQIVGM SATLPNLELV ASWLNAELYH TDFRPVPLLE  300
SVKVGNSIYD SSMKLVREFE PMLQVKGDED HVVSLCYETI RDNHSVLLFC PSKKWCEKLA  360
DIIAREFYNL HHQAEGLVKP SECPPVILEQ KELLEVMDQL RRLPSGLDSV LQKTVPWGVA  420
FHHAGLTFEE RDIIEGAFRQ GLIRVLAATS TLSSGVNLPA RRVIIRTPIF GGRPLDILTY  480
KQMVGRAGRK GVDTVGESIL ICKNSEKSKG IALLQGSLKP VRSCLQRREG EEVTASMIRA  540
ILEIIVGGVA STSQDMHTYA ACTFLAASMK EGKQGIQRNQ ESVQLGAIEA CVMWLLENEF  600
IQSTEASDGT EGKVYHPTHL GSATLSSSLS PADTLDIFAD LQRAMKGFVL ENDLHILYLV  660
TPMFEDWTTI DWYRFFCLWE KLPTSMKRVA ELVGVEEGFL AVCKGKVVA  RTERQHRQMA  720
IHKRFFTSLV LLDLISEVPL REINQKYGCN RGQIQSLQQS AAVYAGMITV FSNRLGWHNM  780
ELLLSQFQKR LTFGIQRELC DLVRVSLLNA QRARVLYASG FHTVADLARA NIVEVEVILK  840
NAVPFKSARK AVDEEEEAVE ERRNMRTIWV TGRKGLTERE AAALIVEEAR MILQQDLVEM  900
GVQWNPCALL HSSTCSLTHS ESEVKEHTFI SQTKSSYKKL TSKNKSNTIF SDSYIKHSPN  960
IVQDLNKSRE HTSSFNCNFQ NGNQEHQRCS IFRARKRASL DINKEKPGAS QNEGETSDKK  1020
VVQTFSRKTK KAPLNFNSEK MSRSFRSWKH RKHLKRSRDS SPLKDSGACR IHLQGQTLSN  1080
PSLCEDPFTL DEKKTEFRNS GPFAKNVSLS GKEKDNKTSF PLQIKQNCSW NITLTNDDFV  1140
EHIVTGSQSK NVTCQATSVV SEKGRGVAVE AEKINEVLIQ NGSKNQNVYI KHHDIHPINQ  1200
YLRKQSHEQT STITKQKNII ERQMPCEAVS SYINRDSNVT INCERIKLNT EENKPSHFQA  1260
LGDDISRTVI PSEVLPSAGA FSKSEGQHEN FLNISRLQEK TGTYTTNKTK NNHVSDLGLV  1320
LCDFEDSFYL DTQSEKIIQQ MATENAKLGA KDTNLAAGIM QKSLVQQNSM NSFQKECHIP  1380
FPAEQHPLGA TKIDHLDLKT VGTMKQSTDS HGVDILTPES PIFHSPILLE ENGLFLKKNE  1440
VSVTDSQLNS FLQGYQTQET VKPVIPLIPQ KRTPTGVEGE CLPVPETSLN MSDSLLFEDP  1500
SDDYLVKEQL PDMQMKEPLP SEVTSNHFSD SLCLQEDLIR KSNVENQDT  HQQLTCSNDE  1560
SIIFSEMDSV QMVEALDNAD IFPVQEKNHT VVSPRALELS DPVLDEHHQG DQDGEDQDER  1620
AEKSKLTGTR QNHSFIWSGA SFDLSPGLQR ILDKVSSPLE NEKLKSMTIN FSSLNRKNTE  1680
LNEEQEVISN LETKQVQGIS FSSNNEVKSK IEMLENNAHN DETSSLLPRK ESNIVDDNGL  1740
IPPTPIPTSA SKLTFPGILE TPVNPWKTNN VLQPGESYLF GSPSDIKNHD LSPGSRNGFK  1800
DNSPISDTSF SLQLSQDGLQ LTPASSSSES LAIIDVASDQ NLFQTFIKEW RCKKRFSISL  1860
ACEKIRSLTS SKTATIGSRF KQASSPQEIP IRDDGFPIKG CDDILVVGLA VCWGGRDAYY  1920
FSLQKEQKHS EISASLVPPS LDPSLTLKDR MWYLQSCLRK ESDKECSVVI YDFIQSYKIL  1980
LLSCGISLEQ SYEDPKVACW LLDPDSQEPT LHSIVTSFLP HELPLLEGME TSQGIQSLGL  2040
NAGSEHSGRY RASVESILIF NSMNQLNSLL QKENLQDVFR KVEMPSQYCL ALLELNGIGF  2100
STAECESQKH IMQAKLDAIE TQAYQLAGHS FSFTSSDDIA EVLFLELKLP PNREMKNQGS  2160
KKTLGSTRRG IDNGRKLRLG RQFSTSKDVL NKLKALHPLG GLILEWRRIT NAITKVVFPL  2220
QREKRLNPFL GMERIYPVSQ SHTATGRITF IEPNIQNVPR DFEIKMPTLV GESPPSQAVG  2280
KGLLPMGRGK YKKGFSVNPR CQAQMEERAA DRGMPFSISM RHAFVPFPGG SILAADYSQL  2340
ELRILAHLSH DRRLIQVLNT GADVFRSIAA EWKMIEPESV GDDLRQQAKQ ICYGIIYGMG  2400
AKSLGEQMGI KENDAACYID SFKSRYTGIN QFMTETVKNC KRDGFVQTIL GRRRYLPGIK  2460
DNNPYRKAHA ERQAINTIVQ GSAADIVKIA TVNIQKQLET FHSTFKSHGH REGMLQSDRT  2520
GLSRKRKLQG MFCPIRGGFF ILQLHDELLY EVAEEDVVQV AQIVKNEMES AVKLSVKLKV  2580
KVKIGASWGE LKDFDV                                                2596

SEQ ID NO: 16        moltype = AA  length = 2665
FEATURE              Location/Qualifiers
source               1..2665
                     mol_type = protein
                     organism = Fundulus heteroclitus
SEQUENCE: 16
MRPWQQPRDP GVCHVGEENA RMASGPLKKK SYLGQHQIKK KTSIPAGDHE PTDGDGLLQK  60
PSDKTNRAQS SGRDGLMGGR GALLPLGEST LALDEEMLQT LDAADLSKGD VKRDGKGAFP  120
```

```
PPRPAPQTAR LKLDGKPAKV DGESLPFTNG AEDPQQGGCK PRWDSNKPGW RADCKDLAQK    180
LLFSEDSGEA DRCTRNQENN RSDDAPASAS ALPCKETRSR QKAGGSRKQE LRGRGSPPSD    240
GKDKSMKNTD PPLDVSTDYI LFSPTRLAEA RRRAKLQQSL HNQSVSVLTV PSGLELSTLS    300
DTLPPPGVAV RAPERQAEKL LLSSWGLPKP VLERYQNHGV TRMFEWQAQC LAVGQALRGG    360
NLVYSAPTSA GKTLVSELLI LKRVLETRRK ALFILPFKVS AKEKMHYLQS VFEEAGIRVE    420
GYMGSTSAAG GFTTLDVAVC TIEKANSLIN RLIEENSMDL LGVVVVDELH MVGDSGRGYL    480
LELLLTKIRY IAQKQNTSGS LAEGVQIIGM SATLPNLSLL AGWLGADLYQ TDYRPVPLQE    540
HLKVGGNIYD RSLSVVRQFT PALNVKGDDD HIVSLCYETV REGHSVLLFC PSKNWCEKLA    600
DTIARAFFNL RNTDPQSEGV PPPVCLDTAG LVDVIAQLRR TPAGLDPILQ RTVPWGVGFH    660
HAGLTFDERD VLEGAFRQGL VRVLAATSTL SSGVNLPARR VVIRTPVFNG RLLDPLTYKQ    720
MAGRAGRKGV DTTGESVLVC KQSEHQKGIS LLQGALQPIS SCLVRREGEG VTTSMLRAIL    780
EVIVGGVASS PRDVRLYASC SLLAASTKGD GGKESTEETS SGAIEACVDW LMGNEFISIQ    840
RDGQDEQYCP TQLGAATLSS SLSPPEALGI FADLQRAMKG FVLESDLHIL YLITPLYAEW    900
TTIDWYQFFC LWEQLPSSMK RVAELVGVQE GFLARSVSGK IVAKTEKQLR QMAVHKRFFT    960
TLVLQDLVSE VPLGAVASKY NCNRGQLQSL QQSASTYAGM VTVFCKRLGW HNMELLLSQY   1020
QTRLSFGVQR ELVDLVRLSL LNATRARALY AQGLCTVAQV ARAPVADVEK ALRNAVPFKS   1080
SKRAVDESEM EAAERRNLRC VWWTGGRALT EQEAAAEIVS EARLLLQEDL AQLGVHWDPS   1140
TLPPQAPSGS SSDDHSGDS  DAASAPRVAP RRSPMRRTEG HPSGTHTGRR NVSKSRGEEI   1200
GRDAEIQEKV AYGKGALEGE ARKPDVTDPE ISDVLVERAE GRNEAKPSTS RQDEAEHVED   1260
KQETAGAVQH GGRLESISLV EEDRRKRNKS VEEQTHHYLN QPAVEMSLTQ ELAEIVSSPL   1320
PPPPPQPQPP PSPAPPPRFR APVSRLAHRP SAPTSTGKGG CSTSPLLPRT PKHSAALRKV   1380
LQSIQTGRGV QDRLQPADLS PSKVPNAAPV TLQENPDVAS TPPGADSAPL FTPEAKRRRT   1440
EAGGVDRFSS PELYAGSKTD EEEQGDAEEE EEEESFGRSL DLDTQTERMI AQRPLTGTAG   1500
GRDEAGEQQG ERRGDRVKGP DDDRRDEAEG PETAAARFQI SVTESQMELI LNSNPRASPS   1560
PARGDTDQAG DDRQLSDNNE AAAESPDGSS GFLFDSMHDS ALLDTLLLNP SPEPAGEEEE   1620
PAGPAPAPSA QQKRRSELLA NQEAEEQEAV RWGESFFCLS WEGESFLVGE AFLGRQALSR   1680
HAEGGEGNQG LQQPSKEEES EEEKAGGRQR DEEKDAKHVE KLTGEERENL IENDVLKTPG   1740
VQNSPESAFY CSPGLQEIFD RWPSMSDQPG PTADTADATE LPRPATQPGR KRKQPQRPDA   1800
TQKAPPERP  GSAGDLIPPT QETAPVTPRV KLTTSSVLSP AVTQPLKQST PSHRLQEGPT   1860
DGERATAHAA VSVSDRRPQR SPPTGRSLFF PPQTAASPPS PRPEPPSDAE SPVSPGGFAL   1920
QLSQDASLLC SDSGSFSIID VASDRRLFDT FIKEWETKER FSVALACERR AHRRRPEDDT   1980
GGRRKRASAA HPTPDGFPVG DDEGRTLIGL SVCWGARDAY YVSLQQEQSE GLSSSLAPPP   2040
LDKALPVTQR LQRVKACLSA APSGRRGRAV VVYDIIKVYK RLVRSCGISL EGNYEDPKVA   2100
CWLLDPGREE RTLPNMVTVY CPEELPLVDG LGNAHSHCPR VRAATESVLV HAVMQHLSGL   2160
LERDGALDVF RRTEMPSQVC LALLELNGVG FSAEECERQK HVMQAKLSAL EAEAYSLAGH   2220
SFSLTSVDDV AQVLFLELHL PPNGDVDGPR SKKTLGYTRR GGGRARLGKQ FSTTKDVLEK   2280
LRPLHPLPGV ILEWRRITNA LTKVVFPLQR EKRYEPTLDM DRIYPVAQTH TATGRVSFTE   2340
PNIQNVPKDF EISLPTVVGE SPPSQGGFQM PNRPGRRRSV APLPAAADQG PAFSVSMRHA   2400
FVPFSGGMIL AADYSQLELR VLAHLSKDQR LLQVLNGGAD VFRCIAAEWK SVEPASVQDD   2460
LRQQAKQICY GIIYGMGAKS LGEQMGVEEN DAACYIESFK ARYKGINAFL KQTVKKCLKD   2520
GYVQTLMGRR RYLAGIANAN PHVKAHAERQ AVNTTVQGSA ADIVKLATVN IQKRLRETYP   2580
SAPLSHQHAH SAHNNQRRFG TSRLRGAYFI LQLHDELIYE TTERDLIQVA QIVKREMESA   2640
VKLYVKLKAK VKVGPSWGNL QDLDI                                        2665

SEQ ID NO: 17          moltype = AA  length = 2674
FEATURE                Location/Qualifiers
source                 1..2674
                       mol_type = protein
                       organism = Crassostrea gigas
SEQUENCE: 17
MTSKSKNGGM ELDASFSSSF CTELDAQMLV AMETMEKQPR SQKSLPKGTK KNSPVLTSTP     60
QSVTPLPRRQ AQLMKSLFTL QSPLNDSLFS PFSSQTTDNV KDGEQLTPSS AMNGKPCRKR    120
TRKVLNEIIN EKERIDEDNG DKLLLKNWGL PEPVMKQYSD KGITSMFEWQ AECLCLPGVL    180
DGGNLVYSAP TSAGKTMVAE LLVLKRVLET KKKAIIILPF VSVAREKMFY LQQLYQEVGV    240
SVSGFMGSYS PPGGLSQVDV AVCTIEKGNG LINRLMEENR LDQLGIVVID ELHLVGDQHM    300
GYLLELMLTK IRFLSQRMKK PDPQNMESSS TEGIQIIGMS ATLPNLDLLA RWLDATLYRT    360
DYRPVPLTEC VKLGADIFDS RLQKIREVDL SVTFKGDTDH VVPLCLETLR DGHSVLIFCP    420
TKNWCEKLAE TIAREFYGIL KKAPVDMQAN QGSGGNPPSP CLPLSRASLQ EVVEQLRRTP    480
VGLDSTLGKT VPYGVAYHHA GKYQHKFIVR VKEDPGGARL YPEEDCPYVV AHHHTGLTFD    540
ERDILEGAFR QGAVKVLIAT STLSSGVNLP ARRVIIRTPL FHGKTIDFLT YKQMIGRAGR    600
KGVDTQGESI LICKPGERSK AVTLVQSALP PVSSCLIKNQ GEQLSSSMKR AILEIVVSGV    660
ADSVTDVTAY ASCTMLAASL DTSSDQTQGM ISACIQFLQE NEFVSLQRVQ SSDGVYEDRF    720
VPTQLGAAVL ASSLSPDEGL SVFAELQKAR QCFVLENELH IVYLVTPIYS LDLGAGMNWY    780
KFYCLWDKLS PDKKRVAQLV GVSEAFLTRA IQGRIPTKTE NQIRSLAIHK RFYTSLILSD    840
LVQEVPLGEV CHRYGANKGQ LQSLQQTAAT FAGMVTVFCA RLGWYNLELI LGQFQHRLTF    900
GIQRELCDLV RLTLLNGQRA RVLYDGGFHT VAALANASVS DVEKIFKKSS PFQSSKKLEN    960
ETEWEAARRQ ESRCIWLTGR KGATEREAAQ AIIQEAKSLI QQELGLGIQ  WKTPDTRKSL   1020
EEGSNPDQNG MDCSRDLEKS SNNHQIGLMK MKSKGSVRKR RSLSRKSPAL SQARSSRGKG   1080
FNRQEKSVVI SPPSFNSQSR RNKSNIGTDS GSGKPCDNDC IVIVDDSSGD PNERQGNKEI   1140
PSIKDFVVRQ IEEQSCQQRN RNNPEKRDCE KNCTSEVRVQ PNHMYHKDQL QIDLVKTNAN   1200
CNEEAGKQLT GLHEAREKPR VEAIKANPSR CTERENVSAS SSSSSSSSTS SSVINSSSRP   1260
AEDSHVFKSP IFSSVSTGIK KSGPKTRSSS FPLSTLSTSS TSLGSSTASV VMSPQLAKNK   1320
NDLIKIPSNK RNAMPNQSIQ RGILSGVQQI ITNSTDLETV NGKLNEHESD VRTINERQK    1380
ADLTPEANFR ELRDRGDSEE RKKLQEEIKV KTIEPMICSE DFADSFVFES QMDGNMEAFP   1440
GLCNEVSQSL QSKKTLGDSE KINSKIVVDK IIEKQINSNG FFQPNGSSSS KKHLVRNAHI   1500
VVEKHRTNTA LSTADAATVN KEQVDDEHST GNDMNLSCCS LLSSHDVSCD LLPASNFEKC   1560
MVSDDESDVC RDESYRDLRI PYLSGQEAAC FDGNERKADL ALGGYQISQG LLQELDETFS   1620
EECSQGSKGQ SQRSAGQGGS FKNGKKQNNS SIDGMEASKV EQGKATEQNL KTFEKKKNGQ   1680
IIERKMEEAE VGVTEEMDDS LTLSMVYEVI ENCDKGQCNK NLNSKTDKSN TNQLTSRRSS   1740
```

```
QRNAKSNSKK TNEIICEELI SKKSSECNKR STLKSKESSF TKVKCSRSSQ DKDKRLSPGT  1800
LAFLDDLHTS LDTDSDTIVM KTPLCQRRRG NNNKEGSTRD SVVMDEVMDE DLQNEYSGED  1860
NVRTNECLSP TPPRLSLVNS PKTIRKATPN RHRPQKQDDR RSARKNIESL GVSMKNSKVP  1920
FVESAKSAEE EVREWNSGKL ESPTGEDPPY VERGPVVDPN ETGIPPSQGA FTIIDVCADK  1980
VLFDTFIKEW NCQPSFAISL ACINKPRDPV TTTGGIGAKF TEAGDTGHKS SKVKTTEPGV  2040
ASRGIPVWGV NLVITGVAVS WGDRDAYFIT LTSENIEDEE DTDLSPPDLD KSLSVTARLA  2100
AIRQVLERKD SFTVIAMDAK ACYGALERSC GICCQGEFQD PKVATWLLDP GAKEKNLHRM  2160
VHDYLPLEAF LLEDIGGGVG YGSIGMSPEN PGSSRVRSCT EAVLLTHLMQ FYTLCFNDEE  2220
CERQKNIMVA RLGDLEEQAY RCVGHQFSLT STEDLSQILF IELQLPVNGD PSSLGQPMRP  2280
NRRAPNSHRG RQKSQFSTTK EVLEKLRPLH PFPGILLEWR RISGSLTKVV FALQKEKVYC  2340
ENLGMHRIFT DVQYFTATGR VSLSEPNLQN VPKDFLISVS APVENFNQWD AAGHRNKNRN  2400
SGQTSFNVSM RHAFIPFPGG VLLAADYSQL ELRMIAHLSQ DSKLIKILNG DGDVFKLITA  2460
QWKSISVEEV TPEQRQQAKQ ICYGMIYGIG AKALGDTLGV EENDAAAFIQ TFKSKYPGMR  2520
RYLKDTVDKC CKNGYVETIS GRRRYLPSIS NKKPYVRAHA ERQAVNTTVQ GSAADLVKVA  2580
MNRIDDRLSA MFPLSKKTFS YKEDEVQGIE LSSSDRCCLVL QLHDELIYEV TERCLGQAAK  2640
VIKEEMETAM TLSVKMPVKV KSGLSWATMQ DLAV                              2674

SEQ ID NO: 18           moltype = AA   length = 2544
FEATURE                 Location/Qualifiers
source                  1..2544
                        mol_type = protein
                        organism = Mus musculus
SEQUENCE: 18
MSLPRRSRKR RRSSSGSDTF SGDGDSFVSP QLRCGPVLSP PPGLGRGRRL TGTGTNKRRV  60
SDDQIDQLLL ANWGLPKAVL EKYHSFGVRK MFEWQAECLL LGHVLEGKNL VYSAPTSAGK  120
TLVAELLILK RVLETRKKAL FILPFVSVAK EKKCYLQSLF QGVGLKVDGY MGSTSPTGQF  180
SSLDIAVCTI ERANGLVNRL IEENKMDLLG MVVVDELHML GDSHRGYLLE LLLTKICYVT  240
RKSASHQAES ASTLSNAVQI VGMSATLPNL QLVASWLNAE LYHTDFRPVP LLESIKIGNS  300
IYDSSMKLVR EFQPLLQVKG DEDHIVSLCY ETIQDNHSVL IFCPSKKWCE KVADIIAREF  360
YNLHHQPEGL VKSSEFPPVI LDQKSLLEVM DQLKRSPSGL DSVLKNTVPW GVAFHHAGLT  420
FEERDIIEGA FRQGFIRVLA ATSTLSSGVN LPARRVIIRT PIFSGQPLDI LTYKQMVGRA  480
GRKGVDTMGE SILVCKNSEK SKGIALLQGS LEPVHSCLQR QGEVTASMIR AILEIIVGGV  540
ASTSQDMQTY AACTFLAAAI QEGKQGMQRN QDDAQLGAID ACVTWLLENE FIQVAEPGDG  600
TGGKVYHPTH LGSATLSSSL SPTDTLDIFA DLQRAMKGFV LENDLHIVYL VTPVFEDWIS  660
IDWYRFFCLW EKLPTSMKRV AELVGVEEGF LARCVKGKVV ARTERQHRQM AIHKRFFTSL  720
VLLDLISEIP LKDINQKYGC NRGQIQSLQQ SAAVYAGMIT VFSNRLGWHN MELLLSQFQK  780
RLTFGIQREL CDLIRVSLLN AQRARFLYAS GFLTVADLAR ADSAEVEVAL KNSLPFKSAR  840
KAVDEEEEAA EERRSMRTIW VTGKGLSARE AAALIVEEAK MILQQDLIEM GVRWDPKSLN  900
SSSTHSRTST SEVKEHTFKS QTKSSHKRLA SMGRNSIRAS GSNDKPSPDA ERGIDDCSEH  960
ADSLCKFQGN FEPQTPSICT ARKRTSLGIN KEMLRKSLKE GKPSTKEVLQ TFSSEKTRKT  1020
ALSFSSEQVN NTLPSGRDRK YQKKSWGSSP VRDSGMHRGD LQGQTMCTSA LCEDSQKSLE  1080
EQNAEFRSPG LFAKHLPSCA KEKCKKPSLP LQRQQACSRR STESCAAVGH PAAGSSPAAA  1140
RDRRGLAARE TEKGNEALTE NGGESQLQDT YPVSQYLEYH SEKHTNTCTR QKTLTEGQAG  1200
SSYVARDSND AAPIKCERMK LNSKDRDSNP CRQALGSYTG RTEALQSTAK LGQAGGQCEN  1260
LLNSSGVQGK TGAHATNRTE HSHASNPAFC DFGDSLDLDT QSEEIIEQMA TENTMQGAKA  1320
VVIMEEGSAM QNKCHSTPGD QHVPGAANTD HVDSKKVESV KANTEKNINR GAPVSLIFHT  1380
QGENGACFKG NEHSVTDSQL NSFLQGFETQ EIVKPIIPLA PQMRTPTGVE EESLPETSLN  1440
MSDSILFDSF GEDGFGQGQS PDIKANQPLL SEMTPNHFSN PPHPQEDPVM TPTVSEPQGT  1500
QQQGVCLSGE SIIFSDIDSA QVIEALDNMA AFHVQENCNS VALKTLEPSD SAVLGNECPQ  1560
GKLVRGDQNE GSPKPKLTET NQDNSFTWSG ASFNLSPELQ RILDKVSSPR ENEKPKMIHV  1620
NLSSFEGNSK ESHEREEINS DLGTVQRTSV FPSNEVKNRT EGLESKARHG GASSPLRKE  1680
SAAADDNGLI PPTPVPASAS KVAFPEILGT SVKRQKASSA LQPGESCLFG SPSDNQNQDL  1740
SQELRDSLKD YDGSVADTSF FLQSQDGLLL TQASCSSESL AIIDVASDQI LFQTFVKEWQ  1800
CQKRFSISLA CEKMTSSMSS KTATIGGKLK QVSLPQEATV EDAGFPVRGC DGAVVVGLAV  1860
CWGAKDAYYL SLQKEQKQSE ISPSLAPPPL DATLTVKERM ECLQSCLQKK SDRERSVVTY  1920
DFIQTYKVLL LSCGISLEPS YEDPKVACWL LDPDSKEPTL HSIVTSFLPH ELALLEGMET  1980
GPGIQSLGLN VNTEHSGRYR ASVESVLIFN SMNQLNSLLQ KENLHDIFCK VEMPSQYCLA  2040
LLELNGIGFS TAECESQKHV MQAKLDAIET QAYQLAGHSF SFTSADDIAQ VLFLELKLPP  2100
NGEMKTQGSK KTLGSTRRGN ESGRRMRLGR QFSTSKDILN KLKGSLHPLPG LILEWRRISN  2160
AITKVVFPLQ REKHLNPLLR MERIYPVSQS HTATGRITFT EPNIQNVPRD FEIKMPTLVR  2220
ESPPSQAPKG RFPMAIGQDK KVYGLHPGHR TQMEEKASDR GVPFSVSMRH AFVPFPGGLI  2280
LAADYSQLEL RILAHLSRDC RLIQVLNTGA DVFRSIAAEW KMIEPDAVGD DLRQHAKQIC  2340
YGIIYGMGAK SLGEQMGIKE NDAASYIDSF KSRYKGINHF MRDTVKNCRK NGFVETILGR  2400
RRYLPGIKDD NPYHKAHAER QAINTTVQGS AADIVKIATV NIQKQLETFR STFKSHGHRE  2460
SMLQNDRTGL LPKRKLKGMF CPMRGGFFIL QLHDELLYEV AEEDVVQVAQ IVKNEMECAI  2520
KLSVKLKVKV KIGASWGELK DFDV                                        2544

SEQ ID NO: 19           moltype = DNA   length = 2397
FEATURE                 Location/Qualifiers
source                  1..2397
                        mol_type = other DNA
                        organism = synthetic construct
SEQUENCE: 19
ggcttcaagg acaatagtcc gatcagtgac acttctttca gtttacagct gtcacaagac  60
ggccttcaat taacacctgc ctccagctca tccgaaagcc tttcgatcat tgacgtcgcc  120
tcggatcaaa atttgttcca gacctttatt aaagaatggc gttgcaaaaa acgcttcagt  180
atttcgttgg cgtgtgaaaa gatccgctct cttacgtcca gtaagacagc gacaatcggt  240
tcgcgcttca agcaggccag ctcacccaa  gagattccca tccgcgacga cggttttcct  300
atcaaagggt gtgatgacac tttggtgtg ggtctggcag tttgctgggg aggacgtgat  360
```

-continued

```
gcgtattact tcagcttgca gaaagaacaa aaacactccg aaatctctgc gtccttggtc    420
cccccttcat tggacccatc attaacgctt aaagatcgta tgtggtactt gcagagttgt    480
ttacgcaaag aaagcgacaa agaatgtagt gtggtcatct atgatttcat ccagagctac    540
aaaatcttgt tgttatcctg tggcatctct ctggagcaga gctatgaaga tccgaaggta    600
gcctgttggc ttttggaccc ggattcgcaa gagccaaccc tgcattcaat cgtcaccagc    660
ttccttccac atgaactgcc tcttttagag ggaatggaga cctcgcaggg aatccaatct    720
cttggactta atgctggatc tgaacacagt ggacgctatc gcgcgtcagt tgaatcaatc    780
ctgattttta actcgatgaa tcaacttaat tccctgcttc agaaagaaaa ccttcaggac    840
gtctttcgta aggtggaaat gccttcgcaa tattgcttag ccttattaga gttgaatgga    900
atcggatttt ccactgcaga gtgtgagtcc cagaaacata tcatgcaggc caaactggat    960
gcaatcgaga cacaagctta ccagcttgcg ggtcatagct tcagcttcac atcctccgac   1020
gatatcgccg aagtcttgtt tttggaatta aagctgcctc ctaatcgcga gatgaagaat   1080
caaggctcca agaagacatt aggttcaacc cgccgtggaa tcgacaatgg tcgtaaatta   1140
cgtctgggcc gccagtttag cacatctaaa gacgtcctta ataagctgaa agccttgcac   1200
cctcttccgg gcctgatttt ggagtggcgc cgtattacaa atgccatcac caaagtagtt   1260
ttcccattgc agcgcgagaa gtgtcttaat ccattccttg ggatggagcg tatctatccc   1320
gtcagccagt cacatactgc aacgggacgc attactttca cggagccaaa catccaaaat   1380
gtccccccgcg acttcgagat taaaatgcct actctggttg gggagtctcc tcctagccaa   1440
gctgtgggca agggactgct gcctatgggt cgtggcaaat acaaaaaggg ctttagtgtt   1500
aacccacgct gccaggctca gatggaggag cgcgctgcag atcgtggaat gccttttct    1560
atcagcatgc gtcacgcatt cgtcccccttc caggggaa gtatcttagc ggctgattac     1620
tctcaattgg aacttcgtat tctggcgcac cttagtcatg accgtcgctt gattcaggta   1680
ctgaatactg gagcggacgt gtttcgttcg attgctgcgg agtggaaaat gatcgagccc   1740
gaatccgtcg gtgatgatct tcgtcaacag gcaaaacaga tctgttacgg gatcatctat   1800
ggaatgggtg ctaaatcctt gggtgagcaa atggggatta aggagaacga tgccgcatgc   1860
tacattgata gcttcaaatc acgttacacc ggtattaatc aatttatgac tgagaccgtg   1920
aaaaactgta aacgtgacgg cttcgtccaa acaattttag ggcgtcgccg ctatttaccg   1980
ggaattaagg acaacaatcc ctaccgcaaa gcacatgccg aacgtcaagc aatcaacact   2040
attgtccaag gttcggctgc tgatatcgtg aaaattgcca cagtcaacat ccagaaacag   2100
ctggagacgt ttcattcaac atttaaaagc cacggacacc gtgaaggcat gctgcaatcg   2160
gaccaaactg gtctgtcacg taagcgtaaa ttgcagggta tgttctgtcc gattcgcgga   2220
ggcttcttta tcttacaatt acacgacgag ctgttgtatg aagttgccga ggaagatgtc   2280
gtccaggtgg ctcagattgt taagaacgaa atggaatctg ctgtgaagtt gtctgtgaag   2340
cttaaagtca aagttaaaat tggtgcttcg tgggggagt tgaaagactt cgatgtt       2397
```

VARIANTS OF FAMILY A DNA POLYMERASE AND USES THEREOF

CROSS-REFERENCE TO RELATED APPLICATIONS

This application is a continuation of U.S. patent application Ser. No. 16/636,875, filed Feb. 5, 2020, issued as U.S. Pat. No. 11,390,856, which is a 371 national phase of International Application Serial No. PCT/EP2018/071217, filed Aug. 6, 2018, which claims priority to European Patent Application Serial No. 17306052.6, filed Aug. 7, 2017, which applications are incorporated herein by reference in their entirety.

INCORPORATION BY REFERENCE OF SEQUENCE LISTING

A Sequence Listing is provided herewith as a Sequence Listing XML, DNAS-005CON_SEQ_LIST created on Dec. 27, 2022 and having a size of 48,637 bytes. The contents of the Sequence Listing XML are incorporated herein by reference in their entirety.

FIELD OF THE INVENTION

The invention relates to variants of family A DNA polymerase and uses thereof for the enzymatic synthesis of nucleic acid sequences without template. More particularly, the present invention relates to such variants suitable to incorporate terminator modified nucleotides, for the synthesis of nucleic acid molecules with determined or controlled sequences.

BACKGROUND

Methods for de novo chemical synthesis of nucleic acids based on solid-phase phosphoramidite chemistry have been largely used and refined over the past 40 years. The technique consists of a four-step chain elongation cycle that adds one base per cycle onto a growing oligonucleotide chain attached to a solid support matrix. Although it has been the method of choice to synthesize nucleic acids during the past decades, this technology has some notable limitations: It requires the use of multiple solvents and reagents, and due to limitations in chemical reaction efficiency, the length of synthetic oligonucleotides typically do not exceed 150-200 bases. Moreover, these short fragments need to be further assembled to provide the desired DNA sequence.

One alternative to chemical synthesis consists in using template independent DNA polymerases that will add reversible terminator modified nucleotides to a growing single stranded chain of nucleic acids. This allows the addition of one type of nucleotide per cycle in a controlled fashion.

Some native enzymes are able to act on natural nucleotides in the absence of template and so can catalyze the synthesis of nucleic acids in an uncontrolled fashion. However, they are particularly inefficient to incorporate reversible terminator modified nucleotides. Efforts have been made to develop new DNA polymerases able to act on modified nucleotides but the resulting enzymes are not fully satisfactory in term of performance for the synthesis of any type of nucleic acids.

So far only few DNA polymerases that can act efficiently on single strand DNA (without the use of template) have been identified. The most characterized polymerase having such template-independent activity is the Terminal deoxynucleotidyl Transferase (TdT). TdT enzymes have been extensively used to modify single stranded DNA for various types of applications including biotechnology, biomedical research and synthetic biology. However, native TdT is poorly able to use 3'modified nucleotides.

It has also been discovered recently that the human DNA polymerase Pol θ possesses a robust template-independent activity using optimized conditions. In particular, this enzyme is known to be more effective in transferring ribonucleotides to single stranded DNA compared to TdT. As for TdT, the native DNA polymerase Pol θ is unable to recognize efficiently 3'-modified nucleotides.

There is therefore a need to develop new robust and efficient DNA polymerases capable to use modified nucleotides in the absence of template to provide an improved method for the nucleic acid synthesis.

SUMMARY OF THE INVENTION

It is therefore an object of the present invention to provide a variant of a DNA polymerase of family A, and more particularly of a Pol θ, which is able to incorporate a modified terminator nucleotide during the nucleic acid fragment synthesis.

More particularly, it is an object of the invention to provide a variant of a DNA polymerase of family A, which (i) comprises the amino acid sequence set forth in SEQ ID No2 or a functionally equivalent sequence, with at least one amino acid mutation at any one of the amino acid residue as compared to SEQ ID No2, (ii) is able to synthesize a nucleic acid fragment without template and (iii) is able to incorporate a modified terminator nucleotide during a nucleic acid fragment synthesis.

Preferably, the variant is a variant of Pol θ, which has at least 40% identity with the amino acid sequence set forth in SEQ ID No1.

Preferably, the variant shows an increased ability to incorporate a reversible modified terminator nucleotide during a nucleic acid fragment synthesis as compared to a DNA polymerase of SEQ ID No1.

According to an embodiment, the variant is able to incorporate a 3'O-modified nucleotide.

In an embodiment, the variant comprises at least one mutation, preferably selected from a substitution, a deletion or an addition, in at least one of the amino acid sequence as set forth in SEQ ID No3, SEQ ID No4, SEQ ID No5 or SEQ ID No6, or functionally equivalent sequences.

For instance, the variant comprises at least one substitution in the amino acid sequence as set forth in SEQ ID No3, selected from the group consisting of D2330E/R/H/K/T/V/A/G, Y2331F/W/P/H/M/L/V/A, S2332T/N/Q/V/A/G, Q2333N/T/S/A/G/V, L2334M/E/N/F/K/D/A/G, E2335G/A/N/T/S/D, L2336M/E/N/F/K/D/A/G, R2337H/K/D/E/A/G/M/F, I2338V/A/G/L/T/S/D/K/M, L2339M/E/N/F/K/D/A/G/I, wherein the positions are numbered by reference to the amino acid sequence set forth in SEQ ID No1.

Alternatively or in addition, the variant may comprise at least one substitution in the amino acid sequence as set forth in SEQ ID No4 selected from the group consisting of P2322A/V/I/L/G/C, G2323C/P/A/V/K/D, G2324C/P/A/V/K/D, S2325 L/N/M/V/T/A/G/D/K, I2326V/A/G/L/T/S/D/K/M, L2327M/E/N/F/K/D/A/G/I/V, A2328V/T/G, A2329V/T/G, wherein the positions are numbered by reference to the amino acid sequence set forth in SEQ ID No1.

Alternatively or in addition, the variant may comprise at least one substitution in the amino acid sequence as set forth in SEQ ID No5 selected from the group consisting of D2376E/R/H/K/T/V/A/G/N, D2377E/R/H/K/T/V/A/G/N, L2378M/E/N/F/K/D/A/G/I, R2379H/K/D/E/A/G/M/F, Q2380N/T/S/A/G/V, Q2381N/T/S/A/G/V, A2382V/T/G, K2383R/H/D/E/Q/N/C/A/G/S/T, Q2384N/T/S/A/G/V, I2385V/A/G/L/T/S/D/K/M, C2386G/P/A/V/S/N/Q/D/K, Y2387F/W/P/H/M/L/V/A, G2388C/P/A/V/K/D, I2389V/A/G/L/T/S/D/K/M, I2390V/A/G/L/T/S/D/K/M, Y2391F/W/P/H/M/L/V/A, wherein the positions are numbered by reference to the amino acid sequence set forth in SEQ ID No1.

Alternatively or in addition, the variant may comprise at least one substitution in the amino acid sequence as set forth in SEQ ID No6 selected from the group consisting of E2199G/A/N/T/S/D/K, W2200Y/F/P/L/I/V/A/G/E, R2201H/K/D/E/A/G/M/F/S/P, R2202H/K/D/E/A/G/M/F/S/P, I2203V/A/G/L/T/S/D/K/M/P, T2204S/N/Q/C/G/M/K/D, wherein the positions are numbered by reference to the amino acid sequence set forth in SEQ ID No1.

In an embodiment, the variant comprises at least one amino acid mutation, preferably of at least two mutations, more preferably three mutation at position(s) corresponding to residues selected from D2330, D2540 or E2541, or residues functionally equivalent, excluding D2540N/A or E2541Q/A, wherein the positions are numbered by reference to the amino acid sequence set forth in SEQ ID No1. Preferably, the amino acid mutations are amino acid substitutions selected from D2330E/R/H/K/T/V/A/G, D2540E/K/R/H/Q/S/T/C and E2541D/R/H/K/N/S/T/C, wherein the positions are numbered by reference to the amino acid sequence set forth in SEQ ID No1.

In an embodiment, the variant comprises at least one amino acid mutation, preferably selected from a substitution, a deletion or an addition, at position(s) corresponding to residues selected from K2181, R2315, F2359, Y2391 and A2477, or residues functionally equivalent, excluding substitution K2181A and deletion of R2315. Preferably, the mutation is a substitution selected from K2181R/H/D/E/Q/N/C/G/S/T, R2315H/K/D/E/A/G/M/F, F2359M/L/I/V/A/G/P/T/K/D, A2477V/T/G.

In an embodiment, the variant comprises at least one amino acid mutation of a residue having side chain groups positioned within 15 Å, 12 Å, 10 Å, 8 Å or 6 Å of a 3'O extremity of a nucleotide, or residue functionally equivalent.

In an embodiment, the variant comprises at least substitution or combination of substitutions as listed in TABLE 9, wherein the positions are numbered by reference to the amino acid sequence set forth in SEQ ID No1.

In an embodiment, the variant further comprises the amino acid sequence as set forth in SEQ ID No7.

In an embodiment, the variant has at least 75%, 80%, 85%, 90%, 95%, 97%, 98% or 99% identity to the full length amino acid sequence set forth in SEQ ID No1, It is also an object of the invention to provide a nucleic acid molecule encoding a variant of a DNA polymerase of family A of the invention.

It is a further object of the invention to provide an expression vector comprising such nucleic acid molecule.

It is a further object of the invention to provide a host cell comprising such nucleic acid molecule or such expression vector.

The present invention also provide a process for producing a variant of a DNA polymerase of family A of the invention, wherein a host cell of the invention is cultivated under culture conditions allowing the expression of the nucleic acid encoding said variant, and wherein the variant is optionally retrieved.

It is also the purpose of the invention to provide the Use of such a variant of a DNA polymerase of family A, for synthesizing a nuclei acid molecule without template, with 3'O-modified nucleotide.

The present invention also provides a process for synthesizing a nucleic acid molecule with template, comprising a step of contacting a nucleic acid primer with both at least one nucleotide, preferably at least one 3'O-modified nucleotide, and a DNA polymerase of family A of the invention.

The present invention also provides a kit for performing a nucleotide incorporation reaction comprising a DNA polymerase of family A of the invention, and one or more nucleotides, preferably one or more 3'O-modified nucleotides, and optionally at least one nucleic acid primer.

DESCRIPTION OF THE INVENTION

Figure 1:
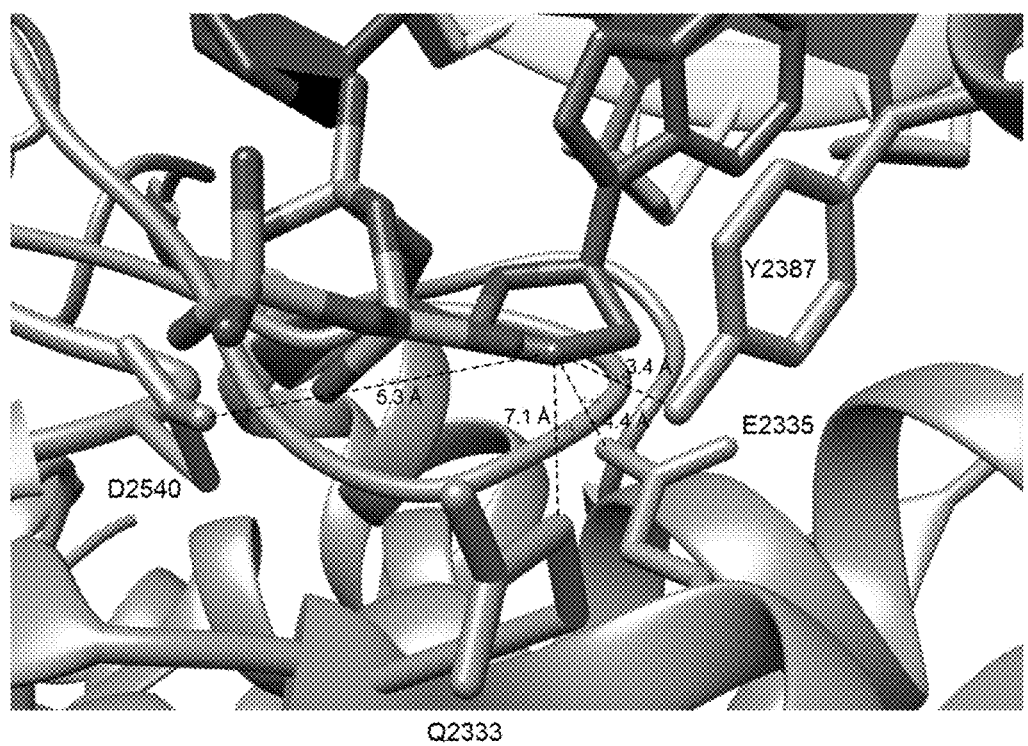
FIG. 1: Structural analysis of the catalytic pocket of the Human Pol Theta (Pol θ) polymerase using PDB crystal structure 4X0P and Chimera software. The picture shows 4 residues Q2333, E2335, Y2387 and D2540 and their respective distance (in angstrom) to the 3' extremity of the sugar ring of a ddATP.

The present invention relates to variants of Family A DNA polymerase, which exhibit increased ability to incorporate modified reversible terminator nucleotides as compared to parent or native Family A DNA polymerases.

Definitions

The DNA polymerase families are divided into seven families based on their sequence homology and crystal structure. Among them, the polymerases of family A are classes either replicative polymerases or repair polymerases. Polymerases from family A are present across very wide range of organisms and microorganisms. Eukaryote and prokaryote cells are expressing polymerases from Family A. Among animals both vertebrates and invertebrates express Family A polymerases. The replicative polymerases have the best fidelity rate and require template strand for activity. The repair polymerases are involved in reparation of various DNA lesions or errors. They show a largely decrease fidelity but retain a high activity rate even in presence of degraded template or for some particular polymerases in absence of template.

The present invention relates of the engineering and subsequent modifications of A Family polymerase. In a particular aspect of the invention the Family A polymerase are from the repair type and have the ability to conserve a high nucleotide incorporation rate even if the template strand is absent.

Polymerase Theta (Pol θ) is a particular polymerase of the A Family. Pol θ belongs to the repair type of Family A polymerases and is naturally implicated in DNA repair and maintenance mechanisms. In particular Pol θ is able to perform DNA repair activity in very bulky lesions. It also has the unique ability to conserve a nucleotide polymerization activity even when no template strand is present. In specific condition and with natural nucleotides, Pol θ is able to elongate with several hundreds of nucleotides, DNA fragments without any complementary strand to be present.

The present invention relates to the engineering and subsequent modifications of Pol θ polymerase. In a particular aspect of the invention Pol θ is used in such condition that it show polymerization activity in absence of any template strand of DNA or other nucleic acid molecules.

Pol θ is able to polymerize both natural deoxyribonucleotides (dNTP) and ribonucleotides (rNTP). Various modified nucleotides, baring permanent labeled modifications on the base moiety of the nucleotide, have been tested for incorporation with Pol θ. Wild type Pol θ enzyme show little to medium incorporation rate of these permanent labeled base-modified nucleotides. However, incorporation of modified reversible terminator nucleotides is not feasible with wild type Pol θ. In particular Pol θ is unable to incorporate 3'O-reversible modified nucleotides.

The present invention relates to modified family A polymerases able to incorporate modified reversible terminator nucleotides.

In the context of the invention, "modified family A DNA polymerases", "modified family A polymerases", "variants of family A DNA polymerases" and "variants of family A polymerases" refer to enzymes that share at least 25% identity with the amino acid sequence of a family A polymerase and comprises at least the amino acid sequence as set forth in SEQ ID No2 excepting at least one amino acid residue mutation. Preferably, the variant of family A DNA polymerase is a variant of a Pol θ polymerase sharing at least 40% identity with SEQ ID No1. Alternatively or in addition, the 3D structure of the variant of a Pol θ polymerase shares at least 60% identity with the 3D structure of human Pol θ polymerase. As used herein, such 3D structure identity means that at least 60% of the amino acid residues of the variant have same position and spatial conformation as amino acid residues in the 3D structure of human Pol θ polymerase.

Herein, the terms "peptide", "polypeptide", "protein", "enzyme", refer to a chain of amino acids linked by peptide bonds, regardless of the number of amino acids forming said chain. The amino acids are herein represented by their one-letter or three-letters code according to the following nomenclature: A: alanine (Ala); C: cysteine (Cys); D: aspartic acid (Asp); E: glutamic acid (Glu); F: phenylalanine (Phe); G: glycine (Gly); H: histidine (His); I: isoleucine (Ile); K: lysine (Lys); L: leucine (Leu); M: methionine (Met); N: asparagine (Asn); P: proline (Pro); Q: glutamine (Gln); R: arginine (Arg); S: serine (Ser); T: threonine (Thr); V: valine (Val); W: tryptophan (Trp) and Y: tyrosine (Tyr).

Accordingly, the terms "mutant" and "variant" may be used interchangeably to refer to polypeptides derived from SEQ ID No2 and comprising a modification or an alteration, i.e., a substitution, insertion, and/or deletion, at one or more (e.g., several) positions and having both a polymerase activity without template and ability to incorporate. The variants may be obtained by various techniques well known in the art. In particular, examples of techniques for altering the DNA sequence encoding the wild-type protein, include, but are not limited to, site-directed mutagenesis, random mutagenesis and synthetic oligonucleotide construction. Mutagenesis activities consists in deleting, inserting or substituting one or several amino-acids in the sequence of the polymerase. Targeted amino-acids could be concomitant or distributed along the whole sequence of the polymerase. Particular motif or structural feature could be targeted for example.

The term "modification" or "alteration" as used herein in relation to a position or amino acid means that the amino acid in the particular position has been modified compared to the amino acid of the wild-type protein.

A "substitution" means that an amino acid residue is replaced by another amino acid residue. Preferably, the term "substitution" refers to the replacement of an amino acid residue by another selected from the naturally-occurring standard 20 amino acid residues, rare naturally occurring amino acid residues (e.g. hydroxyproline, hydroxylysine, allohydroxylysine, 6-N-methylysine, N-ethylglycine, N-methylglycine, N-ethylasparagine, allo-isoleucine, N-methylisoleucine, N-methylvaline, pyroglutamine, aminobutyric acid, ornithine, norleucine, norvaline), and non-naturally occurring amino acid residue, often made synthetically, (e.g. cyclohexyl-alanine). Preferably, the term "substitution" refers to the replacement of an amino acid residue by another selected from the naturally-occurring standard 20 amino acid residues (G, P, A, V, L, I, M, C, F, Y, W, H, K, R, Q, N, E, D, S and T). The sign "+" indicates a combination of substitutions. In the present document, the following terminology is used to designate a substitution: L2382A denotes that amino acid residue (Leucine, L) at position 2382 of the parent sequence is changed to an Alanine (A). A1321V/I/M denotes that amino acid residue (Alanine, A) at position 1321 of the parent sequence is substituted by one of the following amino acids: Valine (V), Isoleucine (I), or Methionine (M). The substitution can be a conservative or non-conservative substitution. Examples of conservative substitutions are within the groups of basic amino acids (arginine, lysine and histidine), acidic amino acids (glutamic acid and aspartic acid), polar amino acids (glutamine, asparagine and threonine), hydrophobic amino acids (methionine, leucine, isoleucine, cysteine and valine), aromatic amino acids (phenylalanine, tryptophan and tyrosine), and small amino acids (glycine, alanine and serine).

The term "deletion", used in relation to an amino acid, means that the amino acid has been removed or is absent.

The term "insertion" means that one or more amino acids have been added.

Unless otherwise specified, the positions disclosed in the present application are numbered by reference to the amino acid sequence set forth in SEQ ID No1.

As used herein, the term "sequence identity" or "identity" refers to the number (or fraction expressed as a percentage %) of matches (identical amino acid residues) between two polypeptide sequences. The sequence identity is determined by comparing the sequences when aligned so as to maximize overlap and identity while minimizing sequence gaps. In particular, sequence identity may be determined using any of a number of mathematical global or local alignment algorithms, depending on the length of the two sequences. Sequences of similar lengths are preferably aligned using a global alignment algorithms (e.g. Needleman and Wunsch algorithm; Needleman and Wunsch, 1970) which aligns the sequences optimally over the entire length, while sequences of substantially different lengths are preferably aligned using a local alignment algorithm (e.g. Smith and Waterman algorithm (Smith and Waterman, 1981) or Altschul algorithm (Altschul et al., 1997; Altschul et al., 2005)). Alignment for purposes of determining percent amino acid sequence identity can be achieved in various ways that are within the skill in the art, for instance, using publicly available computer software available on internet web sites such as blast.ncbi.nlm.nih.gov/or www.ebi.ac.uk/Tools/emboss/). Those skilled in the art can determine appropriate parameters for measuring alignment, including any algorithms needed to achieve maximal alignment over the full length of the sequences being compared. For purposes herein, % amino acid sequence identity values refers to values generated using the pair wise sequence alignment program EMBOSS Needle that creates an optimal global alignment of two sequences using the Needleman-Wunsch algorithm, wherein all search parameters are set to default values, i.e. Scoring matrix=BLOSUM62, Gap open=10, Gap extend=0.5, End gap penalty=false, End gap open=10 and End gap extend=0.5.

Reversible Terminator Modified Nucleotides

In one embodiment, the invention relates to modified Pol θ polymerase able to incorporate modified reversible terminator nucleotides. In a particular embodiment, the invention relates to modified Pol θ polymerases able to incorporate modified 3'O-reversible nucleotides.

In the context of the invention, the expression "Reversible Terminator Modified Nucleotide" refers to a molecule containing a nucleoside (i.e. a base attached to a deoxyribose or ribose sugar molecule) bound to three phosphate groups which has at least one additional group on one of its extremity: 2', 3', 5' or base. Said additional group blocks further addition of nucleotides by preventing the formation of any phosphodiester bond (3'O-modification, 2' or 2'O modifications) or by sterically preventing the polymerase to attached to any nucleic acid fragments that comprises on its 3' extremity such modified reversible terminator nucleotide (5' or base modification). Furthermore, said additional group has a reversible nature allowing that group to be removed through a specific cleaving reaction.

Nucleosides or nucleotide triphosphates include deoxyadenosine triphosphate (dATP), deoxyguanosine triphosphate (dGTP), deoxycytidine triphosphate (dCTP) or deoxythymidine triphosphate (dTTP) for examples of nucleotide containing deoxyribose. Adenosine triphosphate (ATP), guanosine triphosphate (GTP), cytidine triphosphate (CTP) or uridine triphosphate (UTP) are further examples of nucleotide triphosphates containing ribose. Other types of nucleosides may be bound to three phosphates to form nucleotide triphosphates, such as naturally occurring modified nucleosides and artificial nucleosides.

In a particular embodiment, the modified reversible terminator nucleotide is a 3'O modified nucleotide, which comprises a group attached to the 3' end of the nucleotide triphosphate to prevent further nucleotide addition. Said group could have diverse chemical natures, such as azidomethyl, aminoxy, and allyl.

In further particular embodiment, 3'O modified nucleotide refers to nucleotide triphosphate bearing at the 3' extremity either a 3'-O-methyl, 3'-azido, 3'-O-azidomethyl, 3'-O-amino, 3'-aminoxy or 3'-0-allyl group. In a further embodiment, the 3'-blocked nucleotide triphosphate is blocked by either a 3'-0-azidomethyl, 3'-aminoxy or 3'-0-allyl group. In other embodiments, 3'O modified nucleotide refers to nucleotide triphosphate bearing at the 3' extremity either esters, ethers, carbonitriles, phosphates, carbonates, carbamates, hydroxylamine, borates, nitrates, sugars, phosphoramide, phosphoramidates, phenylsulfenates, sulfates, sulfones and amino acids.

In further particular embodiment, 3'O modified nucleotide refers to a nucleotide triphosphate having a terminator effector modifying group such as the ones describe in WO2016034807 incorporated herein by references in its entirety.

According to a first aspect, the invention relates to variants of family A DNA polymerases which exhibit an increased affinity for modified reversible terminator nucleotides, and thereby an increased ability to incorporate such modified nucleotide in a nucleic acid sequence during nucleic acid synthesis, as compared to wild type family A DNA polymerase.

According to a particular aspect, the invention relates to variants of Pol θ polymerases which exhibit an increased affinity for modified reversible terminator nucleotides, and thereby an increased ability to incorporate such modified nucleotide in a nucleic acid sequence during nucleic acid synthesis, as compared to wild type Pol θ polymerase. Particularly, the invention relates to variants of Pol θ polymerases with increased incorporation ability of 3'O-modified nucleotides.

According to another particular aspect, the invention relates to variants of family A DNA polymerases capable of quantitative incorporation of modified reversible terminator nucleotides, more preferably of variants of Pol θ polymerases. Preferably, modified reversible terminator nucleotides are 3'O-modified nucleotides.

According to another aspect, the invention relates to variants of Family A DNA Polymerase able to work with reversible terminator modified nucleotides in a nucleic acids enzymatic synthesis process, and having the ability to produce long length of nucleic acid molecules or derivative of nucleic acids molecules; in particular embodiments, of Pol θ polymerases; in further particular embodiments, of 3'O-modified nucleotides.

Depending on the mutation or the combination of mutations, the polymerase will display improved ability to incorporate 3'O modified nucleotides to a growing single stranded chain of nucleic acids. Such improved property finds use in the de novo synthesis of nucleic acids.

Variants of Family A DNA Polymerase

According to the invention, the variants of Family A DNA Polymerase are capable of synthesizing extremely long fragments of nucleic acid molecules before dissociation. Extremely long fragments of nucleic acid molecule having length of more than 50, 100, 200, 300, 400, 500, 600, 700, 800, 900, 1 000, 2 000, 3 000, 4 000, 5 000, 6 000, 7 000, 8 000, 9 000, 10 000, 15 000, 20 000, 30 000, 40 000, 50 000 or 100 000 nucleotides.

It is known that A Family polymerases could be composed by several distinct domains. Pol θ polymerases possesses 3 different domains: helicase domain, central domain and polymerase domain (see table 1 below). The helicase domain has an enzymatic activity related to helicase activity, an ATP consumption activity and nucleic acid strand affinity.

The central domain seams to lake of particular specific enzymatic activity. The polymerase domain possesses an enzymatic activity related to nucleotide polymerization and nucleic acid strand affinity.

In a particular embodiment, the present invention contemplates modified Pol θ polymerases baring any mutation or combination previously described applicate to the whole enzyme composed of the three domains: helicase, central and polymerase domain.

In an alternative embodiment, the present invention contemplates modified Pol θ polymerases baring any mutation or combination previously described applicate to the following subdomains: helicase and polymerase domain. In particular, the helicase and polymerase domain could be separated by any amino acid linker, including non-natural amino acids, of any length between 1 and 1000 amino acids. Said linker could be composed in its N-terminal and C-terminal extremity by part or full central domain sequence linked respectively to the helicase and polymerase domains.

Preferably, the variant of the invention comprises at least the amino acid sequence as set forth in SEQ ID No2, except at least one mutation of an amino acid.

SEQ ID No2 corresponds to the amino acid residues 2327 to 2339 of SEQ ID No1, which is the amino acid sequence of the human Pol θ (Pol Theta). Pol θ comprises several domains, as listed in table 1 below, wherein the amino acid positions are numbered by reference to the amino acid sequence set forth in SEQ ID No1.

TABLE 1

Pol Theta Domains

| Pol Theta Domains | Amino acid positions |
| --- | --- |
| Helicase domain | 1 to 899 |
| Central domain | 900 to 1818 |
| Polymerase domain | 1819 to 2590 |
| Insert 1 | 2149 to 2170 |
| Insert 2 | 2263 to 2314 |
| Insert 3 | 2496 to 2530 |

According to the invention, the variant (i) comprises the amino acid sequence set forth in SEQ ID No2 or a functionally equivalent sequence, with at least one amino acid mutation at any one of the amino acid residue as compared to SEQ ID No2, (ii) is able to synthesize a nucleic acid fragment without template and (iii) is able to incorporate a reversible modified terminator nucleotide during the nucleic acid fragment synthesis.

The variants of the present invention are described according to their mutations on specific residues whose positions are determined by alignment with or reference to the enzymatic sequence SEQ ID No1, which corresponds to the amino acid sequence of the human Pol θ. In the context of the invention, any variant bearing these same mutations on functionally equivalent residues is also part of the invention.

By "functionally equivalent residue" is meant a residue in a sequence of a DNA polymerase of Pol θ of sequence homologous to SEQ ID No1 and having an identical functional role. Functionally equivalent residues are identified by using sequence alignments, for example, using the Mutalin line alignment software (http://multalin.toulouse.inra.fr/multalin/multalin.html; 1988, Nucl. Acids Res., 16 (22), 10881-10890). After alignment, the functionally equivalent residues are at homologous positions on the different sequences considered. Sequence alignments and identification of functionally equivalent residues may be between any of the polymerases of the Polymerase A family, and preferably any Pol θ and their natural variants, including interspecies.

In the context of the invention, "functional fragment" refers to a DNA polymerase fragment of Family A exhibiting DNA polymerase activity. The fragment may comprise 500, 600, 700 or more consecutive amino acids of a polymerase of Family A. Preferably, the fragment comprises at least 770 consecutive amino acids of the polymerase domain of said enzyme. "Functional equivalent sequence" refers to a sequence homologous to the disclosed sequence and having an identical functional role.

SEQ ID No3

In a particular embodiment, the variant comprises at least a mutated amino acid in the amino acid sequence as set forth in SEQ ID No3 (DYSQLELRIL), or functional equivalent sequence, in a homologous Pol θ sequence.

SEQ ID No3 constitutes a succession of amino acids in direct interaction with the incoming nucleotide, in particular with the 3' and 2' extremity of the sugar moiety of the nucleotide. The amino acid residues of SEQ ID No3 are especially close to the 3' and 2' extremity of the sugar moiety of the nucleotide and are well conserved across different species. Side chains of amino acid residues of SEQ ID No3 form a steric gate for nucleotide having a bulkier size than natural nucleotides.

In a particular embodiment, the variant comprises one or more substitutions of amino acid residues of SEQ ID No3. Such residues are adjacent (i.e. successive) or distributed across SEQ ID No3. Such substitutions are identical or different across the targeted residues.

In a particular embodiment, the variant comprises one or more deletions of amino acid residues of SEQ ID No3. Such residues are adjacent (i.e. successive) or distributed across SEQ ID No3.

In a particular embodiment, the variant comprises one or more additions of amino acid residues in one or more locations of SEQ ID No3. Such locations are adjacent (i.e. successive) or distributed across SEQ ID No3.

In a particular embodiment, the substitution is selected from the substitutions listed in table 2 below.

TABLE 2

Preferred substitutions in SEQ ID No 3

| Natural Amino Acid | Residue Position | Substitution |
| --- | --- | --- |
| D | 2330 | E; R; H; K; T; V; A; G |
| Y | 2331 | F; W; P; H; M; L; V; A |
| S | 2332 | T; N; Q; V; A; G |
| Q | 2333 | N; T; S; A; G; V |
| L | 2334 | M; E; N; F; K; D; A; G |
| E | 2335 | G; A; N; T; S; D |
| L | 2336 | M; E; N; F; K; D; A; G |
| R | 2337 | H; K; D; E; A; G; M; F |
| I | 2338 | V; A; G; L; T; S; D; K; M |
| L | 2339 | M; E; N; F; K; D; A; G; I |

SEQ ID No4

In a particular embodiment, the variant comprises at least a mutated amino acid in the amino acid sequence as set forth in SEQ ID No4 (PGGSILAA), or functional equivalent sequence, in a homologous Pol θ sequence.

SEQ ID No4 constitutes a structural feature orienting the β-sheet strands of the palm domain of the polymerase. The palm domain of the polymerase is closely interacting with the incoming nucleotide. Altering Motif B sequence will have an influence on palm conformation and lead to a wider catalytic pocket for accepting bulkier nucleotides. Introducing more flexibility or new strand orientation by altering SEQ ID No4 will change palm domain capacity to accept different size of nucleotides.

In a particular embodiment, the variant comprises one or more substitutions of amino acid residues of SEQ ID No4. Such residues are adjacent (i.e. successive) or distributed across SEQ ID No4. Such substitutions are identical or different across the targeted residues.

In a particular embodiment, the variant comprises one or more deletions of amino acid residues of SEQ ID No4. Such residues are adjacent (i.e. successive) or distributed across SEQ ID No4.

In a particular embodiment, the variant comprises one or more additions of amino acid residues in one or more locations of SEQ ID No4. Such locations are adjacent (i.e. successive) or distributed across SEQ ID No4.

In a particular embodiment, the substitution is selected from the substitutions listed in table 3 below.

TABLE 3

Preferred substitutions in SEQ ID No 4

| Natural Amino Acid | Residue Position | Substitution |
| --- | --- | --- |
| P | 2322 | A; V; I; L; G; C |
| G | 2323 | C; P; A; V; K; D |
| G | 2324 | C; P; A; V; K; D |
| S | 2325 | L; N; M; V; T; A; G; D; K |
| I | 2326 | V; A; G; L; T; S; D; K; M |
| L | 2327 | M; E; N; F; K; D; A; G; I; V |
| A | 2328 | V; T; G |
| A | 2329 | V; T; G |

SEQ ID No5

In a particular embodiment, the variant comprises at least a mutated amino acid in the amino acid sequence as set forth in SEQ ID No5 (DDLRQQAKQICYGIIY), or functional equivalent sequence, in a homologous Pol θ sequence, excluding the following substitution mutation: Q2384A.

SEQ ID No5 constitutes a succession of amino acids in direct interaction with the pyrophosphate moiety of the incoming nucleotide. It has been shown, that altering the natural interaction between the enzyme residues and the pyrophosphate moiety of the nucleotide leads to modification of the nucleotide orientation while conserving the catalytic efficiency of the polymerase enzyme. The result of such alteration is thus a modified polymerase able to add a nucleotide or modified nucleotide in a different orientation, compared to natural orientation of the nucleotide in the wild type enzyme, with same or improved efficiency. The difference in nucleotide orientation can be significantly advantageous for accommodating bulkier nucleotides or nucleotide with a particular modification at a specific extremity such as 3'O-modified nucleotides for example. The Y2391 residue interacts with both 3' and 2' extremity of the sugar moiety of the nucleotide. Altering Y2391 will lead to modification of the space allocated for the nucleotide in the catalytic pocket, especially in the local 3' and 2' extremity of the nucleotide. In particular bulkier 3' or 2' modifying groups bared by modified nucleotides could be process by enzyme having an altered Y2391.

In a particular embodiment, the variant comprises one or more substitutions of amino acid residues of SEQ ID No5. Such residues are adjacent (i.e. successive) or distributed across SEQ ID No5. Such substitutions are identical or different across the targeted residues.

In a particular embodiment, the variant comprises one or more deletions of amino acid residues of SEQ ID No5. Such residues are adjacent (i.e. successive) or distributed across SEQ ID No5.

In a particular embodiment, the variant comprises one or more additions of amino acid residues in one or more locations of SEQ ID No5. Such locations are adjacent (i.e. successive) or distributed across SEQ ID No5.

In particular embodiments, the substitution is selected from the substitutions listed in table 4 below.

TABLE 4

Preferred substitutions in SEQ ID No 5

| Natural Amino Acid | Residue Position | Substitution | Excluded Substitution |
| --- | --- | --- | --- |
| D | 2376 | E; R; H; K; T; V; A; G; N | |
| D | 2377 | E; R; H; K; T; V; A; G; N | |
| L | 2378 | M; E; N; F; K; D; A; G; I | |
| R | 2379 | H; K; D; E; A; G; M; F | |
| Q | 2380 | N; T; S; A; G; V | |
| Q | 2381 | N; T; S; A; G; V | |
| A | 2382 | V; T; G | |
| K | 2383 | R; H; D; E; Q; N; C; A; G; S; T | |
| Q | 2384 | N; T; S; G; V | A |
| I | 2385 | V; A; G; L; T; S; D; K; M | |
| C | 2386 | G; P; A; V; S; N; Q; D; K | |
| Y | 2387 | F; W; P; H; M; L; V; A | |
| G | 2388 | C; P; A; V; K; D | |
| I | 2389 | V; A; G; L; T; S; D; K; M | |
| I | 2390 | V; A; G; L; T; S; D; K; M | |
| Y | 2391 | F; W; P; H; M; L; V; A | |

SEQ ID No6

In a particular embodiment, the variant comprises at least a mutated amino acid in the amino acid sequence as set forth in SEQ ID No6 (EWRRIT), or functional equivalent sequence, in a homologous Pol θ sequence excluding the following substitution mutation: R2202A.

SEQ ID No6 constitutes a succession of amino acids in direct interaction with the different residues that constitute the nucleic acid growing chain. Altering the amino acids of SEQ ID No6 leads to changes in primer orientation that enable increase of the catalytic pocket volume globally or locally. Such changes in catalytic pocket volume could have an impact on enzyme capacity to accept bulkier nucleotide or nucleotide with a particular modification. Modifying the interaction with the nucleic acid growing chain also leads to modification of the affinity of the enzyme for the primer strand. Such affinity modification impacts enzyme/nucleic acid dissociation characteristics including, but not limited to, dissociation strength and dissociation characteristic time. As a result, altering residues of SEQ ID No6 changes enzyme affinity for different type of nucleic acid molecules having different structures, such as DNA, RNA, DNA with epigenetic modifications, RNA with epigenetic modifications or XNA as examples.

In a particular embodiment, the variant comprises one or more substitutions of amino acid residues of SEQ ID No6. Such residues are adjacent (i.e. successive) or distributed across SEQ ID No6. Such substitutions are identical or different across the targeted residues.

In a particular embodiment, the variant comprises one or more deletions of amino acid residues of SEQ ID No6. Such residues are adjacent (i.e. successive) or distributed across SEQ ID No6.

In a particular embodiment, the variant comprises one or more additions of amino acid residues in one or more locations of SEQ ID No6. Such locations are adjacent (i.e. successive) or distributed across SEQ ID No6.

In particular embodiments, the substitution is selected from the substitutions listed in table 5 below.

TABLE 5

Preferred substitutions in SEQ ID No 6

| Natural Amino Acid | Residue Position | Substitution | Excluded Substitution |
|---|---|---|---|
| E | 2199 | G; A; N; T; S; D; K | |
| W | 2200 | Y; F; P; L; I; V; A; G; E | |
| R | 2201 | H; K; D; E; G; M; F; S; P | |
| R | 2202 | H; K; D; E; G; M; F; S; P | A |
| I | 2203 | V; A; G; L; T; S; D; K; M; P | |
| T | 2204 | S; N; Q; C; G; M; K; D | |

Catalytic Triad

In a particular embodiment, the variant comprises at least one amino acid mutation, preferably of at least two mutations, more preferably three mutation at position(s) corresponding to residues selected from D2330, D2540 or E2541, or residues functionally equivalent, excluding D2540N/A or E2541Q/A, wherein the positions are numbered by reference to the amino acid sequence set forth in SEQ ID No1.

The catalytic triad residues are the residues directly involved in the phosphodiester condensation reaction performed by the polymerases. Altering those residues modifies the overall activity of the polymerase enzyme. Alteration of one or more of the catalytic triad residues in association with the use of modified nucleotide advantageously lead to increased incorporation rate of said modified nucleotide due to conformational adaptations sufficient to deal with nucleotide modifications. Some specific substitutions such as D2540N, D2540A, E2541Q or E2541A, alone or in combination are known to suppress the activity of the polymerase. As a result, these substitutions are excluded from the scope of the present invention.

In a particular embodiment, the variant comprises one or more substitutions of amino acid residues selected from D2330, D2540 or E2541. Such substitutions are identical or different across the targeted residues. In a preferred embodiment, the variant comprises a substitution at the amino acid position D2330, D2540 and E2541.

In a particular embodiment, the variant comprises one or more deletions of amino acid residues comprises one or more substitutions of amino acid residues selected from D2330, D2540 or E2541.

In a particular embodiment, the variant comprises one or more additions of amino acid residues before or after one or more of amino acid residues selected from D2330, D2540 or E2541.

In particular embodiments, the substitutions are selected from table 6

TABLE 6

Preferred substitutions in the catalytic triad

| Natural Amino Acid | Residue Position | Substitution | Excluded Substitution |
|---|---|---|---|
| D | 2330 | E; R; H; K; T; V; A; G | |
| D | 2540 | E; K; R; H; Q; S; T; C | N; A |
| E | 2541 | D; R; H; K; N; S; T; C | Q; A |

Other Residues of Interest

In an embodiment of the invention, the variant comprises at least a mutation in one of the following residues composed by K2181, R2315, F2359, or A2477, or a functional equivalent of those residues in a homologous Pol θ sequence; excluding the following substitution mutation: K2181A and the following residue deletion: Δ2315.

The K2181 residue interacts with the nucleic acid growing chain. Effect of alteration of this residue is similar to alteration in residues of SEQ ID No6. The substitution K2181A alone or in combination is known to reduce the activity of the polymerase. The F2315 residue interacts with the ultimate nucleotide of the nucleic acid growing chain. Effect of alteration of this residue is similar to alteration in residues of SEQ ID No6. The deletion of R2315 residue alone or in combination is known to reduce the activity of the polymerase. The F2359 residue acts as a satirical gate for nucleotide to enter the catalytic pocket. Altering F2359 leads to modification of the association characteristics between the enzyme and the nucleotide. In particular wider space for modified nucleotide to enter could be obtained by altering F2359. The A2477 residue is implicated in the overall size of the catalytic pocket. Altering A2477 leads to modification of the space allocated for the nucleotide in the catalytic pocket. In particular bulkier modified nucleotides could be processed by enzyme having an altered A2477.

In a particular embodiment, the variant comprises one or more substitutions of amino acid residues selected from K2181, R2315, F2359, or A2477. Such substitutions are identical or different across the targeted residues. In a preferred embodiment, the variant comprises substitutions at all the amino acid positions K2181, R2315, F2359, and A2477.

In a particular embodiment, the variant comprises one or more deletions of amino acid residues comprises one or more substitutions of amino acid residues selected from K2181, R2315, F2359, or A2477.

In a particular embodiment, the variant comprises one or more additions of amino acid residues before or after one or more of amino acid residues selected from K2181, R2315, F2359, or A2477.

In particular embodiments, the substitutions are selected from the table 7.

TABLE 7

Preferred substitutions

| Natural Amino Acid | Residue Position | Substitution | Excluded Substitution |
|---|---|---|---|
| K | 2181 | R; H; D; E; Q; N; C; G; S; T | A |
| R | 2315 | H; K; D; E; A; G; M; F | |
| F | 2359 | M; L; I; V; A; G; P; T; K; D | |
| A | 2477 | V; T; G | |

Steric Enlargement of Catalytic Pocket

Structural 3D models of Family A polymerases provide useful information about nucleotide conformation, catalytic pocket size and steric hindrance of side chains of specific residues. Identification of residues based on their special configuration and interactions with the nucleotide present inside the catalytic pocket is critical.

In a particular embodiment of the invention, the variant comprises at least one amino acid mutation of a residue having side chain groups positioned within 15 Å, 12 Å, 10 Å, or 6 Å of a 3'O extremity of a nucleotide, or residue functionally equivalent.

In a particular embodiment, the present invention contemplates modified Pol θ polymerases in one or several of the residues within 0.6 nm (6 Å) of the 3'O extremity of the nucleotide.

In a particular embodiment, the present invention contemplates modified Pol θ polymerases in one or several of the residues within 1.0 nm (10 Å) of the 3'O extremity of the nucleotide.

In a particular embodiment, the present invention contemplates modified Pol θ polymerases in one or several of the residues within 1.2 nm (12 Å) of the 3'O extremity of the nucleotide.

In a particular embodiment, the present invention contemplates modified Pol θ polymerases in one or several of the residues within 1.5 nm (15 Å) of the 3'O extremity of the nucleotide.

More particularly, according to a particular embodiment, the present invention contemplates modified Pol θ polymerases in one or several of the residues listed in table 8 below.

TABLE 8

Residue positions at 6, 10, 10, and 15 Å

| Residue | Position | Distance (Å) |
|---|---|---|
| Q | 2333 | 6 |
| E | 2335 | 6 |
| Y | 2387 | 6 |
| D | 2540 | 6 |
| R | 2241 | 10 |
| D | 2330 | 10 |
| Y | 2331 | 10 |
| S | 2332 | 10 |
| L | 2334 | 10 |
| L | 2336 | 10 |
| R | 2337 | 10 |
| I | 2338 | 10 |
| F | 2359 | 10 |
| Q | 2380 | 10 |
| K | 2383 | 10 |
| G | 2388 | 10 |
| I | 2390 | 10 |
| Y | 2391 | 10 |
| V | 2473 | 10 |
| Q | 2474 | 10 |
| A | 2477 | 10 |
| A | 2478 | 10 |
| V | 2481 | 10 |
| H | 2539 | 10 |
| T | 2239 | 12 |
| R | 2254 | 12 |
| L | 2339 | 12 |
| L | 2352 | 12 |
| D | 2357 | 12 |
| R | 2379 | 12 |
| Q | 2384 | 12 |
| C | 2386 | 12 |
| I | 2469 | 12 |
| N | 2470 | 12 |
| G | 2475 | 12 |
| S | 2476 | 12 |
| I | 2480 | 12 |
| Q | 2537 | 12 |
| L | 2538 | 12 |
| E | 2541 | 12 |
| M | 2562 | 12 |
| L | 2572 | 12 |
| K | 2575 | 12 |
| T | 2237 | 15 |
| G | 2240 | 15 |
| I | 2242 | 15 |
| T | 2243 | 15 |
| Q | 2250 | 15 |
| R | 2315 | 15 |

TABLE 8-continued

Residue positions at 6, 10, 10, and 15 Å

| Residue | Position | Distance (Å) |
|---|---|---|
| A | 2329 | 15 |
| A | 2340 | 15 |
| H | 2341 | 15 |
| L | 2342 | 15 |
| L | 2348 | 15 |
| G | 2355 | 15 |
| V | 2358 | 15 |
| I | 2362 | 15 |
| Q | 2381 | 15 |
| A | 2382 | 15 |
| I | 2385 | 15 |
| I | 2389 | 15 |
| G | 2392 | 15 |
| M | 2393 | 15 |
| Q | 2401 | 15 |
| I | 2423 | 15 |
| F | 2426 | 15 |
| M | 2427 | 15 |
| T | 2442 | 15 |
| I | 2443 | 15 |
| R | 2446 | 15 |
| T | 2471 | 15 |
| I | 2472 | 15 |
| D | 2479 | 15 |
| A | 2484 | 15 |
| L | 2536 | 15 |
| L | 2542 | 15 |
| L | 2568 | 15 |
| V | 2570 | 15 |
| K | 2573 | 15 |
| V | 2574 | 15 |
| K | 2577 | 15 |
| W | 2582 | 15 |

Mutations and Combination of Mutations

The present invention relates to modified Pol θ polymerases with increased incorporation rate for reversible terminator modified nucleotides. It will be understood that the present invention contemplates any combinations of mutations listed below. In particular combination of two or more substitutions, combination of one or more substitution with residue deletion or addition or both, combination of two or more deletion, combination of deletion and addition, and combination of two of more additions.

It is therefore an object of the invention to provide variants of Pol Theta, which comprise at least a substitution or combination of substitutions as listed in table 9, wherein the positions are numbered by reference to the amino acid sequence set forth in SEQ ID No1.

TABLE 9

Mutations and combination of substitutions

| Name | Mutations |
|---|---|
| DS1 | L2336A + A2328V + Y2387F + E2335G + P2322A + L2334M |
| DS2 | L2336A + A2328V + Y2387F + E2335G + P2322A + L2334G |
| DS3 | L2336A + A2328V + Y2387F + E2335G + P2322A |
| DS4 | L2336A + A2328V + Y2387F + E2335G + P2322V + L2334M |
| DS5 | L2336A + A2328V + Y2387F + E2335G + P2322V + L2334G |
| DS6 | L2336A + A2328V + Y2387F + E2335G + P2322V |
| DS7 | L2336A + A2328V + Y2387F + E2335G + L2334M |
| DS8 | L2336A + A2328V + Y2387F + E2335G + L2334G |
| DS9 | L2336A + A2328V + Y2387F + E2335G |
| DS10 | L2336A + A2328V + Y2387F + E2335A + P2322A + L2334M |
| DS11 | L2336A + A2328V + Y2387F + E2335A + P2322A + L2334G |
| DS12 | L2336A + A2328V + Y2387F + E2335A + P2322A |
| DS13 | L2336A + A2328V + Y2387F + E2335A + P2322V + L2334M |
| DS14 | L2336A + A2328V + Y2387F + E2335A + P2322V + L2334G |

TABLE 9-continued

Mutations and combination of substitutions

| Name | Mutations |
|---|---|
| DS15 | L2336A + A2328V + Y2387F + E2335A + P2322V |
| DS16 | L2336A + A2328V + Y2387F + E2335A + L2334M |
| DS17 | L2336A + A2328V + Y2387F + E2335A + L2334G |
| DS18 | L2336A + A2328V + Y2387F + E2335A |
| DS19 | L2336A + A2328V + Y2387F + P2322A + L2334M |
| DS20 | L2336A + A2328V + Y2387F + P2322A + L2334G |
| DS21 | L2336A + A2328V + Y2387F + P2322A |
| DS22 | L2336A + A2328V + Y2387F + P2322V + L2334M |
| DS23 | L2336A + A2328V + Y2387F + P2322V + L2334G |
| DS24 | L2336A + A2328V + Y2387F + P2322V |
| DS25 | L2336A + A2328V + Y2387F + L2334M |
| DS26 | L2336A + A2328V + Y2387F + L2334G |
| DS27 | L2336A + A2328V + Y2387F |
| DS28 | L2336A + A2328V + E2335G + P2322A + L2334M |
| DS29 | L2336A + A2328V + E2335G + P2322A + L2334G |
| DS30 | L2336A + A2328V + E2335G + P2322A |
| DS31 | L2336A + A2328V + E2335G + P2322V + L2334M |
| DS32 | L2336A + A2328V + E2335G + P2322V + L2334G |
| DS33 | L2336A + A2328V + E2335G + P2322V |
| DS34 | L2336A + A2328V + E2335G + L2334M |
| DS35 | L2336A + A2328V + E2335G + L2334G |
| DS36 | L2336A + A2328V + E2335G |
| DS37 | L2336A + A2328V + E2335A + P2322A + L2334M |
| DS38 | L2336A + A2328V + E2335A + P2322A + L2334G |
| DS39 | L2336A + A2328V + E2335A + P2322A |
| DS40 | L2336A + A2328V + E2335A + P2322V + L2334M |
| DS41 | L2336A + A2328V + E2335A + P2322V + L2334G |
| DS42 | L2336A + A2328V + E2335A + P2322V |
| DS43 | L2336A + A2328V + E2335A + L2334M |
| DS44 | L2336A + A2328V + E2335A + L2334G |
| DS45 | L2336A + A2328V + E2335A |
| DS46 | L2336A + A2328V + P2322A + L2334M |
| DS47 | L2336A + A2328V + P2322A + L2334G |
| DS48 | L2336A + A2328V + P2322A |
| DS49 | L2336A + A2328V + P2322V + L2334M |
| DS50 | L2336A + A2328V + P2322V + L2334G |
| DS51 | L2336A + A2328V + P2322V |
| DS52 | L2336A + A2328V + L2334M |
| DS53 | L2336A + A2328V + L2334G |
| DS54 | L2336A + A2328V |
| DS55 | L2336A + Y2387F + E2335G + P2322A + L2334M |
| DS56 | L2336A + Y2387F + E2335G + P2322A + L2334G |
| DS57 | L2336A + Y2387F + E2335G + P2322A |
| DS58 | L2336A + Y2387F + E2335G + P2322V + L2334M |
| DS59 | L2336A + Y2387F + E2335G + P2322V + L2334G |
| DS60 | L2336A + Y2387F + E2335G + P2322V |
| DS61 | L2336A + Y2387F + E2335G + L2334M |
| DS62 | L2336A + Y2387F + E2335G + L2334G |
| DS63 | L2336A + Y2387F + E2335G |
| DS64 | L2336A + Y2387F + E2335A + P2322A + L2334M |
| DS65 | L2336A + Y2387F + E2335A + P2322A + L2334G |
| DS66 | L2336A + Y2387F + E2335A + P2322A |
| DS67 | L2336A + Y2387F + E2335A + P2322V + L2334M |
| DS68 | L2336A + Y2387F + E2335A + P2322V + L2334G |
| DS69 | L2336A + Y2387F + E2335A + P2322V |
| DS70 | L2336A + Y2387F + E2335A + L2334M |
| DS71 | L2336A + Y2387F + E2335A + L2334G |
| DS72 | L2336A + Y2387F + E2335A |
| DS73 | L2336A + Y2387F + P2322A + L2334M |
| DS74 | L2336A + Y2387F + P2322A + L2334G |
| DS75 | L2336A + Y2387F + P2322A |
| DS76 | L2336A + Y2387F + P2322V + L2334M |
| DS77 | L2336A + Y2387F + P2322V + L2334G |
| DS78 | L2336A + Y2387F + P2322V |
| DS79 | L2336A + Y2387F + L2334M |
| DS80 | L2336A + Y2387F + L2334G |
| DS81 | L2336A + Y2387F |
| DS82 | L2336A + E2335G + P2322A + L2334M |
| DS83 | L2336A + E2335G + P2322A + L2334G |
| DS84 | L2336A + E2335G + P2322A |
| DS85 | L2336A + E2335G + P2322V + L2334M |
| DS86 | L2336A + E2335G + P2322V + L2334G |
| DS87 | L2336A + E2335G + P2322V |
| DS88 | L2336A + E2335G + L2334M |
| DS89 | L2336A + E2335G + L2334G |
| DS90 | L2336A + E2335G |
| DS91 | L2336A + E2335A + P2322A + L2334M |
| DS92 | L2336A + E2335A + P2322A + L2334G |
| DS93 | L2336A + E2335A + P2322A |
| DS94 | L2336A + E2335A + P2322V + L2334M |
| DS95 | L2336A + E2335A + P2322V + L2334G |
| DS96 | L2336A + E2335A + P2322V |
| DS97 | L2336A + E2335A + L2334M |
| DS98 | L2336A + E2335A + L2334G |
| DS99 | L2336A + E2335A |
| DS100 | L2336A + P2322A + L2334M |
| DS101 | L2336A + P2322A + L2334G |
| DS102 | L2336A + P2322A |
| DS103 | L2336A + P2322V + L2334M |
| DS104 | L2336A + P2322V + L2334G |
| DS105 | L2336A + P2322V |
| DS106 | L2336A + L2334M |
| DS107 | L2336A + L2334G |
| DS108 | L2336A |
| DS109 | A2328V + Y2387F + E2335G + P2322A + L2334M |
| DS110 | A2328V + Y2387F + E2335G + P2322A + L2334G |
| DS111 | A2328V + Y2387F + E2335G + P2322A |
| DS112 | A2328V + Y2387F + E2335G + P2322V + L2334M |
| DS113 | A2328V + Y2387F + E2335G + P2322V + L2334G |
| DS114 | A2328V + Y2387F + E2335G + P2322V |
| DS115 | A2328V + Y2387F + E2335G + L2334M |
| DS116 | A2328V + Y2387F + E2335G + L2334G |
| DS117 | A2328V + Y2387F + E2335G |
| DS118 | A2328V + Y2387F + E2335A + P2322A + L2334M |
| DS119 | A2328V + Y2387F + E2335A + P2322A + L2334G |
| DS120 | A2328V + Y2387F + E2335A + P2322A |
| DS121 | A2328V + Y2387F + E2335A + P2322V + L2334M |
| DS122 | A2328V + Y2387F + E2335A + P2322V + L2334G |
| DS123 | A2328V + Y2387F + E2335A + P2322V |
| DS124 | A2328V + Y2387F + E2335A + L2334M |
| DS125 | A2328V + Y2387F + E2335A + L2334G |
| DS126 | A2328V + Y2387F + E2335A |
| DS127 | A2328V + Y2387F + P2322A + L2334M |
| DS128 | A2328V + Y2387F + P2322A + L2334G |
| DS129 | A2328V + Y2387F + P2322A |
| DS130 | A2328V + Y2387F + P2322V + L2334M |
| DS131 | A2328V + Y2387F + P2322V + L2334G |
| DS132 | A2328V + Y2387F + P2322V |
| DS133 | A2328V + Y2387F + L2334M |
| DS134 | A2328V + Y2387F + L2334G |
| DS135 | A2328V + Y2387F |
| DS136 | A2328V + E2335G + P2322A + L2334M |
| DS137 | A2328V + E2335G + P2322A + L2334G |
| DS138 | A2328V + E2335G + P2322A |
| DS139 | A2328V + E2335G + P2322V + L2334M |
| DS140 | A2328V + E2335G + P2322V + L2334G |
| DS141 | A2328V + E2335G + P2322V |
| DS142 | A2328V + E2335G + L2334M |
| DS143 | A2328V + E2335G + L2334G |
| DS144 | A2328V + E2335G |
| DS145 | A2328V + E2335A + P2322A + L2334M |
| DS146 | A2328V + E2335A + P2322A + L2334G |
| DS147 | A2328V + E2335A + P2322A |
| DS148 | A2328V + E2335A + P2322V + L2334M |
| DS149 | A2328V + E2335A + P2322V + L2334G |
| DS150 | A2328V + E2335A + P2322V |
| DS151 | A2328V + E2335A + L2334M |
| DS152 | A2328V + E2335A + L2334G |
| DS153 | A2328V + E2335A |
| DS154 | A2328V + P2322A + L2334M |
| DS155 | A2328V + P2322A + L2334G |
| DS156 | A2328V + P2322A |
| DS157 | A2328V + P2322V + L2334M |
| DS158 | A2328V + P2322V + L2334G |
| DS159 | A2328V + P2322V |
| DS160 | A2328V + L2334M |
| DS161 | A2328V – L2334G |
| DS162 | A2328V |
| DS163 | Y2387F + E2335G + P2322A + L2334M |
| DS164 | Y2387F + E2335G + P2322A + L2334G |
| DS165 | Y2387F + E2335G + P2322A |
| DS166 | Y2387F + E2335G + P2322V + L2334M |

TABLE 9-continued

Mutations and combination of substitutions

| Name | Mutations |
|---|---|
| DS167 | Y2387F + E2335G + P2322V + L2334G |
| DS168 | Y2387F + E2335G + P2322V |
| DS169 | Y2387F + E2335G + L2334M |
| DS170 | Y2387F + E2335G + L2334G |
| DS171 | Y2387F + E2335G |
| DS172 | Y2387F + E2335A + P2322A + L2334M |
| DS173 | Y2387F + E2335A + P2322A + L2334G |
| DS174 | Y2387F + E2335A + P2322A |
| DS175 | Y2387F + E2335A + P2322V + L2334M |
| DS176 | Y2387F + E2335A + P2322V + L2334G |
| DS177 | Y2387F + E2335A + P2322V |
| DS178 | Y2387F + E2335A + L2334M |
| DS179 | Y2387F + E2335A + L2334G |
| DS180 | Y2387F + E2335A |
| DS181 | Y2387F + P2322A + L2334M |
| DS182 | Y2387F + P2322A + L2334G |
| DS183 | Y2387F + P2322A |
| DS184 | Y2387F + P2322V + L2334M |
| DS185 | Y2387F + P2322V + L2334G |
| DS186 | Y2387F + P2322V |
| DS187 | Y2387F + L2334M |
| DS188 | Y2387F + L2334G |
| DS189 | Y2387F |
| DS190 | E2335G + P2322A + L2334M |
| DS191 | E2335G + P2322A + L2334G |
| DS192 | E2335G + P2322A |
| DS193 | E2335G + P2322V + L2334M |
| DS194 | E2335G + P2322V + L2334G |
| DS195 | E2335G + P2322V |
| DS196 | E2335G + L2334M |
| DS197 | E2335G + L2334G |
| DS198 | E2335G |
| DS199 | E2335A + P2322A + L2334M |
| DS200 | E2335A + P2322A + L2334G |
| DS201 | E2335A + P2322A |
| DS202 | E2335A + P2322V + L2334M |
| DS203 | E2335A + P2322V + L2334G |
| DS204 | E2335A + P2322V |
| DS205 | E2335A + L2334M |
| DS206 | E2335A + L2334G |
| DS207 | E2335A |
| DS208 | P2322A + L2334M |
| DS209 | P2322A + L2334G |
| DS210 | P2322A |
| DS211 | P2322V + L2334M |
| DS212 | P2322V + L2334G |
| DS213 | P2322V |
| DS214 | L2334M |
| DS215 | L2334G |

Additional Modifications

In an embodiment, the variant is a variant of Pol θ comprising a modified polymerase domain as described above, which is further preceded in its N-terminal sequence by part or full central domain sequence.

In a further embodiment, the variant comprises the Pol θ polymerase sequence or any of the previously described functional fragments with any one of the mutation or combination of mutations described above, which further includes any type of tagging peptide in its N-terminal, C-terminal or both extremity. Said tagging peptide could be used for purification, identification, increasing expression, secretability or increasing catalytic activity. It will be understood that such different tags are extensively described in the literature and thus all tag known to a skilled person are covered by the present invention.

The variants of the invention can also include one or more exogenous or heterologous features at the N- and/or C-terminal regions of the protein for use, e.g., in the purification of the recombinant polymerase. The polymerases can also include one or more deletions (including domain deletions) that facilitate purification of the protein, e.g., by increasing the solubility of recombinantly produced protein. For e.g., the polypeptide fragment from amino acid position 1792 to 2590 of SEQ ID No1 has been identified as the shortest active fragment (SEQ ID No2) of the wild-type DNA polymerase Pol θ. (J. Mol. Biol. (2011) 405, 642-652)

Conversion of Other Family A Polymerases

As previously described Pol θ polymerases possess a polymerase activity even in absence of any template. When Pol θ polymerase domain sequence is aligned to other polymerase domains across the entire polymerase A Family, it appears that specific insertions are present in Pol θ polymerase domain. Deletion of a particular insert known as insert 2 (see table 1) is suppressing the ability of Pol θ to elongate nucleic acid fragment in absence of template.

In a particular embodiment, the present invention contemplates modified Family A polymerases according to the present invention, that are further modified by adding any insert 2 of a Pol θ polymerase in their polymerase domain.

In a further embodiment, the present invention contemplates modified Family A polymerases comprising any functionally equivalent mutations or combination previously described in its polymerase domain, said polymerases would be further modified by adding any insert 2 of a Pol θ polymerase in their polymerase domain.

Alternative Pol θ Polymerases

Human Pol θ polymerase sequence is given by SEQ ID No1. Pol θ polymerases could be found in many other organisms or microorganisms. All those Pol θ polymerases are good candidate for performing the present invention. In particular, modifications to alter a particular Pol θ polymerase sequence to give said polymerase an increased ability to incorporate rate reversible terminator modified nucleotides, can target any other Pol θ polymerase sequence.

In further particular aspect of the present invention, previously describe mutations or combination can target any other Pol θ polymerase sequence.

In particular embodiment modified Pol θ polymerase with increased incorporation rate for reversible terminator modified nucleotides presents at least 80% identity with SEQ ID No1, in particular at least 85%, 90% 95% 97% 98%, or 99% identity with SEQ ID No1.

In particular embodiment, the variant is a modified Pol θ polymerase having any of the previously described mutations or combination of mutations and at least 80% identity with SEQ ID No1, in particular at least 85% 90%, 95%, 97%, 98% or 99% identity with SEQ ID No1.

The variants according to the present invention are described according to alteration of specific residues having their position determined by SEQ ID No1. It will be understood that the present invention encompasses any modified Pol θ polymerase bearing identical alteration in any functionally equivalent residue.

Enzymatic Synthesis of Nucleic Acid

It is the purpose of the present invention to provide variants of Family A polymerases that may be used for the synthesis of nucleic acid. More particularly, it is the purpose of the present invention to provide variants of Family A polymerases suitable to add reversible terminator modified nucleotides to an initiating nucleic acid strand. The blocking group may be then removed for allowing a new addition of reversible terminator modified nucleotide.

According to the invention, by use of a variant of the invention, it is possible to implement successive cycle comprising addition and deprotections This process will therefore allow by multiple cycles of addition of a reversible terminator modified nucleotide and further removal of the blocking group to allow the controlled extension of an initiating nucleic acid strand into a defined sequence.

The present invention contemplates the use of modified Family A polymerase according to the present invention in any enzymatic nucleic acid synthesis process. In a particular aspect of the invention the modified Family A polymerase is Pol θ polymerase.

It is also the purpose of the present invention to provide a process for synthesizing a nucleic acid molecule without template, comprising a step of contacting a nucleic acid primer with both at least one nucleotide, preferably at least one 3'O-modified nucleotide, and a variant of the invention.

The present invention contemplates the concept of enzymatic nucleic acids process. In such process, nucleic acids molecules are de novo synthesized in absence of any template strand. Accordingly, ordered sequence of nucleotides are coupled to an initiator nucleic acid fragment with the help of the variant of the invention. It will be understood that quantitative coupling and more generally high coupling efficiency of each nucleotides to the growing nucleic acid chain is of great importance. It also will be understood that non terminator nucleotides such as natural nucleotides or permanent labeled nucleotides will not permit any control over the sequence synthesized and by resulting for example in uncontrolled and undesired poly-additions.

According to a particular embodiment, the enzymatic nucleic acid process comprises:
a. Providing a nucleic acid molecule linked to a solid support;
b. Reacting previous nucleic acid molecule with a reversible terminator modified nucleotide and a modified A Family polymerase according to the present invention;

According to another particular embodiment, the enzymatic nucleic acid process comprises:
a. Providing a nucleic acid molecule linked to a solid support;
b. Adding a reversible terminator modified nucleotide and a modified A Family polymerase according to the present invention;
c. First removing of one or several reagents from the solid support;
d. Reacting the reversible moiety of the reversible terminator modified nucleotide in order to deprotect it for further subsequent elongation;
e. Second removing of one or several reagents from the solid support;
f. Optionally and finally cleaving the nucleic acid molecule from the solid support.

According to another particular embodiment, the enzymatic nucleic acid process comprise cycles subdivided in the following way:
a. a phase of elongation of Xi nucleotides to one end of said fragments, it being possible for X to be between 1 and 5, preferably between:1 and 3, i being the number of the cycle, making it possible to obtain fragments comprising n+Xi nucleotides, known as first phase, and comprising the following stages:
a first stage of attaching, to a first support, a first end of initial nucleic acid fragments or nucleic acid fragments in the course of elongation, including n nucleotides,
a stage of addition of the reagents necessary for the modified A Family polymerase according to the present invention addition,
a stage of modified A Family polymerase according to the present invention addition of Xi nucleotides to the second end of said nucleic acid fragments, it being possible for X to be between 1 and 5, preferably 1 and 3, i being the number of the cycle,
an optional stage of removal of the undesirable reagents from the reaction medium,—a stage of detaching, from said first support, said fragments comprising n+Xi nucleotides,
a first stage of transfer of said fragments comprising n+Xi nucleotides,
b. a phase of purification of the fragments having a correct sequence comprising n+Xi nucleotides, known as second phase, comprising the following successive stages:
a second stage of attaching, to a second support, said fragments comprising n+Xi nucleotides by their end carrying the Xi nucleotides added during the first phase,
a stage of removal of the fragments which have not been added to and of the fragments which have not been attached to the second support,
a stage of detaching said fragments comprising n+Xi nucleotides from said second support,
an optional stage of removal, from the reaction medium, of the undesirable residual reagents;
c. an optional phase of amplification, preferably enzymatic amplification, such as by PCR, of the fragments having a correct sequence comprising n+Xi nucleotides, known as third phase, comprising the following successive stages:
a stage of addition of the reagents necessary for the amplification,
a stage (optionally composed of substages making the process possible) of multiplication by a multiplication factor Yi of the fragments comprising n+Xi nucleotides, i being the cycle number, it being possible for Y to be between 1 and $4\times10^{10}$, preferably between 1 and $1\times10^{9}$,
a stage of transfer of the fragments comprising n+Xi nucleotides,
each cycle being carried out in a reaction medium compatible with an enzymatic addition and an enzymatic amplification, such as an aqueous medium, the synthesis process also comprising, at the end of all of the i elongation cycles, a stage of final amplification by a multiplication factor Yf.

In the context of the invention, the expression "cleaving reaction" refers to any action of substance or physical conditions, which is able to cleave the additional group previously described on reversible terminator nucleotides. A person skilled in the art is able to determine a cleaving reaction for any previously listed group.

In one embodiment, the cleaving agent is a chemical cleaving agent. In an alternative embodiment, the cleaving agent is an enzymatic cleaving agent.

It will be understood by the person skilled in the art that the selection of cleaving agent is dependent on the type of 3'-nucleotide blocking group used. For example, tris(2-carboxyethyl)phosphine (TCEP) can be used to cleave a 3'O-azidomethyl groups, palladium complexes can be used to cleave a 3'O-allyl groups, or sodium nitrite can be used to cleave a 3'O-amino groups. In particular embodiment, the cleaving reaction is involving: TCEP, a palladium complex or sodium nitrite.

In particular embodiment, the cleaving reaction is performed in the presence of additional components such as denaturant (urea, guanidinium chloride, formamide or betaine for example). In a further embodiment, the cleavage reaction is performed with one or more buffers. It will be understood by the person skilled in the art that the choice of buffer is dependent on the exact mechanism of reaction.

The present invention relates to modified A Family polymerases with the capacity to incorporate in a quantitative way reversible terminator modified nucleotides. In a particular aspect, the invention related to Pol θ polymerase with the capacity to incorporate in a quantitative way reversible terminator modified nucleotides.

By "quantitative way" or "quantitative reaction", it is meant a reaction that goes to completion, wherein the reactants are totally converted into the product.

Polymerase that incorporates in a quantitative way reversible terminator nucleotide is a polymerase able to elongate every fragments of nucleic acid with all the nucleotides available leading to the conversion of all the starting fragments of length n to fragment of length n+1.

Initiating Fragments and Solid Support

As used herein, "initiating fragment" refers to a short oligonucleotide sequence with a free 3'-end, which can be further elongated. In one embodiment, the initiating fragment is a DNA initiating fragment. In an alternative embodiment, the initiating fragment is an RNA initiating fragment.

In one embodiment, the initiating fragment possesses between 3 and 100 nucleotides, in particular between 3 and 20 nucleotides.

In one embodiment, the initiating fragment is single-stranded. In an alternative embodiment, the initiating fragment is double-stranded.

In one embodiment, the initiating fragment is immobilized on a solid support. The initiating fragment may be attached with various method to a solid support resulting in a stable under the various enzymatic or synthesis reaction conditions that the fragment will undergo.

In one embodiment, the initiating fragment is immobilized on a solid support via a reversible interacting moiety, such as a chemically-cleavable linker, an antibody/immunogenic epitope, a biotin/biotin binding protein or glutathione-GST tag. In a further embodiment, the initiating fragment is immobilized on a solid support via a chemically-cleavable linker, such as a disulfide, allyl, or azide-masked hemiaminal ether linker.

In an initiating fragment, the immobilized part contains at least one restriction site. The use of restriction enzymes and restriction sites to selectively hydrolyze nucleic acids chain at a specific site is describe in the literature. Any skilled person will be able to choose the appropriate restriction enzyme that will match the initiating fragment cleaving site sequence.

In an alternative embodiment, the initiating fragment contains at least one uridine. Treatment with uracil-DNA glycosylase (UDG) generates an abasic site. Treatment on an appropriate substrate with an apurinic/apyrimidinic (AP) site endonuclease will extract the nucleic acid strand.

Nucleic Acid Molecules

It is also the purpose of the invention to provide a nucleic acid molecule encoding a variant of the invention. As used herein, a "nucleic acid molecule" refers to a polymer of nucleosides. In one embodiment, the nucleic acid is a DNA. In an alternative embodiment, the nucleic acid is RNA. In an alternative embodiment, the nucleic acid is XNA.

It will be understood by a skilled person that each of the previously listed nucleic acid molecule could beat modification on the bases of the nucleotides that constitute the polymeric molecule. Such modifications could be natural modification, such as epigenetic modifications or unnatural modification such as labels.

In one embodiment, nucleic acid molecules are DNA, RNA or XNA bearing naturally occurring epigenetic modifications such as methylation, hydfroxymethylation, formylation or 5-carboxylation.

In one embodiment, nucleic acid molecules are DNA, RNA or XNA bearing unnaturally occurring modifications such as fluorescent tag, fluorescent label and/or interaction groups.

In one embodiment, nucleic acid molecules are polymeric molecules having length of more than 50, 100, 200, 300, 400, 500, 600, 700, 800, 900, 1 000, 2 000, 3 000, 4 000, 5 000, 6 000, 7 000, 8 000, 9 000, 10 000, 15 000, 20 000, 30 000, 40 000, 50 000 or 100 000 nucleotides.

Applications

Described herein is the use of variant of a DNA polymerase of family A to be used for nucleic acid synthesis, oligonucleotide synthesis, probe synthesis, nucleic acid amplification, aptamers, therapeutic nucleic acid molecules, drug target discovery and validation, disease diagnosis, metabolic engineering, data storage, crops improvement, library design, sequencing pools, nucleic acid labeling or attachment or any other application that is involving nucleic acid molecules.

Kits, Enzyme and Nucleotide Composition

A particular aspect of the invention is relative to the composition and the use of kits comprising a modified A Family polymerase according to the invention, or to any particular aspect of the present invention, with optionally any combination of one or more components selected from: an initiating fragment, one or more reversible terminator nucleotides, additional enzyme and reagents used in a cleaving reaction. Said kits can be used in a method of enzymatic nucleic acid synthesis.

The present invention covers the composition of matter comprising modified A Family DNA polymerase according to the invention, or to any particular aspect of the present invention, with reversible terminator modified nucleotide in a mix with appropriate buffer and ratio concentration.

EXAMPLES

Example 1

Generation, Expression and Purification of Modified A Family Polymerase According to the Invention Expression Strain Generation The gene coding for the polymerase domain plus a fragment of the central domain (amino acid 1792 to 2590), i.e., SEQ 2, has been ordered as a synthetic gene from IDT provider (eu.idtdna.com/pages/products/genes/custom-gene-synthesis) with an optimization of the codon sequence for subsequent expression in E. coli, resulting in DNA SEQ 19. Through standard restriction ligation techniques, it has been cloned into Champion pET SUMO vector (thermofisher cat. K30001). The resulting vector is named pSUMO-THETA. The pSUMO-THETA vector has been transformed in commercial E. coli strain BL21-DE3 (Novagen). Colonies capable of growing on kanamycin LB-agar plates have been isolated for subsequent plasmid extraction. Extracted plasmids have been sent to sequencing using the following primers:

```
T7-pro:                              (SEQ ID No 7)
TAATACGACTCACTATAGGG

T7-ter:                              (SEQ ID No 8)
GCTAGTTATTGCTCAGCGG
```

Correct Clones are Name Ec-PolTheta

Polymerase Variants Generation

The pSUMO-THETA vector is used as starting vector. Specific primers comprising one or several point mutations have been generated from Agilent online software (www.genomics.agilent.com: 80/primerDesignProgram.jsp). The commercial available kit QuickChange II (Agilent) has been used to generate the desire modified polymerases comprising the target mutations. Experimental procedures have followed the supplier's protocol. The resulting plasmids coding for the DSi variants are named pSUMO-DSi, wherein i is the variant number given in Table 9. After generation of the different pSUMO-DSi vectors, each of them have been sequenced. Vectors with the correct sequence have been transformed in E. coli producer strains, as described before. Clones able to grow on kanamycin LB-agar plates were isolated and name Ec-DSi.

Expression

The Ec-PolTheta and Ec-DSi strains have been used for inoculating 250 mL erlens with 50 mL of LB media supplemented with appropriate amount of kanamycin. After overnight growth at 37° C., appropriate volumes of these pre-cultures have been used to inoculate 5 L erlens with 2 L LB media with kanamycin. The initial OD for the 5 L cultures was chosen to be 0.01. The erlens were put at 37° C. under strong agitation and the OD of the different cultures were regularly checked. After reaching an OD comprised between 0.6 and 0.9, each erlen was supplemented by the addition of 1 mL of 1M IPTG (Isopropyl β-D-1-thiogalactopyranoside, Sigma). The erlens were putting back to agitation under a controlled temperature of 30° C. After overnight expression, the cells were harvested in several pellets. Pellets expressing the same variants were pooled and stored at −20° C., eventually for several months.

Extraction

Previously prepared pellets were thaw in 30 to 37° C. water bath. Once fully thawed, pellets were resuspended in lysis buffer composed of 50 mM tris-HCL (Sigma) pH 7.5, 150 mM NaCl (Sigma), 0.5 mM mercaptoethanol (Sigma), 5% glycerol (Sigma), 20 mM imidazole (Sigma) and 1 tab for 100 mL of protease cocktail inhibitor (Thermofisher). Careful resuspension was carried out in order to avoid premature lysis and remaining of aggregates. Resuspended cells were lysed through several cycles of French press, until full color homogeneity was obtained. Usual pressure used was 14,000 psi. Lysate was then centrifuge for 1 h to 1 h30 at 10,000 rpm. Centrifugate was pass through a 0.2 μm filter to remove any debris before column purification.

Purification

A two-step affinity procedure was used to purify the produced and extracted polymerase enzymes. For the first step a Ni-NTA affinity column (GE Healthcare) was used to bind the polymerases. Initially the column has been washed and equilibrated with 15 column volumes of 50 mM tris-HCL (Sigma) pH 7.5, 150 mM NaCl (Sigma), 0.5 mM 2-mercaptoethanol (Sigma), 5% glycerol (Sigma) and 20 mM imidazole (Sigma). Polymerases were bond to the column after equilibration. Then a washing buffer, composed of 50 mM tris-HCL (Sigma) pH 7.5, 500 mM NaCl (Sigma), 0.5 mM 2-mercaptoethanol (Sigma), 5% glycerol (Sigma) and 20 mM imidazole (Sigma), was apply to the column for 15 column volumes. After wash the polymerases were eluted with 50 mM tris-HCL (Sigma) pH 7.5, 500 mM NaCl (Sigma), 0.5 mM mercaptoethanol (Sigma), 5% glycerol (Sigma) and 0.5M imidazole (Sigma). Fraction corresponding to the highest concentration of polymerases of interest were collected and pooled in a single sample. For the second step a Fast Desalt HR column (GE Healthcare) was used to change the buffer of the samples. The column was first washed and equilibrated with 25 Mm potassium phosphate pH 7.5 (Sigma), 10% (v/v) glycerol (Sigma), 1 mM EDTA (Sigma), 1 mM 2-mercaptoethanol (Sigma) and 75 mM KCl (Sigma). Samples were applied to the column. Then the previously used buffer was applied with a gradient of 0.075 to 0.5M of KCl. Fraction corresponding to the highest concentration of polymerases of interest were collected and pooled to give the final preparation. Small aliquots of this preparation were then flash frozen in liquid nitrogen and stored for long term at −20° C.

Example 2

Three-Dimensional Study of Modified Family A Polymerase According to the Invention Structural analysis of Pol θ polymerase is giving critical information for rational modifications in particular substitution mutations.

Different Pol θ polymerases structures has been found on the PDB (www.rcsb.org/pdb/home/home.do) and analyzed through specific interactive visualization sowtware Chimera (www.cgl.ucsf.edu/chimera/).

Distance analysis of residues inside the catalytic pocket is shown in FIG. 1.

Example 3

Activity of the Modified Family A Polymerase According to the Invention

Activity of the various mutant generated, expressed and purified according to example 1 is evaluated through the following assay. All the results are compared among themselves in addition to the wild type pol theta and to a control tube lacking any polymerase enzyme.

TABLE 10

| Activity test | | |
|---|---|---|
| Reagent | Concentration | Volume |
| $H_2O$ | — | 2 μL |
| HEPES pH 7.5 | 250 mM | 1 μL |
| 2-mercaptoethanol | 20 mM | 1 μL |
| EDTA | 1 mM | 1 μL |
| MnCl2 | 50 mM | 1 μL |
| BSA | 500 μg/mL | 1 μL |
| dNTP | 1 mM | 1 μL |
| Purified pol theta | 50 μM | 1 μL |
| [$^{32}$P]-primer | 500 nM | 1 μL |

Primer used was the following:

5'-AAAAAAAAAAAAAGGGG-3' (SEQ ID No 9)

It has been initially labeled with [γ-$^{32}$P]-ATP following a DNA labeling standard procedure.

Nucleotides used (noted as dNTP in table 11) are 3'-O-amino-2',3'-dideoxynucleotides-5'-triphosphate (ONH2, Firebird Biosciences) or 3'-biot-EDA-2',3'-dideoxynucleotides-5'-triphosphate (Biot-EDA, Jena Biosciences), such as 3'-O-amino-2',3'-dideoxyadenosine-5'-triphosphate or 3'-biot-EDA-2',3'-dideoxyadenosine-5'-triphosphate for example.

For each different mutant tested, one tube was used for the reaction. The reagents were added in the tube starting from the water and then in the order of Table 10. After 30 min at 37° C. the reaction was stopped by addition of formamide (Sigma).

Gel Analysis

Sample from activity test has been analyzed through polyacrylamide 16% (biorad) denaturing gel. Gel were made just before the analysis by pouring polyacrylamide inside glass plates and let it polymerizes. The gel inside the glass plates was mounted on an adapted tank filed with TBE buffer (Sigma) for the electrophoresis step. The samples to analyze were loaded on the top of the gel.

A tension of 500 to 2,000V was applied between the top and bottom of the gel for 3 to 6 h at room temperature. Once migrated according to the sample target size, system was dismantled and gel was carefully extracted from the glass plate. The gel was then placed in an incubation cassette with a phosphorous screen (Amersham) and incubated for 10 to 60 min before phosphorescence scan through the use of Typhoon instrument (GE Life Sciences).

Figure 2:
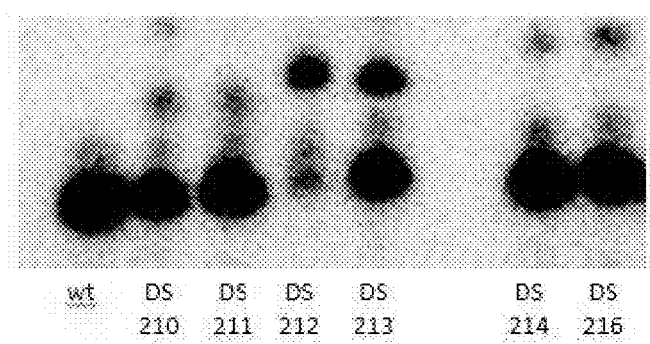
FIG. 2: Elongation assay comparing performances of wild type SEQ2 Pol θ with modified Pol θ enzymes with mutations given by table 10. The assay involves 5' radio labeled primers and 3'-O-amino reversible terminator modified nucleotides: 3'-O-amino-2',3'-dideoxyadenosine-5'-triphosphate. The picture represents a polyacrylamide gel migration of the results of the elongation assay.
Figure 3:
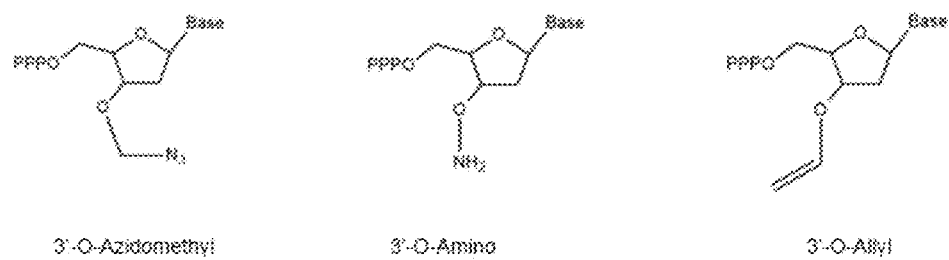
FIG. 3: Example of structure of reversible terminator modified nucleotides. The base moiety could either represent adenine, guanine, cytosine or thymine if natural deoxynucleotides are considered or any other base found in natural of synthetic nucleotides. The OPPP moiety represents the triphosphate group.
Figure 4:
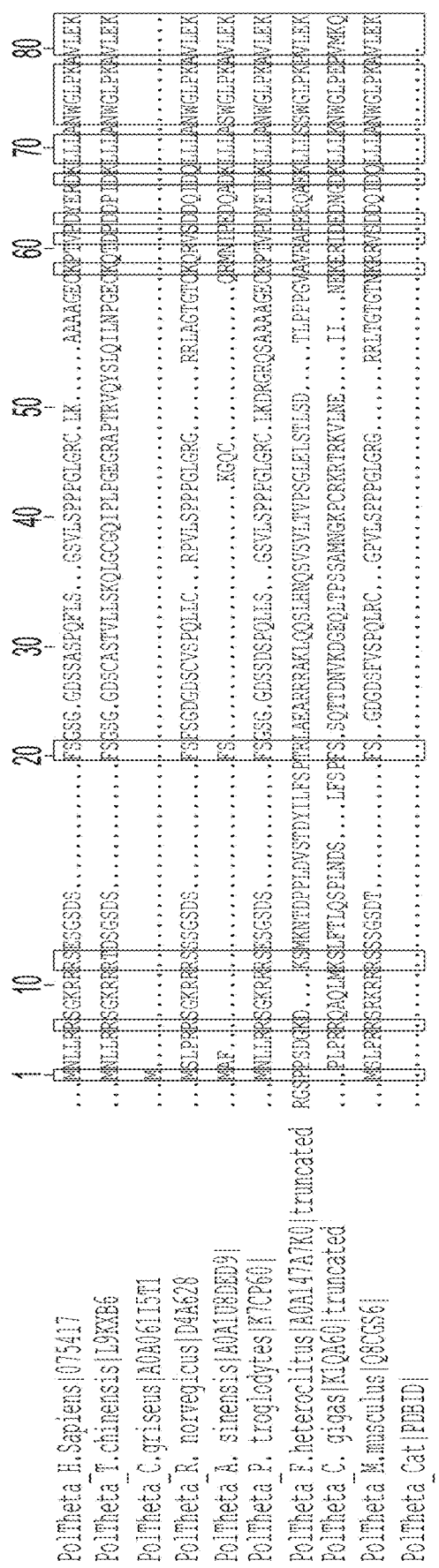
FIG. 4: Amino acid alignment of various Pol θ polymerase: *H. sapiens* (UniProtKB O75417 SEQ ID No1), *T. chinensis* (UniProtKB L9KXB6 SEQ ID No11), *C. griseus* (UniProtKB A0A061I5T1 SEQ ID No12), *R. norvegicus* (UniProtKB D4A628 SEQ ID No13), *A. sinensis* (UniProtKB A0A1U8DED9 SEQ ID No14), *P. troglodytes* (UniProtKB K7CP60 SEQ ID No15), *F. heteroclitus* (UniProtKB A0A147A7K0 SEQ ID No16), *C. gigas* (UniProtKB K1QA60 SEQ ID No17), *M. musculus* (UniProtKB Q8CGS6 SEQ ID No18) and *H. sapiens* (partially—SEQ ID No2).
Figure 4:
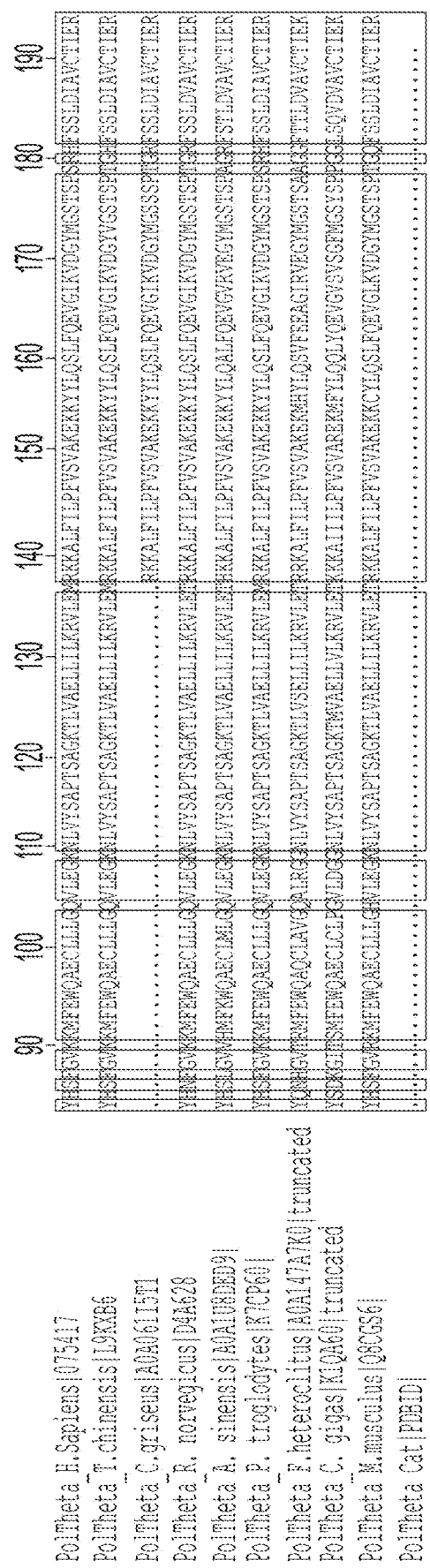
Figure 4:
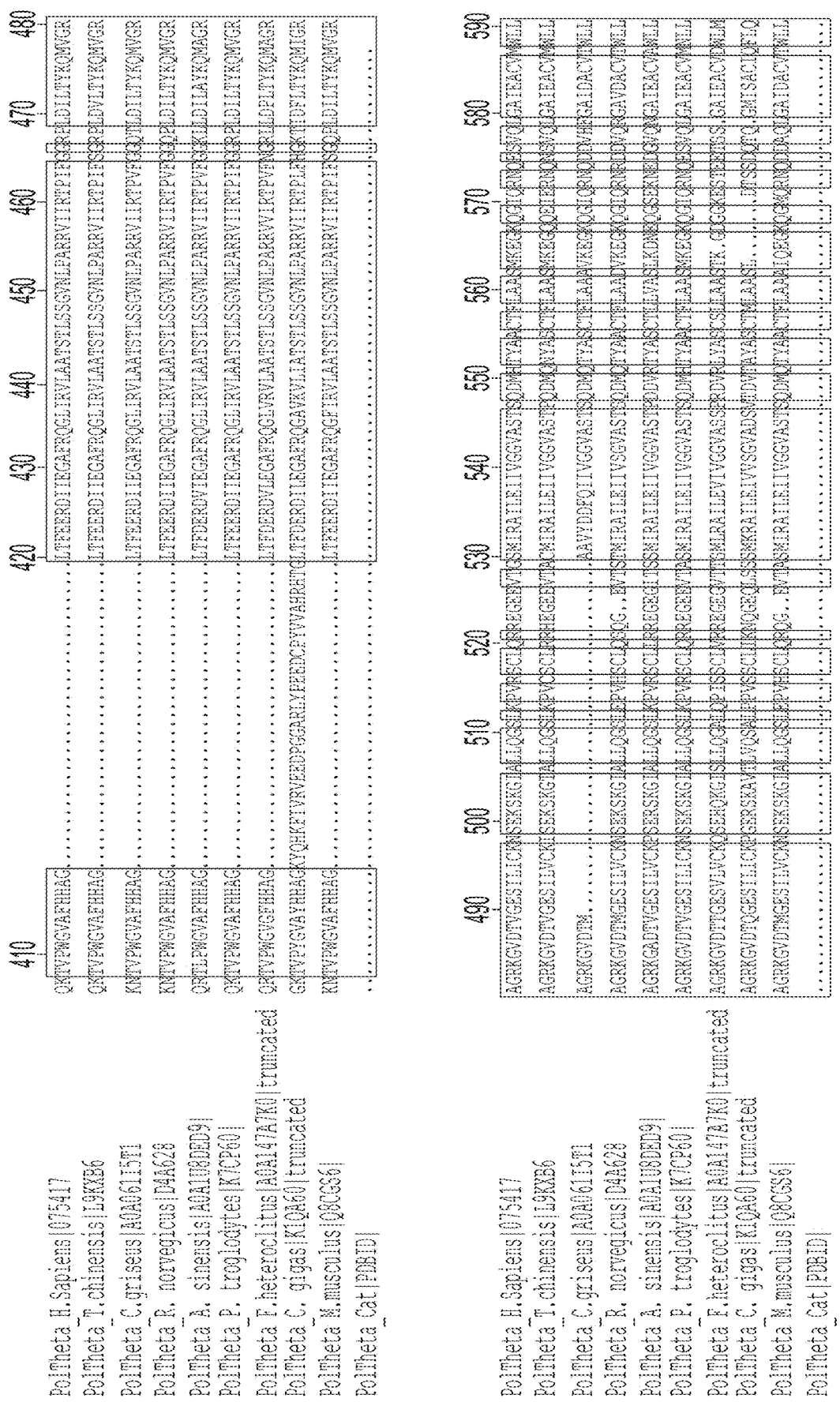
Figure 4:
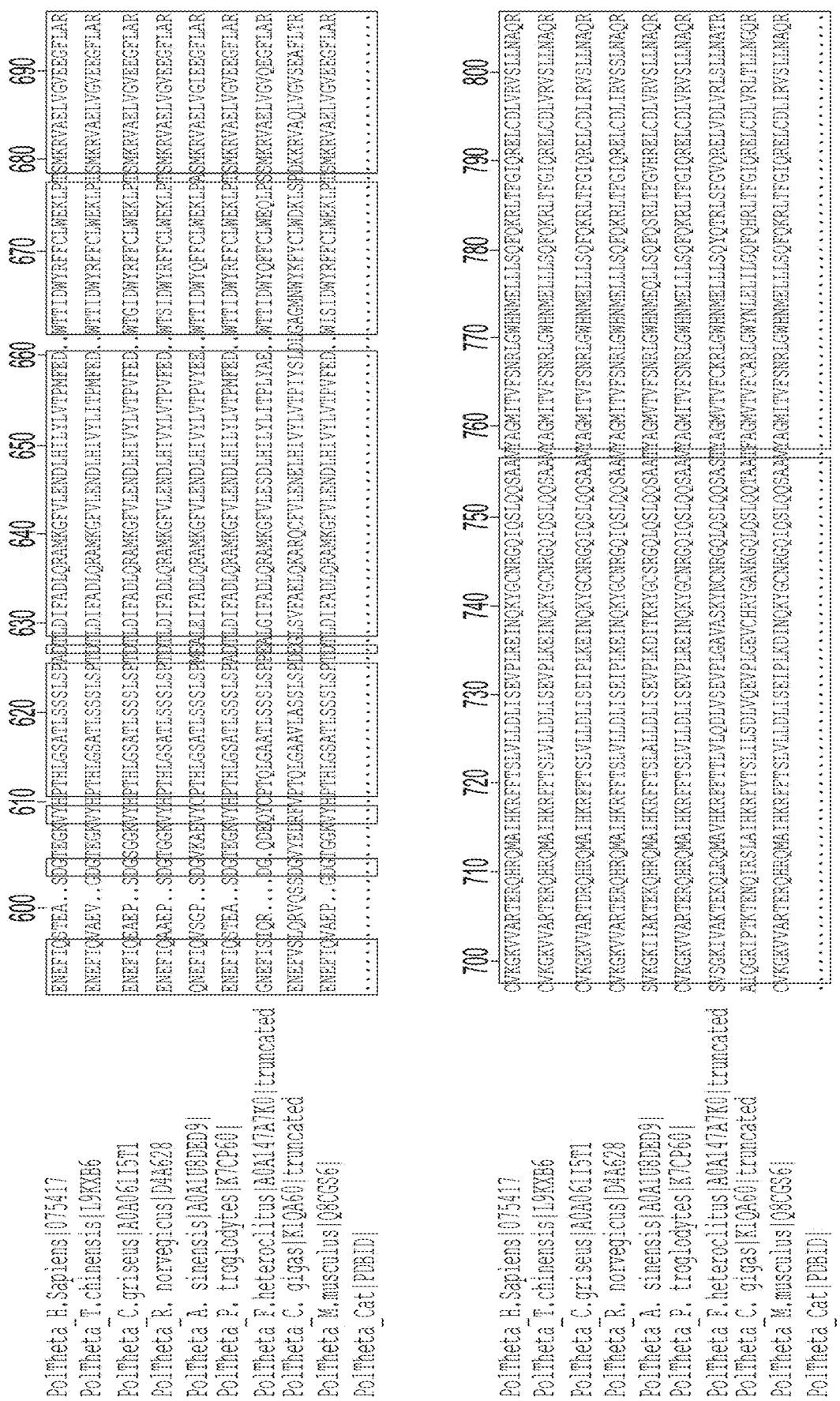
Figure 4:
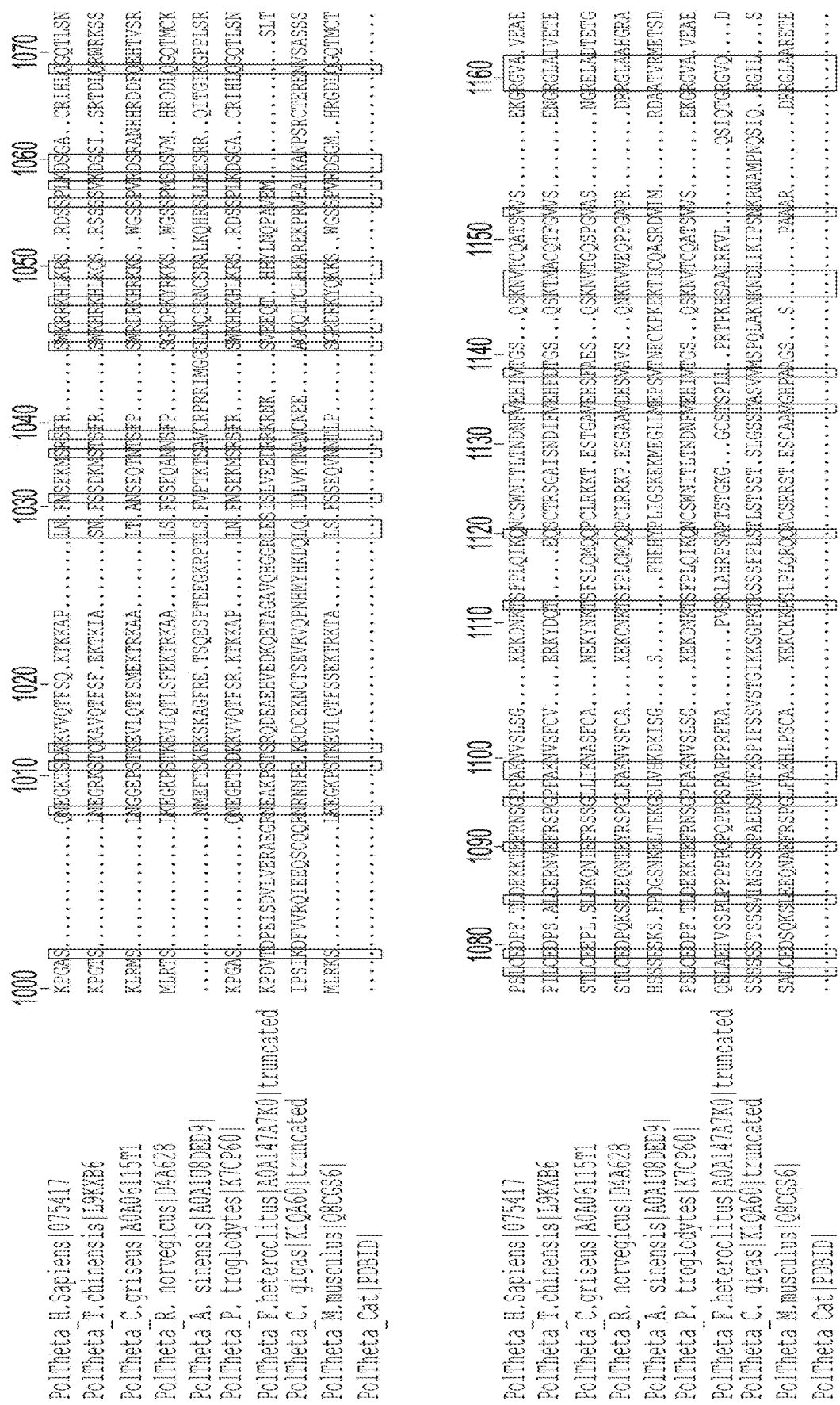
Figure 4:
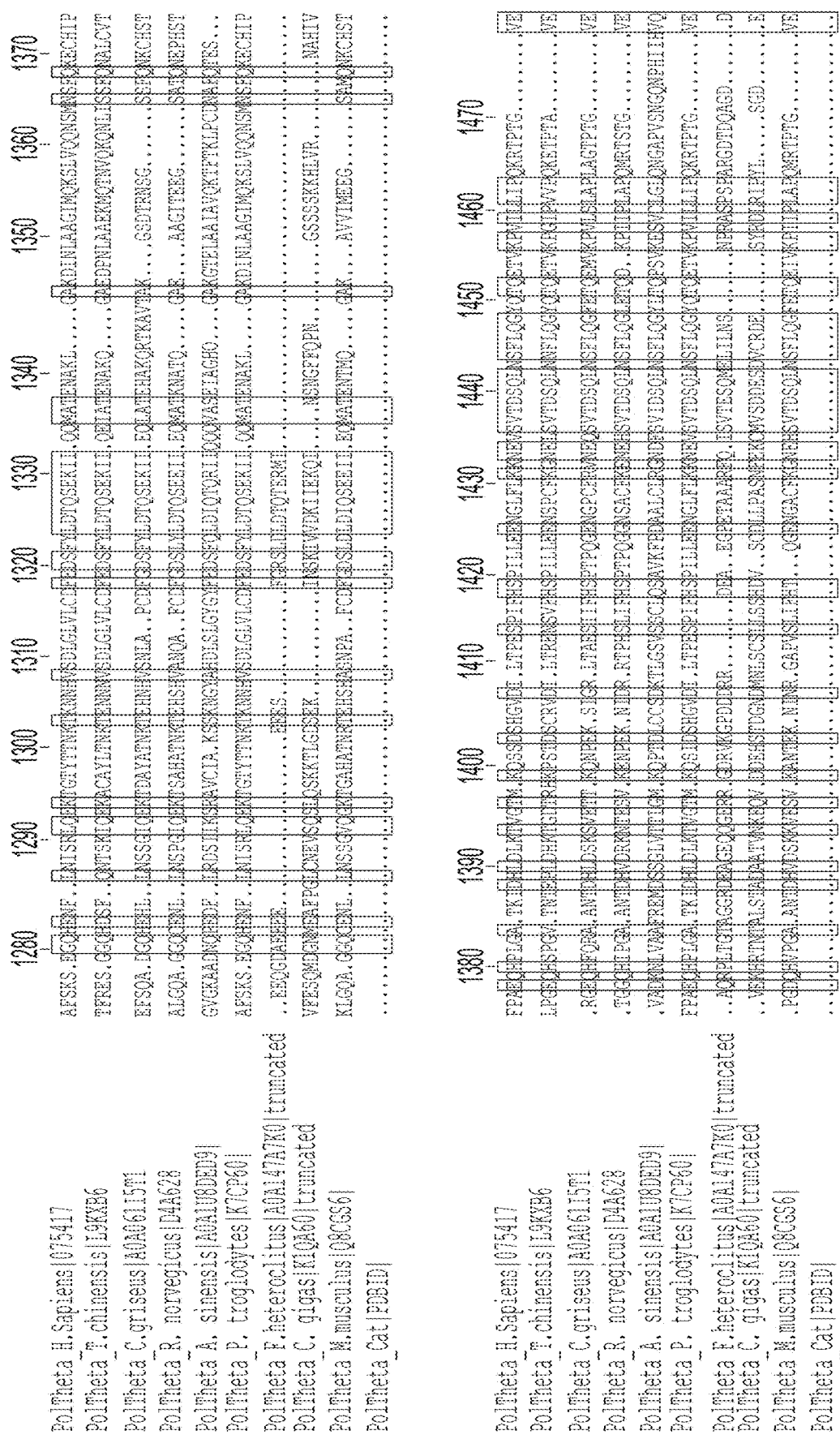
Figure 4:
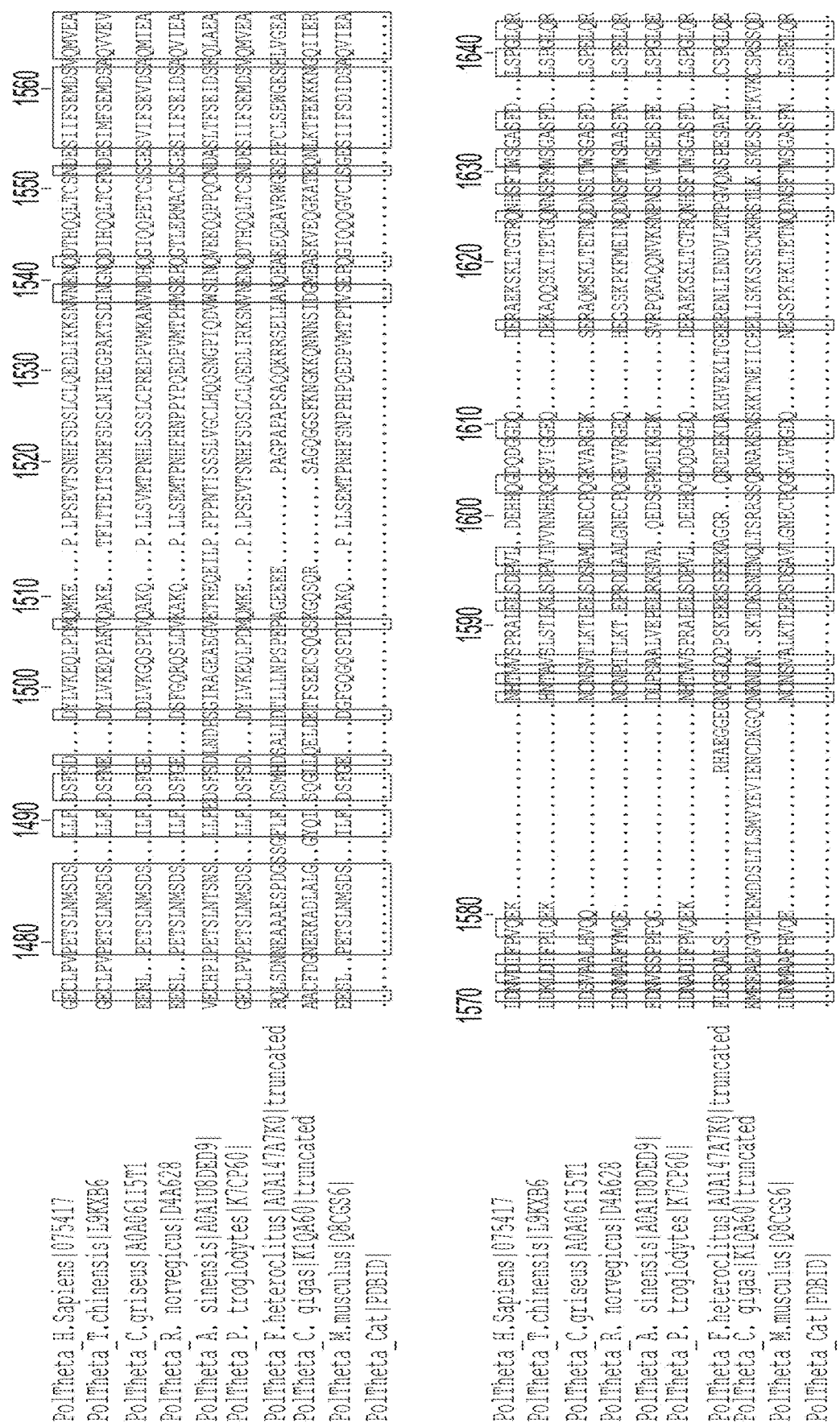
Figure 4:
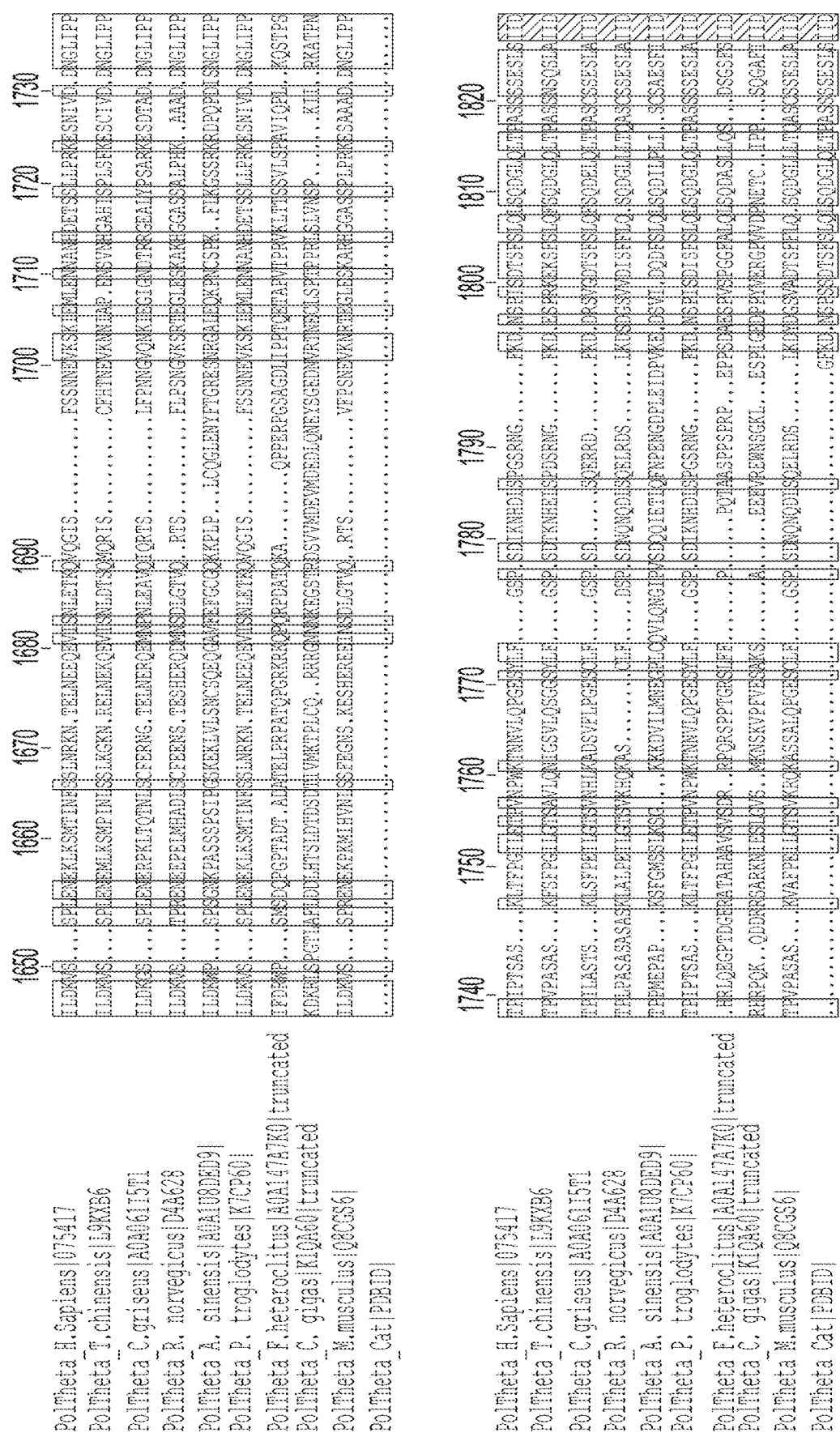
Figure 4:
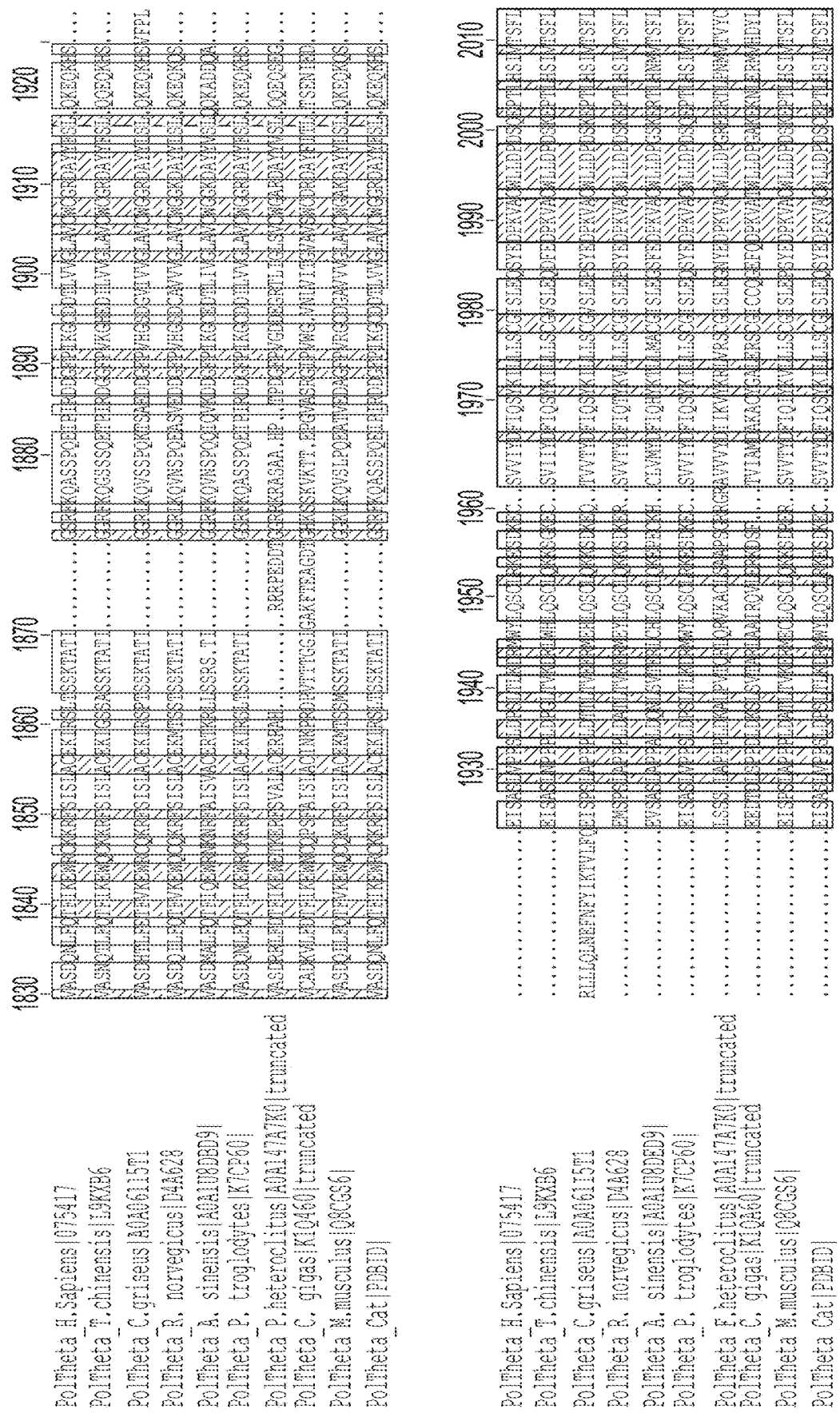
Figure 4:
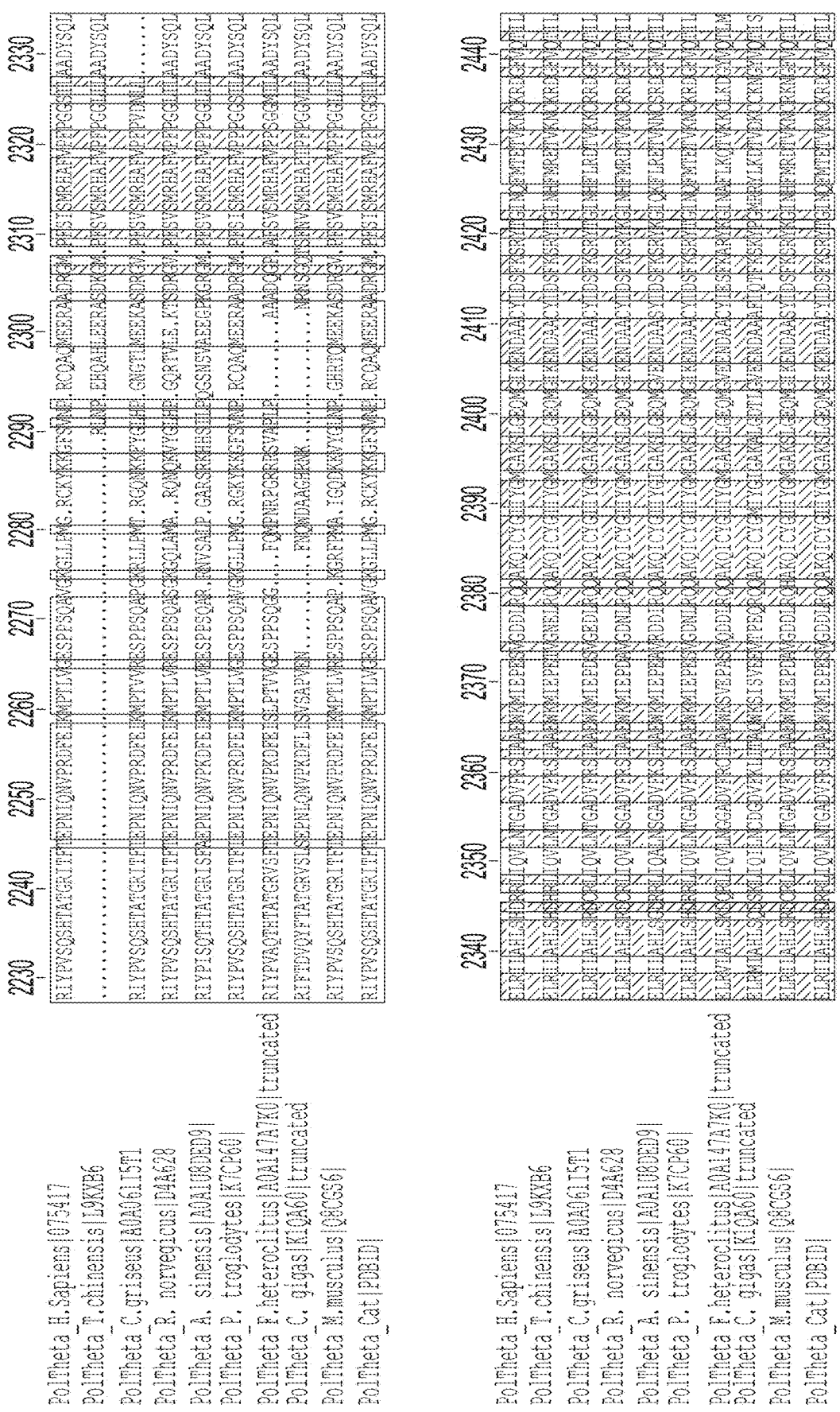
Figure 4:
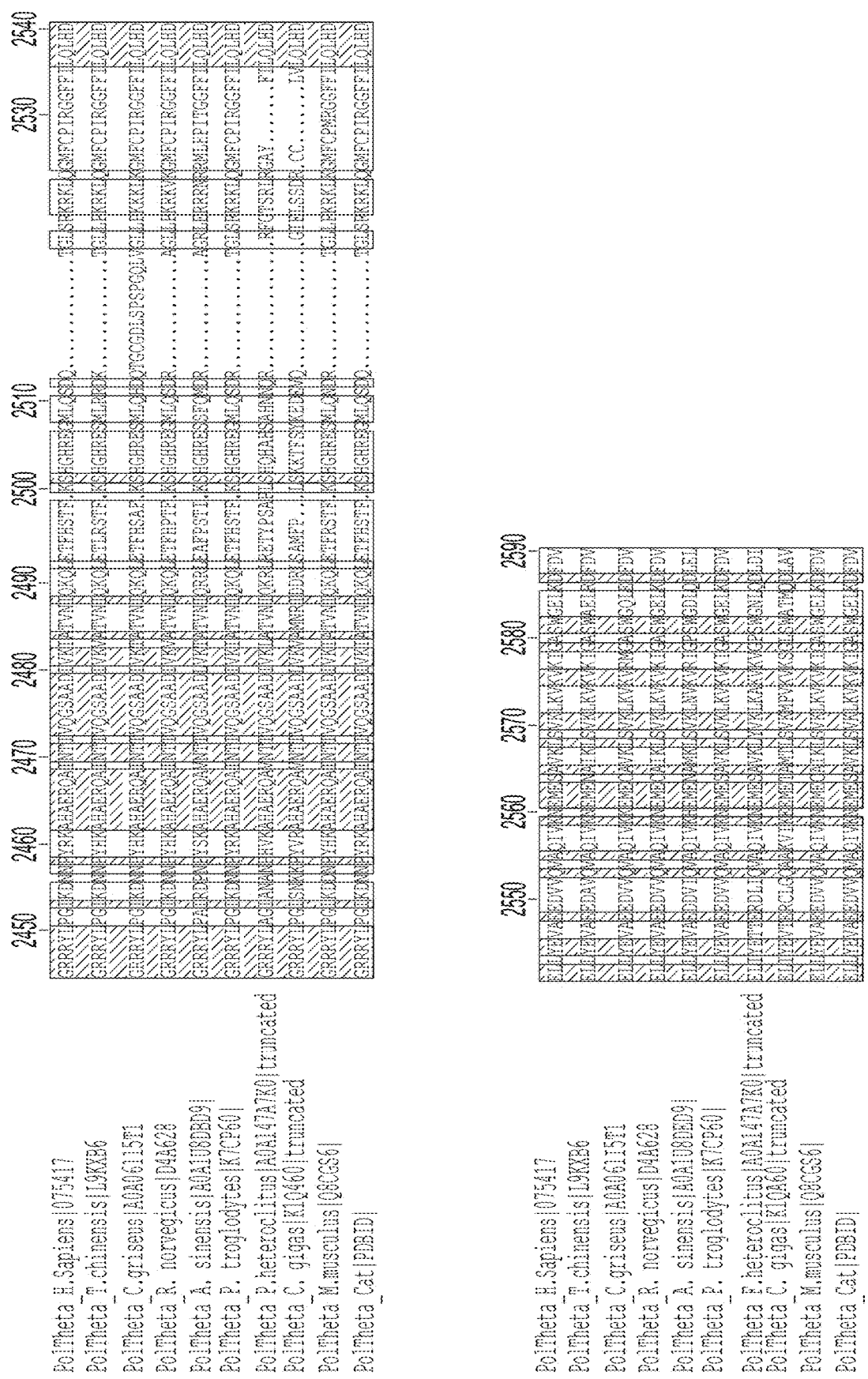

Results are showed on FIG. 2.

The invention claimed is:

1. A variant of a DNA polymerase of family A, comprising an amino acid sequence that is at least 90% identical to SEQ ID NO: 2, with at least one amino acid modification as compared to SEQ ID NO: 2, wherein the variant comprises a substitution at a position corresponding to E2335, wherein the positions are numbered by reference to the amino acid sequence set forth in SEQ ID NO: 1, and wherein the variant comprises an E2335G mutation.

2. The variant of claim 1, wherein the variant further comprises at least one substitution in the amino acid sequence as set forth in SEQ ID NO: 3, selected from the group consisting of D2330E/R/H/K/T/V/A/G, Y2331F/W/P/H/M/L/V/A, S2332T/N/Q/V/A/G, Q2333N/T/S/A/G/V, L2334M/E/N/F/K/D/A/G, L2336M/E/N/F/K/D/A/G, R2337H/K/D/E/A/G/M/F, I2338V/A/G/L/T/S/D/K/M, L2339M/E/N/F/K/D/A/G/I, and/or wherein the variant comprises at least one substitution in the amino acid sequence as set forth in SEQ ID NO: 4 selected from the group consisting of P2322A/V/I/L/G/C, G2323C/P/A/V/K/D, G2324C/P/A/V/K/D, S2325L/N/M/V/T/A/G/D/K, I2326V/A/G/L/T/S/D/K/M, L2327M/E/N/F/K/D/A/G/I/V, A2328V/T/G, A2329V/T/G, and/or wherein the variant comprises at least one substitution in the amino acid sequence as set forth in SEQ ID NO: 5 selected from the group consisting of D2376E/R/H/K/T/V/A/G/N, D2377E/R/H/K/T/V/A/G/N, L2378M/E/N/F/K/D/A/G/I, R2379H/K/D/E/A/G/M/F, Q2380N/T/S/A/G/V, Q2381N/T/S/A/G/V, A2382V/T/G, K2383R/H/D/E/Q/N/C/A/G/S/T, Q2384N/T/S/G/V, I2385V/A/G/L/T/S/D/K/M, C2386G/P/A/V/S/N/Q/D/K, Y2387F/W/P/H/M/L/V/A, G2388C/P/A/V/K/D, I2389V/A/G/L/T/S/D/K/M, I2390V/A/G/L/T/S/D/K/M, Y2391F/W/P/H/M/L/V/A, and/or wherein the variant comprises at least one substitution in the amino acid sequence as set forth in SEQ ID NO: 6 selected from the group consisting of E2199G/A/N/T/S/D/K, W2200Y/F/P/L/I/V/A/G/E, R2201H/K/D/E/A/G/M/F/S/P, R2202H/K/D/E/G/M/F/S/P, I2203V/A/G/L/T/S/D/K/M/P, T2204S/N/Q/C/G/M/K/D, wherein the positions are numbered by reference to the amino acid sequence set forth in SEQ ID NO: 1.

3. The variant of claim 1, wherein the variant further comprises at least one amino acid modification at position(s) corresponding to residues selected from D2330, D2540 or E2541, excluding D2540N/A or E2541Q/A, wherein the positions are numbered by reference to the amino acid sequence set forth in SEQ ID NO: 1.

4. The variant of claim 3, wherein the at least one amino acid modification comprises one or more substitutions selected from D2330E/R/H/K/T/V/A/G, D2540E/K/R/H/Q/S/T/C and E2541D/R/H/K/N/S/T/C.

5. The variant of claim 1, wherein the variant further comprises at least one amino acid modification at position(s) corresponding to residues selected from K2181, R2315, F2359, Y2391 and selected from wherein the positions are numbered by reference to the amino acid sequence set forth in SEQ ID NO: 1.

6. The variant of claim 5, wherein the at least one amino acid modification comprises one or more substitutions selected from K2181R/H/D/E/Q/N/C/G/S/T, R2315H/K/D/E/A/G/M/F, F2359M/L/I/V/A/G/P/T/K/D and A2477V/T/G.

7. The variant of claim 1, wherein the variant comprises at least a substitution or a combination of substitutions selected from the group consisting of:

L2336A+A2328V+Y2387F+E2335G+P2322A+ L2334M, L2336A+A2328V+Y2387F+E2335G+ P2322A+L2334G, L2336A+A2328V+Y2387F+ E2335G+P2322A, L2336A+A2328V+Y2387F+ E2335G+P2322V+L2334M, L2336A+A2328V+ Y2387F+E2335G+P2322V+L2334G, L2336A+

A2328V+Y2387F+E2335G+P2322V, L2336A+A2328V+Y2387F+E2335G+L2334M, L2336A+A2328V+Y2387F+E2335G+L2334G, L2336A+A2328V+Y2387F+E2335G, L2336A+A2328V+Y2387F, L2336A+A2328V+E2335G+P2322A+L2334M, L2336A+A2328V+E2335G+P2322A+L2334G, L2336A+A2328V+E2335G+P2322A, L2336A+A2328V+E2335G+P2322V+L2334M, L2336A+A2328V+E2335G+P2322V+L2334G, L2336A+A2328V+E2335G+P2322V, L2336A+A2328V+E2335G+L2334M, L2336A+A2328V+E2335G+L2334G, L2336A+A2328V+E2335G, L2336A+Y2387F+E2335G+P2322A+L2334M, L2336A+Y2387F+E2335G+P2322A+L2334G, L2336A+Y2387F+E2335G+P2322A, L2336A+Y2387F+E2335G+P2322V+L2334M, L2336A+Y2387F+E2335G+P2322V+L2334G, L2336A+Y2387F+E2335G+P2322V, L2336A+Y2387F+E2335G+L2334M, L2336A+Y2387F+E2335G+L2334G, L2336A+Y2387F+E2335G, L2336A+E2335G+P2322A+L2334M, L2336A+E2335G+P2322A+L2334G, L2336A+E2335G+P2322A, L2336A+E2335G+P2322V+L2334M, L2336A+E2335G+P2322V+L2334G, L2336A+E2335G+P2322V, L2336A+E2335G+L2334M, L2336A+E2335G+L2334G, L2336A+E2335G, A2328V+Y2387F+E2335G+P2322A+L2334M, A2328V+Y2387F+E2335G+P2322A+L2334G, A2328V+Y2387F+E2335G+P2322A, A2328V+Y2387F+E2335G+P2322V+L2334M, A2328V+Y2387F+E2335G+P2322V+L2334G, A2328V+Y2387F+E2335G+P2322V, A2328V+Y2387F+E2335G+L2334M, A2328V+Y2387F+E2335G+L2334G, A2328V+Y2387F+E2335G, A2328V+E2335G+P2322A+L2334M, A2328V+E2335G+P2322A+L2334G, A2328V+E2335G+P2322A, A2328V+E2335G+P2322V+L2334M, A2328V+E2335G+P2322V+L2334G, A2328V+E2335G+P2322V, A2328V+E2335G+L2334M, A2328V+E2335G+L2334G, A2328V+E2335G, Y2387F+E2335G+P2322A+L2334M, Y2387F+E2335G+P2322A+L2334G, Y2387F+E2335G+P2322A, Y2387F+E2335G+P2322V+L2334M, Y2387F+E2335G+P2322V+L2334G, Y2387F+E2335G+P2322V, Y2387F+E2335G+L2334M, Y2387F+E2335G+L2334G, Y2387F+E2335G, E2335G+P2322A+L2334M, E2335G+P2322A+L2334G, E2335G+P2322A, E2335G+P2322V+L2334M, E2335G+P2322V+L2334G, E2335G+P2322V, E2335G+L2334M, and E2335G+L2334G, wherein the positions are numbered by reference to the amino acid sequence set forth in SEQ ID NO: 1.

8. A nucleic acid molecule encoding a variant of a DNA polymerase of family A as defined in claim 1.

9. An expression vector comprising the nucleic acid molecule of claim 8.

10. A host cell comprising the nucleic acid molecule of claim 8.

11. A process for producing a variant of a DNA polymerase of family A as defined in claim 1, wherein a host cell comprising a nucleic acid molecule encoding a variant of a DNA polymerase of family A as defined in claim 1 is cultivated under culture conditions allowing for expression of the nucleic acid encoding said variant, and wherein the variant is optionally retrieved.

12. A kit for performing a nucleotide incorporation reaction comprising a DNA polymerase of family A as defined in claim 1, and one or more nucleotides.

13. The kit of claim 12, wherein the kit comprises one or more 3'-O-modified nucleotides.

14. The kit of claim 12, wherein the kit further comprises at least one nucleic acid primer.

* * * * *